(12) United States Patent
Munzert et al.

(10) Patent No.: US 8,143,247 B2
(45) Date of Patent: *Mar. 27, 2012

(54) COMBINATIONS FOR THE TREATMENT OF DISEASES INVOLVING CELL PROLIFERATION

(75) Inventors: Gerd Munzert, Ulm (DE); Martin Steegmaier, Reutlingen (DE); Anke Baum, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 232 days.

This patent is subject to a terminal disclaimer.

(21) Appl. No.: 12/437,280

(22) Filed: May 7, 2009

(65) Prior Publication Data

US 2009/0238828 A1    Sep. 24, 2009

Related U.S. Application Data

(63) Continuation of application No. 11/189,540, filed on Jul. 26, 2005, now abandoned.

(30) Foreign Application Priority Data

Aug. 14, 2004   (EP) .................................... 04019361
Aug. 17, 2004   (EP) .................................... 04019448

(51) Int. Cl.
  A61K 31/54     (2006.01)
  A61K 31/535    (2006.01)
  A01N 43/58     (2006.01)
  C07D 417/00    (2006.01)

(52) U.S. Cl. ....... 514/228.5; 544/61; 544/118; 544/231; 544/251; 544/238; 514/234.2; 514/249; 514/250

(58) Field of Classification Search ............... 514/234.2, 514/249, 250; 544/61, 118, 231, 251, 238
See application file for complete search history.

(56) References Cited

U.S. PATENT DOCUMENTS

| | | | |
|---|---|---|---|
| 4,957,922 | A | 9/1990 | Lammens et al. |
| 5,043,270 | A * | 8/1991 | Abrams et al. ............... 435/69.1 |
| 5,167,949 | A | 12/1992 | Ferrand et al. |
| 5,198,547 | A | 3/1993 | Bailey et al. |
| 5,424,311 | A | 6/1995 | Billhardt-Troughton et al. |
| 5,698,556 | A | 12/1997 | Chan |
| 6,096,924 | A | 8/2000 | Studer et al. |
| 6,156,766 | A | 12/2000 | Arita et al. |
| 6,174,895 | B1 | 1/2001 | Kleinman |
| 6,605,255 | B2 | 8/2003 | Kroll et al. |
| 6,806,272 | B2 | 10/2004 | Bauer et al. |
| 6,861,422 | B2 | 3/2005 | Hoffmann et al. |
| 6,875,868 | B2 | 4/2005 | Bonnert et al. |
| 7,238,807 | B2 | 7/2007 | Duran et al. |
| 7,241,889 | B2 | 7/2007 | Hoffmann et al. |
| 7,332,491 | B2 | 2/2008 | Grauert et al. |
| 7,371,753 | B2 | 5/2008 | Stadtmueller et al. |
| 7,414,053 | B2 | 8/2008 | Grauert et al. |
| 7,439,358 | B2 | 10/2008 | Linz et al. |
| 7,547,780 | B2 | 6/2009 | Grauert et al. |
| 7,625,899 | B2 | 12/2009 | Hoffmann et al. |
| 7,626,019 | B2 | 12/2009 | Duran et al. |
| 7,629,460 | B2 | 12/2009 | Grauert et al. |
| 7,700,769 | B2 | 4/2010 | Grauert et al. |
| 7,723,517 | B2 | 5/2010 | Grauert et al. |

(Continued)

FOREIGN PATENT DOCUMENTS

CA        2458699        3/2003

(Continued)

OTHER PUBLICATIONS

Goodman and Gilman (the Pharm. Basis of therapeutics 9th ed. 1225-1232 and 1269-1271.*
ACPS Meeting, Background Information. "Scientific considerations of plymorphism in pharmaceutical solids: abbreviated new drug applications". Oct. 2002.
Ahlenius, T. List of cardiovascular disorder/diseases. Ahlenius, Karolinska Institutet. Stockholm, Sweden. Cardiovascular Diseases, p. 1-34, Apr. 2007.
Arnold, K. "Collaboration to play key role in NCI's future, director says". Journal of the National Cancer Institute, Jun. 5, 2002, pp. 790-792, vol. 94, No. 11.

(Continued)

*Primary Examiner* — Brandon Fetterolf
*Assistant Examiner* — Shirley V Gembeh
(74) *Attorney, Agent, or Firm* — Michael P. Morris; Anthony P. Bottin

(57) ABSTRACT

Disclosed are pharmaceutical compositions for the treatment of diseases which involve cell proliferation. Also disclosed are methods for the treatment of said diseases, comprising co-administration of a compound 1 of Formula (I)

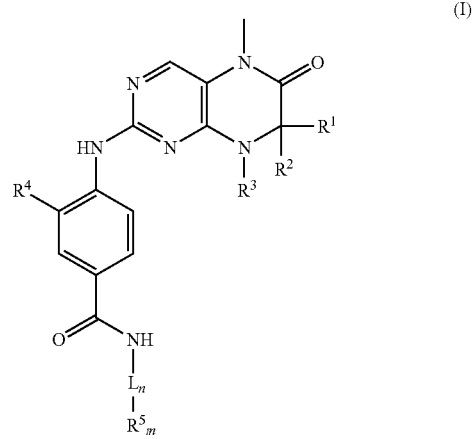

wherein the groups L, $R^1$, $R^2$, $R^3$, $R^4$ and $R^5$ have the meanings given herein and of an effective amount of an active compound 2 and/or co-treatment with radiation therapy, in a ratio which provides an additive and synergistic effect, and to the combined use of a compound 1 of Formula (I) and of an effective amount of an active compound 2 and/or radiotherapy for the manufacture of corresponding pharmaceutical combination preparations.

11 Claims, 8 Drawing Sheets

U.S. PATENT DOCUMENTS

| | | | |
|---|---|---|---|
| 7,728,134 B2 | 6/2010 | Linz et al. |
| 7,750,152 B2 | 7/2010 | Hoffman et al. |
| 7,759,347 B2 | 7/2010 | Hoffmann |
| 7,759,485 B2 | 7/2010 | Linz et al. |
| 7,807,831 B2 | 10/2010 | Grauert et al. |
| 7,816,530 B2 | 10/2010 | Grauert |
| 2002/0183292 A1 | 12/2002 | Pairet et al. |
| 2002/0183293 A1 | 12/2002 | Banerjee et al. |
| 2003/0130286 A1 | 7/2003 | Denny et al. |
| 2004/0029885 A1 | 2/2004 | Bauer et al. |
| 2004/0147524 A1 | 7/2004 | Bauer et al. |
| 2004/0176380 A1 | 9/2004 | Hoffmann et al. |
| 2005/0014760 A1 | 1/2005 | Hoffmann et al. |
| 2005/0014761 A1 | 1/2005 | Hoffmann et al. |
| 2005/0148501 A1 | 7/2005 | Palmer et al. |
| 2005/0159414 A1 | 7/2005 | Nickolaus et al. |
| 2005/0165010 A1 | 7/2005 | Nickolaus et al. |
| 2006/0004014 A1 | 1/2006 | Hoffmann et al. |
| 2006/0009457 A1 | 1/2006 | Hoffmann et al. |
| 2006/0025411 A1 | 2/2006 | Hoffmann et al. |
| 2006/0035902 A1 | 2/2006 | Linz et al. |
| 2006/0035903 A1 | 2/2006 | Mohr et al. |
| 2006/0046989 A1 | 3/2006 | Grauert et al. |
| 2006/0047118 A1 | 3/2006 | Stadtmueller et al. |
| 2006/0052383 A1 | 3/2006 | Grauert et al. |
| 2006/0058311 A1 | 3/2006 | Munzert et al. |
| 2006/0074088 A1 | 4/2006 | Munzert et al. |
| 2006/0079503 A1 | 4/2006 | Schwede et al. |
| 2007/0208027 A1 | 9/2007 | Duran et al. |
| 2007/0213528 A1 | 9/2007 | Duran et al. |
| 2007/0213529 A1 | 9/2007 | Duran et al. |
| 2007/0213530 A1 | 9/2007 | Duran et al. |
| 2007/0213531 A1 | 9/2007 | Duran et al. |
| 2007/0213534 A1 | 9/2007 | Duran et al. |
| 2007/0219369 A1 | 9/2007 | Duran et al. |
| 2008/0108812 A1 | 5/2008 | Grauert et al. |
| 2008/0113992 A1 | 5/2008 | Grauert et al. |
| 2008/0171747 A1 | 7/2008 | Hoffman et al. |
| 2008/0177066 A1 | 7/2008 | Linz et al. |
| 2008/0194818 A1 | 8/2008 | Grauert et al. |
| 2008/0221099 A1 | 9/2008 | Munzert et al. |
| 2008/0293944 A1 | 11/2008 | Hoffmann et al. |
| 2008/0319190 A1 | 12/2008 | Grauert et al. |
| 2008/0319192 A1 | 12/2008 | Grauert et al. |
| 2008/0319193 A1 | 12/2008 | Grauert et al. |
| 2009/0018333 A1 | 1/2009 | Grauert et al. |
| 2009/0023733 A1 | 1/2009 | Cage et al. |
| 2009/0030004 A1 | 1/2009 | Linz et al. |
| 2009/0124628 A1 | 5/2009 | Hoffmann et al. |
| 2009/0143379 A1 | 6/2009 | Mohr et al. |
| 2009/0238828 A1 | 9/2009 | Munzert et al. |
| 2009/0280115 A1 | 11/2009 | Maier et al. |
| 2009/0298840 A1 | 12/2009 | Linz et al. |
| 2010/0029642 A1 | 2/2010 | Hoffmann et al. |
| 2010/0249412 A1 | 9/2010 | Linz et al. |
| 2010/0249458 A1 | 9/2010 | Linz et al. |
| 2010/0280037 A1 | 11/2010 | Linz et al. |
| 2010/0324288 A1 | 12/2010 | Hoffmann et al. |

FOREIGN PATENT DOCUMENTS

| | | |
|---|---|---|
| CA | 2517020 | 9/2004 |
| CA | 2517010 | 11/2004 |
| CA | 2576290 | 2/2006 |
| EP | 143478 | 6/1985 |
| EP | 347146 | 12/1989 |
| EP | 399856 | 11/1990 |
| EP | 429149 | 5/1991 |
| ES | 2287583 | 12/2007 |
| RU | 2002125451 A | 1/2004 |
| WO | 9609045 | 3/1996 |
| WO | 9634867 | 11/1996 |
| WO | 9636597 | 11/1996 |
| WO | 9811893 | 3/1998 |
| WO | 0119825 | 3/2001 |
| WO | 0170741 | 9/2001 |
| WO | 0178732 | 10/2001 |
| WO | 02057261 | 7/2002 |
| WO | 02076954 | 10/2002 |
| WO | 02076985 | 10/2002 |
| WO | 03020722 | 3/2003 |
| WO | 03093249 | 11/2003 |
| WO | 2004014899 | 2/2004 |
| WO | 2004076454 | 9/2004 |
| WO | 2004093848 | 11/2004 |
| WO | 2005067935 | 7/2005 |
| WO | 2006/018182 | 2/2006 |
| WO | 2006/018221 | 2/2006 |
| WO | 2006018185 | 2/2006 |
| WO | 2006018220 | 2/2006 |
| WO | 2006018221 | 2/2006 |
| WO | 2006021378 | 3/2006 |
| WO | 2007090844 | 8/2007 |
| WO | 2009019205 | 2/2009 |

OTHER PUBLICATIONS

BBC News/Health, Killer Breast Cancern Therapy Hope, www.newsvote.bbc/co./uk, downloaded Mar. 26, 2009.

Bennett, J.C., et al., "Textbook of Medicine", Part XIV, Oncology, 1997.

Blain, S. W. et al., "Differential interaction of the cyclin-dependent kinase (Cdk) Inhibitor p27KIP with cyclin A-Cdk2 and cyclin D2-Cdk4". The Journal of Biological Chemistry, vol. 272, No. 41, Issue Oct. 10, 1997, pp. 25862-25872.

Dipolar aprotic solvent. Exhibit A, IUPAC Compendium of Chemical Terminology, 2nd Edition, 1997.

Doerwald, F.Z. "Side reactions in organice synthesis". 2005.

Eurasian Opinion, Appln No. 2007/00389/28, Maly Slatoustinsky per., d.10, kv.15, 101000 Moscow, Russia, "EVROMARKPAT", 2007.

Ferrand, G., et al., "Synthesis and potential antiallergic activity of new pteridinones and related compounds". Eur. J. Med. Chem, 31, 1996, pp. 273-280. XP--2246920.

Giron, G. "Thernal analysis and calorimetric methods in the characterization of plymorphs and solvates". Thermochimica Acta 248, 1995, pp. 1-59.

Goodman-Gilman's "The Pharmacological Basis of Therapeutics". Ninth edition, 1996, pp. 1225-1271.

Ito, Y., et al., "Polo-like kinase 1 (PLK) expression is associated with cell proliferative activity and cdc2 expression in malignant-lymphoma of the thyroid". Anticancer Research, 2004, vol. 24, No. 1, pp. 259-263.

Jaworska, J., et al., "Review of methods for assessing the applicability domains of SARS and QSARS". Sponsor: The European Commission—Joint Research Ctr., Institute for Health and Consumer Protection—ECVAM, Italy, 2004.

Kashima, M. K. et al., "Expression of polo-like kinase (PLK1) in non-Hodgkin's lymphomas". NCBI, PubMed, 2005.

Leukemia & Lymphoma Society—Disease Information-Lymphoma. www.leukemia-lymphoma.org/all_page?item_id-7030, downloaded Mar. 26, 2009..

Leukemia & Lymphoma Society—Disease Information. www.leukemia-lymphoma.org/all_page?item_id-7026, downloaded Mar. 26, 2009.

Marko, D. et al., "Intracellular localization of 7-benzylamino-6-chloro-2-piperazino-4-pyrrolidino-pteridine in membrane structures impeding the inhibition of cytosolic cyclic AMP-specific phosphodiesterase". Biochemical Pharmacology, 63, 2002, pp. 669-676.

Masuda, Y. et al., "B-Hydroxyisovalerylshikonin induces apoptosis in human leukemia cells by inhibiting the activity of a polo-like kinase 1 (PLK)". 2003, Oncogene, 22, pp. 1012-1023.

MedlinePlus: Bacterial Infections. www.nim.nih.gov/medlineplus/print/bacterialinfections.htm, downloaded Mar. 26, 2009.

MedlinePlus: Viral Infections. www.nim.nih.gov/medlineplus/print/viralinfections.htm, downloaded Mar. 26, 2009.

Merck Manual of Medical Information—Home Edition, Section 17. "Parasitic Infections". Chapter 184, 2003.

Mito, K., et al., "Expression of polo-like kinase (PLK1) in non-Hodgkin's lymphomas". NCBI, PubMed, 2005, Leuk. Lymphoma, 46(2), pp. 251-231.

Nagao, K. et al., "Effect of MX-68 on airway inflammation and hyperresponsiveness in mice and guinea-pigs". Journal of Pharmacy and Pharmacology, JPP 2004, 56, pp. 187-196.
National Institute of Neurological Disorders, Index Stroke, 2006.
National Kidney Foundation: Chronic Kidney Disease (CKD). www.kidney.org/kidneydisease/ckd/index.cfm, downloaded Mar. 26, 2009.
Norman, P. "PDE4 inhibitors". 1999, Ashley Publications Ltd., pp. 1101-1118.
Office Action mailed Dec. 10, 2003 for U.S. Appl. No. 10/226,710, filed Aug. 23, 2002.
Office Action mailed Apr. 28, 2004 for U.S. Appl. No. 10/374,876, filed Feb. 26, 2003.
Ohio Dept of Health, "Brain and Other Central Nervous System Cancer in Ohio, 1997-2001". Sep. 2004, pp. 1-4.
Rylander, P.N. "Hydrgenation Methods". 1985, Chapter 13.
Rylander, P.N. "Hydrgenation Methods". 1985, Chapters 3, 4.
Rylander, P.N. "Hydrgenation Methods". 1985, Chapters 8, 9, 10, 11.
Rylander, P.N. "Hydrgenation Methods". 1985, Chapter 5, 6, 7.
Rylander, P.N., "Hydrogenation Methods". 1985, Chapters 1, 2.
Santing, R. E. et al., "Brochodilatory and anti-inflammatory properties of inhaled selective phosphodiesterase inhibitors in a guinea pig model of allergic asthma". European Journal of Pharmacology, 429, 2001, pp. 335-344.
Savelli, F. et al., "Heterotricyclic system Part II—synthesis of new pyrido[1'2':4,5]pyrazino[3,2-d] pyrimidines". Bollettino Chimico Farmaceutico, 131(8), Sep. 1992, pp. 309-312.
Snyder, J. S. et al., "Common bacteria whose susceptibility to antimicrobials is no longer predictable". NCBI, PubMed, 2000, J. Med. Liban, 48, pp. 208-214.
Sugar, A. M. et al., "Comparison of three methods of antifungal susceptibility testing with the proposed NCCLS standard broth macrodilution assay: lack of effect of phenol red". Mycology, Diagn Microbiol. Infect. Dis. 1995, 21—pp. 129-133.
Takai, N. et al., "Polo-like kinases (PLKs) and cancer". Oncogene, 2005, 24, pp. 287-291.
Tenbrink, R. E. et al., "Antagonist, partial agonist, and full agonist imidazo[1,5-a]quinoxaline amides and carbamates acting through the BABA/Benzodiazepine receptor". J. Med. Chem. 1994, 37, pp. 758-768.
Turner, W.W.et al., "Recent advances in the medicinal chemistry of antifungal agents". Current Pharmacutical Design, 1996, 2, pp. 209-224.
Verschuren, E.W. et al., "The cell cycle and how it is steered by Kaposi's sarcoma-associated herpesvirus cyclin". Journal of General Virology, 2004, 85, pp. 1347-1361.
Vippagunta, S. R. et al., "Crystalline solids". Advanced Drug Delivery Reviews, 48, 2001, pp. 3-26.
Viral Defense Foundation. www.viraldefense.org/mission.htm, downloaded Mar. 26, 2009.
Visiting Nurse Association of America. www.vnaa.org/gen/Germ_Protection_Center_Cold_and_Flu_Resources,html, downloaded Mar. 26, 2009.
Voskoglou-Nomikos, T. et al., "Clinical predictive value of the in vitro cell line, human xenograft, and mouse allograft preclinical cancer models". Clinical Cancer Research vol. 9, 2003, pp. 4227-4239.
Organic Chemistry, Grupo Editorial Iberoamerica, Section 13, 3, pp. 301-302, 1983 (best copy available in Spanish).
Webster's Comprehensive Dictionary, 1996, pp. 1013-1014.
Wolf, D. E.et al., "The structure of rhizopterin". Contribution from the Research Labs of Merck and Co. Inc. Nov. 1947, Journal of American Chem. Soc., vol. 69, pp. 2753- 2759. XP002352205.
Ghandi, L, et al., "An Open-Label Phase II Trial of the PLK Inhibitor BI 2536 in Patients with Sensitive Relapse Small Cell Lung Cancer". ASCO Meeting 2009.

Ahmad, N. "Polo-like kinase (Plk) 1: a novel target for the treatment of prostate cancer". The FASEB Journal. 2004, 18:5-7. Dept of Dermatology, Univ. Wisconsin, pp. 5-7.
Chen, J.X. et al., "Parallel differentiated recognition of ketones and acetals". Angewandte Chemie Int. Ed, vol. 37, Issue 1/2, p. 91-93, 1998.
Dyson, G, et al. "The Chemistry of Synthetic Drugs". 1964, p. 12-19.
International Search Report and Written Opinion for PCT/EP2005/008623 mailed Nov. 23, 2005.
International Search Report and Written Opinion for PCT/EP2005/008626 mailed Feb. 10, 2006.
Jamieson, C. et al., "Application of ReactArray Robotics and Design of Experiments Techniques in Optimisation of Supported Reagent Chemistry". Org. Proc. Res. & Dev., 2002, 6, p. 823-825.
Kimball, S. D. et al., "Cell cycle kinases and checkpoint regulation in cancer". Annual Reports in Medicinal Chemistry, 36, Chapter 14, 2001, pp. 139-148.
Krause, M. et al., "Combination of Radiation and Polo-like Kinase 1 Inhibition with BI 6727 in tumour model A431". Strahlenther Onkol, 187, S1, 53 (v17-6), 2011.
Kummer B, et al., "Combination of Radiation and Polo-like Kinase 1 Inhibition with BI6727 in tumour model A431". Vortrag. 20. Symposium •Experimentelle Strahlentherapie und klinische Strahlenbiologie, Exp. Strahlenther. Klin. Strahlenbiol. 20: 93-96 (2011) (Lecture 20, Symposium Experimental Radiation Therapy and Clinical Radiation Biology.).
Kummer, B. et al., Presentation: "Combination of irradiation and polo-like kinase 1 inhibition with BI 6727 in tumour model A 431". OncoRay—National Centre for Radiation Research in Oncology, Dresden 2011, Experimental Radiotherapy and Clinical Radiobiology.
Mashkovkii, M.D., "Medicaments". Moscow, Novaja Volna, 2001, vol. 1, p. 11.
Mashkovskii, M.D. "Drugs", Handbook for Doctors, 1993, Part I, Ch.1, p. 8.
Mayer, SF, et al., "Enzyme-initiated domino (cascase) reactions". Chem. Soc. Rev, 2001, p. 332-339.
Mikhailov, I.B., Principles of Rational Pharmacotherapy. Handbook for clinical pharmacology for students of pediatric and medical faculties of medical high schools, St. Petersburg, Russia, "Foliant", 1999, p. 25.
Neidle, S. ed., "Cancer Drug Design and Discovery", Elsevier/Academic Press, 2008, p. 427-431.
Rocha Lima, C.M. et al. "Randomized phase II trial of gemcitabine plus irinotecan or docetaxel uin stage IIIB or stage IV NSCLC" Annals of Oncology, 15(3), p. 410-418, 2004.
Science, vol. 310, Oct. 21, 2005, p. 409, Chemistry: One After Another.
Souillac, P. et al., "Characterization of delivery systems, differential scanning calorimetry". (In Encyclopedia of Controlled Drug Delivery), 1999, John Wiley & Sons, pp. 212-227.
Turner, S., "The Design of Organic Syntheses". Elsevier, 1976, pp. 10 and 149.
Wagner, B. et al, "7-Benzylamino-6-chloro-2-piperazino-4-pyrrolidino-pteridine, a potent inhibitor of cAMP-specific phosphodiesterase, enhancing nuclear protein binding to the CRE consensus sequence in human tumour cells", Biochemical Pharmacology, Pergamon, Oxford, GB, 2002, pp. 659-668.
Wagner, G. et al., "Synthesis of new phrido[3',2':4,5] thieno '3,2-d] 1,2,3-triazine derivatives as antianaphylactics". Biosciences Dept of the University of Leipzig, Pharmazie (Pharmacy), 48, vol. 7,1993, pp. 514-518.
Wikipedia. "Melting Point", Jan. 17, 2007. http://en.wikipedia.org/wiki/Melting_point.

* cited by examiner

Figure 1.1
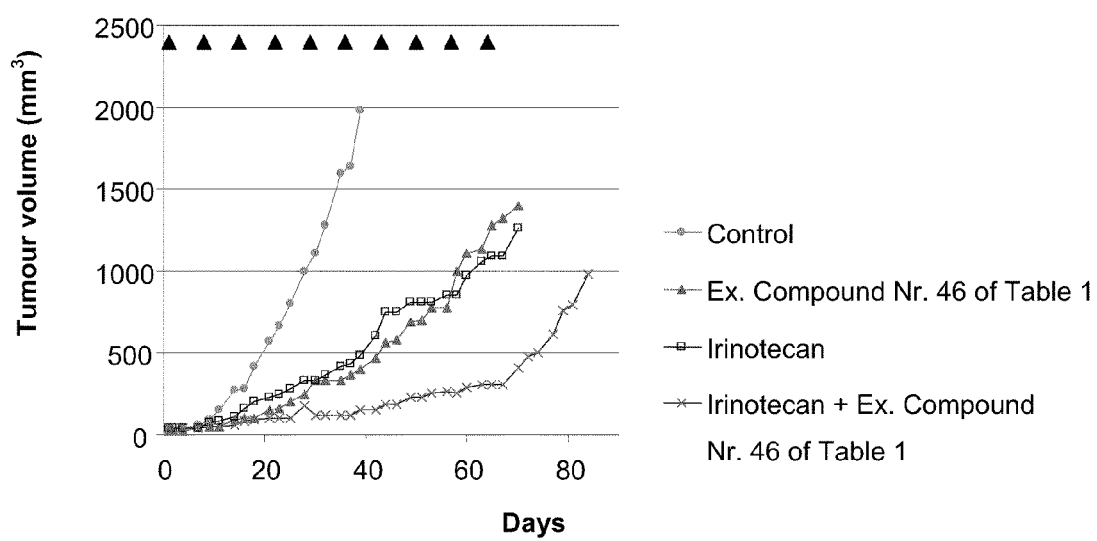

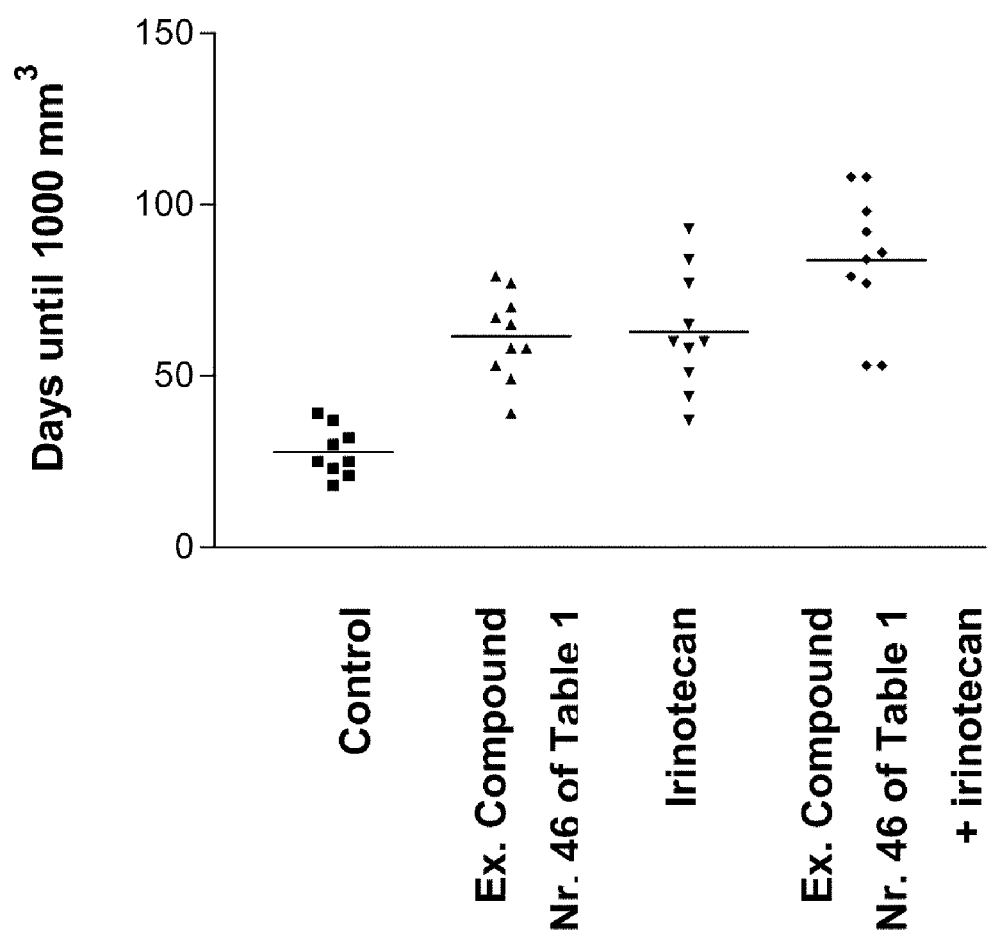
Figure 1.2

Figure 1.3
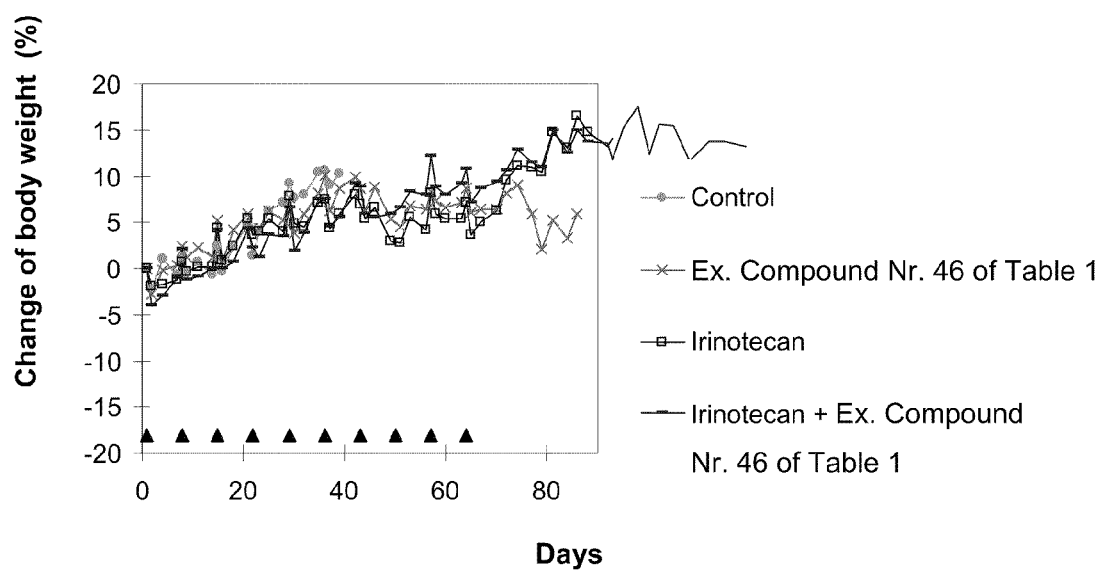

Figure 2.1
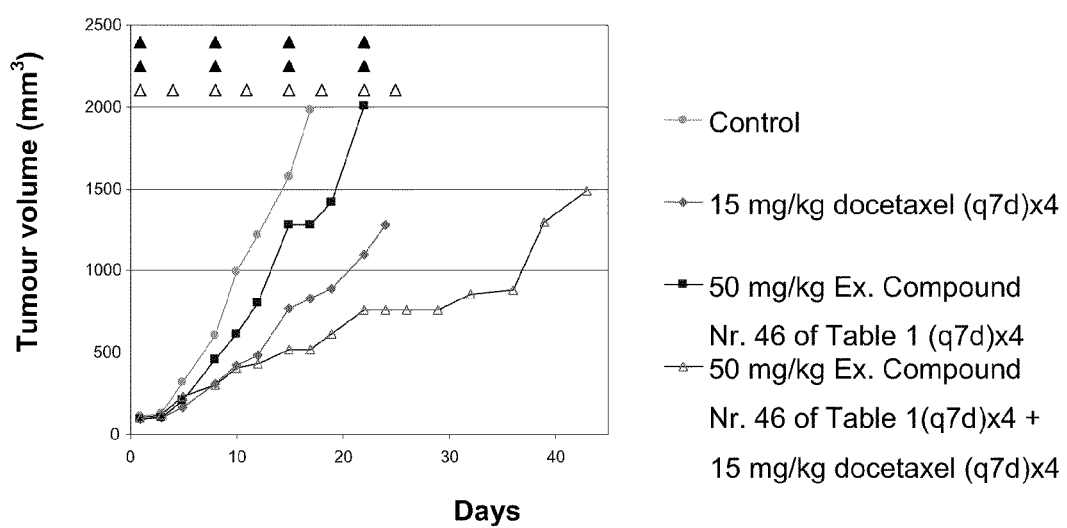

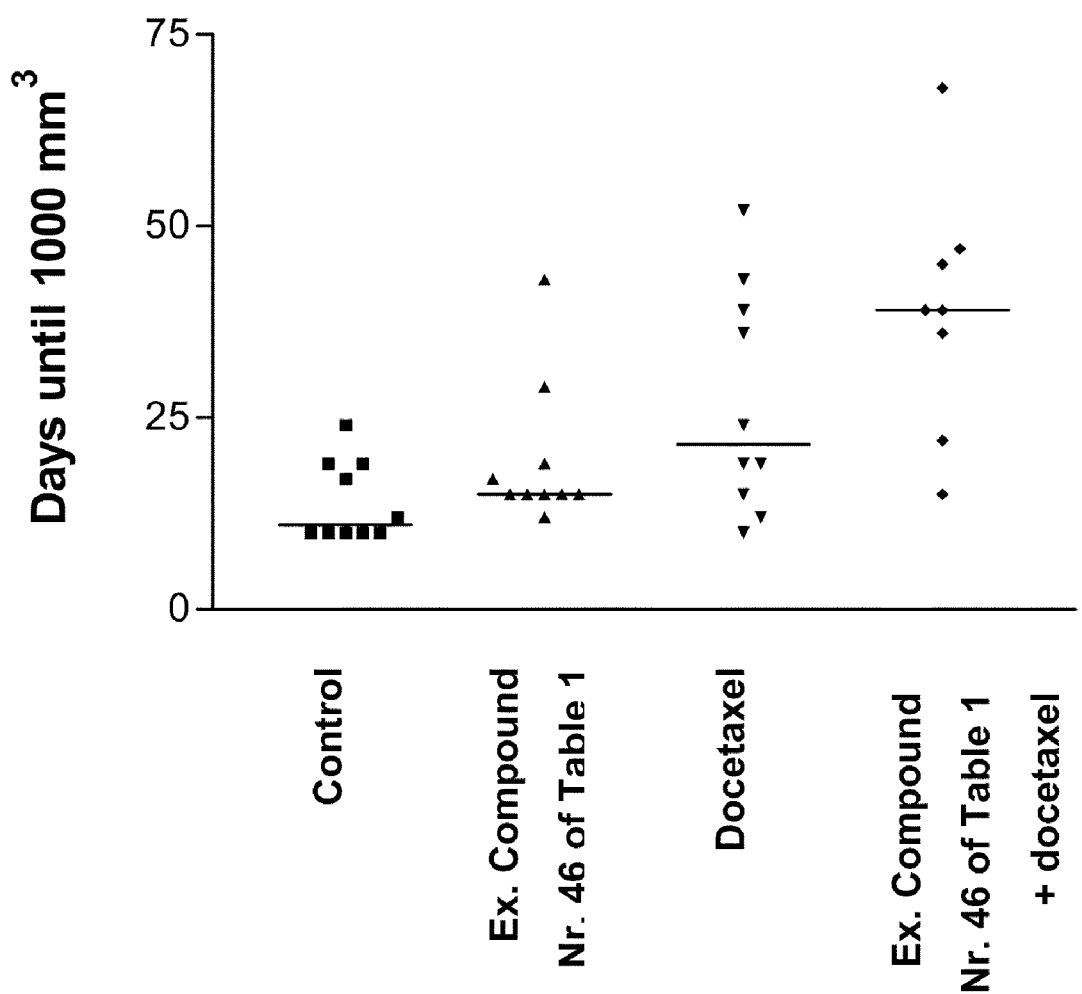
Figure 2.2

Figure 2.3
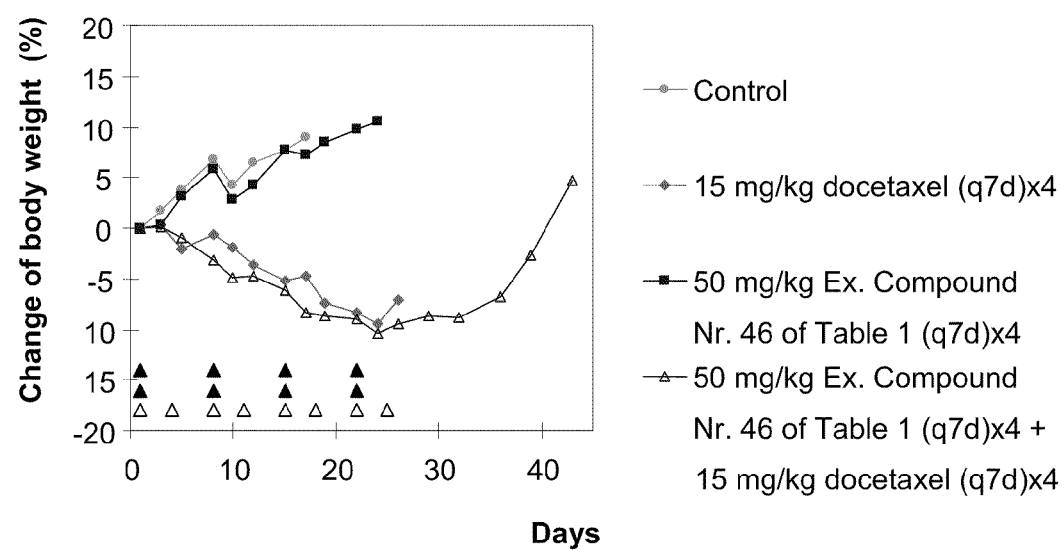

Figure 3.1
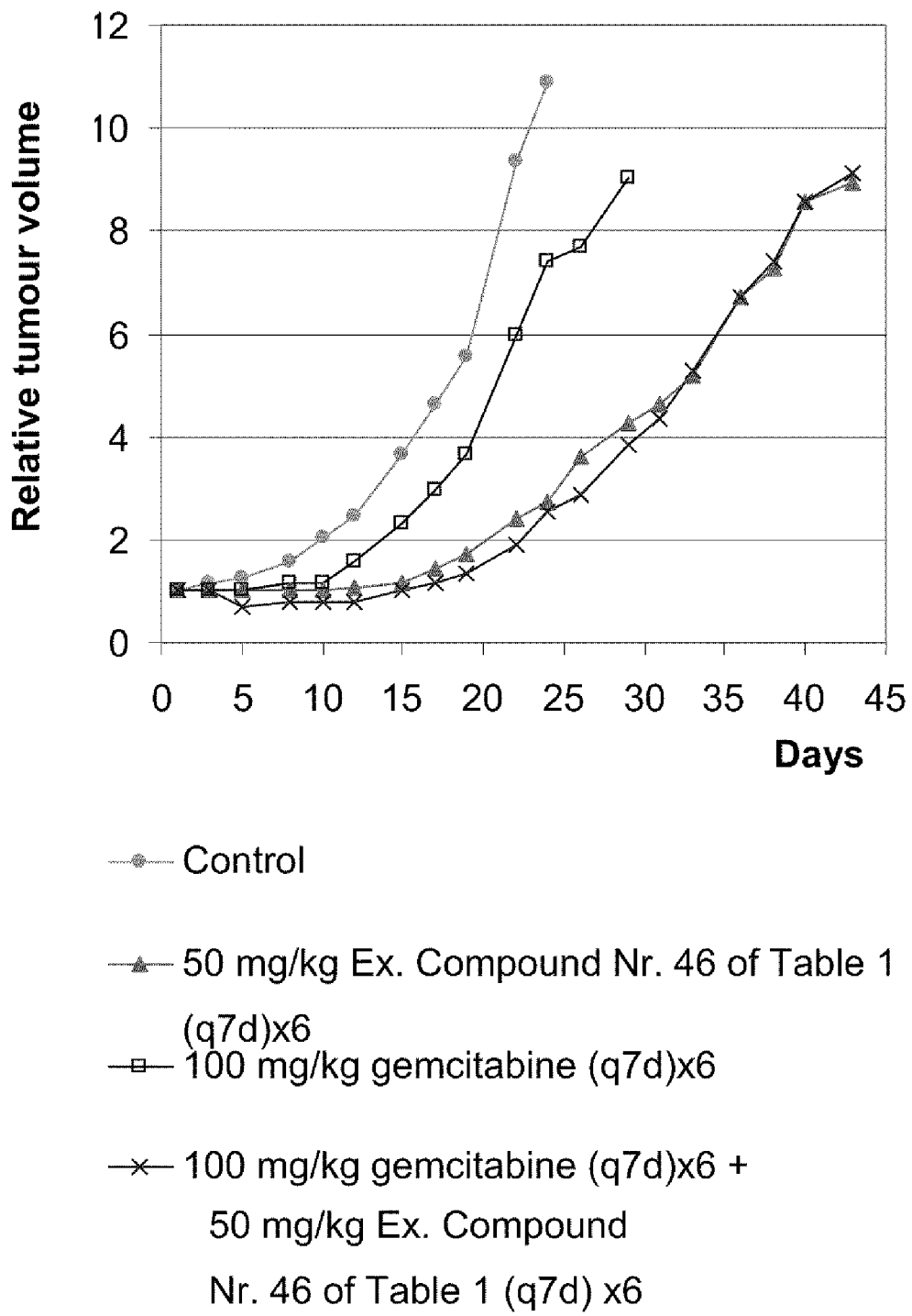

Figure 3.2
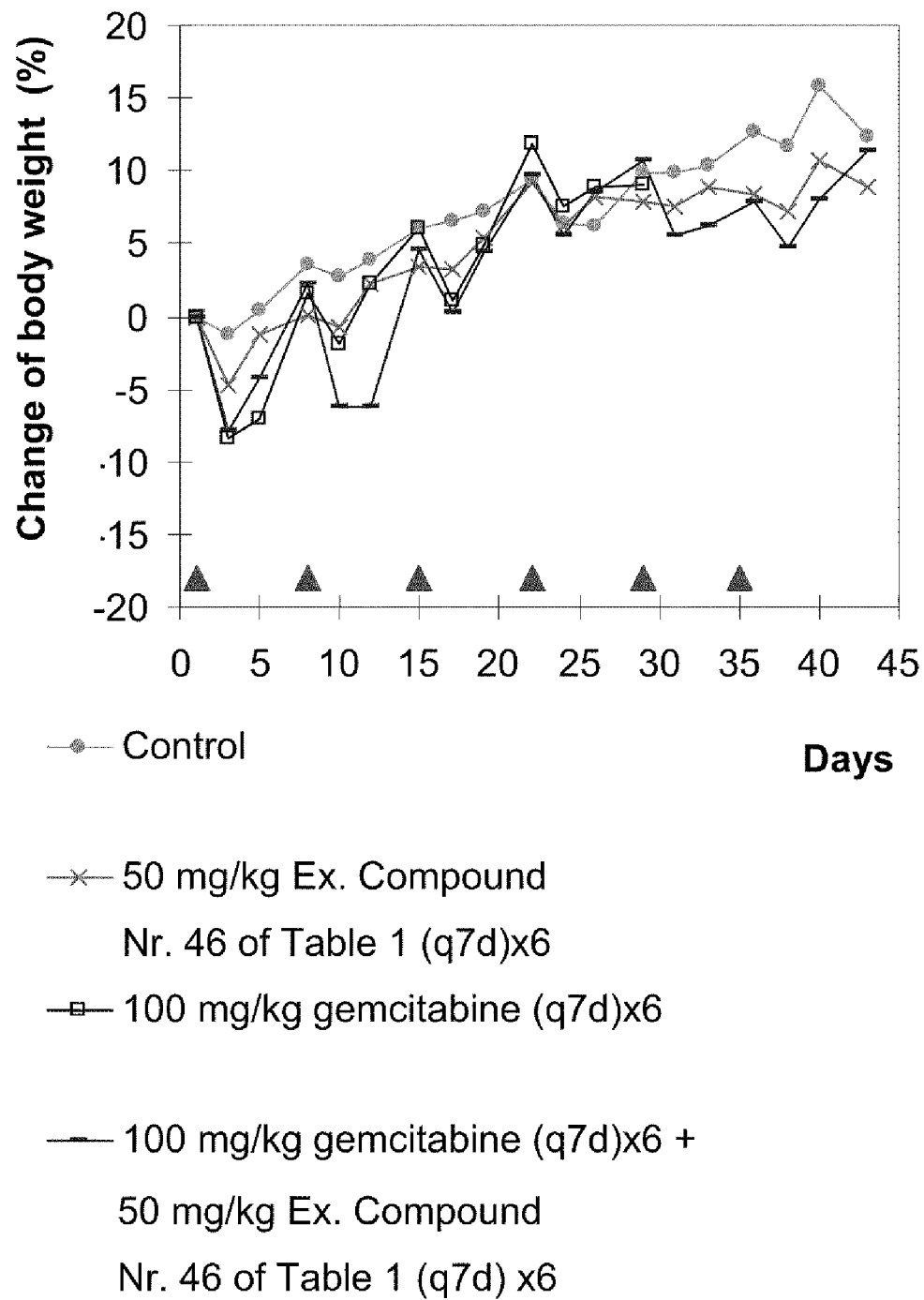

COMBINATIONS FOR THE TREATMENT OF DISEASES INVOLVING CELL PROLIFERATION

APPLICATION DATA

This application is a continuation application of U.S. Ser. No. 11/189,540 filed on Jul. 26, 2005 now abandoned which claims benefit to European Patent application nos. EP 04 019 361.7 filed Aug. 14, 2004 and EP 04 019 448.2 filed Aug. 17, 2004.

FIELD OF INVENTION

The invention relates to new pharmaceutical compositions for the treatment of diseases involving cell proliferation, migration or apoptosis of cancer cells, or angiogenesis and the preparation thereof. The invention further relates to a method for the treatment of diseases involving cell proliferation, migration or apoptosis of cancer cells, or angiogenesis, which method comprises co-administration to a person in need of such treatment and/or co-treatment of a person in need of such treatment with effective amounts of:
  (i) A compound 1 of Formula (I)

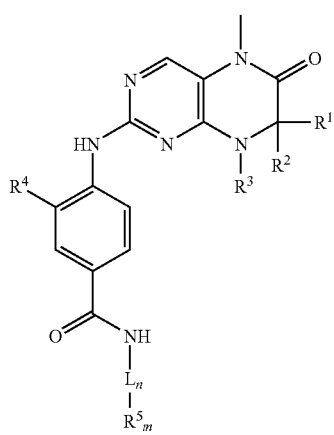

(I)

wherein the groups L, $R^1$, $R^2$, $R^3$, $R^4$ and $R^5$ have the meanings given in the claims and specification, optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof, and
  (ii) At least a further chemotherapeutic, immunotherapeutic or immunomodulatory, antiangiogenic, hormonal or naturally occurring, semi-synthetic or synthetic therapeutic agent 2; and/or
  (iii) Radiotherapy or radio-immunotherapy.

BACKGROUND OF THE INVENTION

Polo-like kinases (PLKs) are serine/threonine kinases that play important roles in regulating processes in the cell cycle. There are four PLKs disclosed in the state of the art, i.e. PLK-1, PLK-2, PLK-3, and PLK-4. PLKs play a role in the entry into and the exit from mitosis in mammalian cells. Especially for PLK-1 a central role with respect to the regulation of mitosis was shown (Glover et al. 1998, *Genes Dev.* 12:3777-87; Qian et al. 2001, *Mol Biol Cell.* 12:1791-9). Overexpression of PLK-1 seems to be strongly associated with neoplastic cells including cancers (WO 2004/014899).

Overexpression of PLK1 has been documented for various tumor types such as non-small cell lung cancer, squamous cell carcinomas, breast, ovary or papillary carcinomas as well as colorectal cancers (Wolf et al. 1997, *Oncogene* 14, pages 543-549; Knecht et al. 1999, *Cancer Res.* 59, pages 2794-2797; Wolf et al. 2000, *Pathol Res Pract.* 196, pages 753-759; Weichert et al. 2004, *Br. J. Cancer* 90, pages 815-821; Ito et al. 2004, *Br. J. Cancer* 90, pages 414-418; Takahashi et al. 2003, *Cancer Sci.* 94, pages 148-152).

For the treatment of diseases of oncological nature, a large number of chemotherapeutic, immunotherapeutic or immunomodulatory, antiangiogenic or hormonal agents have already been suggested, which can be used as monotherapy (treatment with one agent) or as combination therapy (simultaneous, separate or sequential treatment with more than one agent) and/or which may be combined with radiotherapy or radio-immunotherapy. In this respect, chemotherapeutic agent means a naturally occurring, semi-synthetic or synthetic chemical compound which, alone or via further activation, for example with radiations in the case of radio-immunotherapy, inhibits or kills growing cells, and which can be used or is approved for use in the treatment of diseases of oncological nature, which are commonly also denominated as cancers. In the literature, these agents are generally classified according to their mechanism of action. In this matter, reference can be made, for example, to the classification made in "Cancer Chemotherapeutic Agents", American Chemical Society, 1995, W. O. Foye Ed.

The efficacy of chemotherapeutic agents can be improved by using combination therapies with other chemotherapeutic, immunotherapeutic, immunomodulatory, antiangiogenic or hormonal compounds. Combination therapies constitute the gold standard in many settings of cancer therapy.

Even if the concept of combining several therapeutic agents or therapies already has been suggested, and although various combination therapies are under investigation and in clinical trials, there is still a need for new and efficient therapeutic compositions for the treatment of cancer diseases, which show advantages over standard therapies.

It is the purpose of the present invention to provide a combination therapy with the PLK Inhibitors of Formula (I) for the treatment of various cancer diseases.

DESCRIPTION OF THE INVENTION

Thus, within the meaning of the present invention, the following classes of chemotherapeutic agents are especially of interest, although not representing a limitation:
  Synthetic small molecule VEGF receptor antagonists
  Small molecule growth factor (GF) receptor antagonists
  Inhibitors of the EGF receptor and/or VEGF receptor and/or integrin receptors or any other protein tyrosine kinase receptors, which are not classified under the synthetic small-molecules
  Small molecule inhibitors of the Ras/Raf/MAPK or PI3K/AKT pathways or any other serine/threonine kinases.
  Inhibitors of the Ras/Raf/MAPK or PI3K/AKT pathways or any other serine/threonine kinases, which are not classified under the synthetic small-molecules
  Inhibitors directed to EGF receptor and/or VEGF receptor and/or integrin receptors or any other protein tyrosine kinase receptors, which are synthetically manufactured antibodies, antibody fragments or fusion proteins
  Compounds which interact with nucleic acids and which are classified as alkylating agents or platinum compounds
  Compounds which interact with nucleic acids and which are classified as anthracyclines, as DNA intercalators or as DNA cross-linking agents Anti-metabolites Naturally occurring, semi-synthetic or synthetic bleomycin type antibiotics (BLM-group antibiotics)

Inhibitors of DNA Transcribing Enzymes, Especially Topoisomerase I or topoisomerase II inhibitors Chromatin modifying agents Mitosis inhibitors, anti-mitotic agents, or cell-cycle inhibitors Compounds interacting with or binding tubulin Compounds inhibiting mitotic kinesins or other motor proteins including but not limited to Eg5, CENP-E, MCAK, Kid, MKLP-1

Proteasome inhibitors

Heat shock protein inhibitors

Compounds targeting the anti-apoptotic function of Bcl-2, Bcl-$x_L$ and like molecules Enzymes Hormones, hormone antagonists or hormone inhibitors, or inhibitors of steroid biosynthesis Steroids Cytokines, hypoxia-selective cytotoxins, inhibitors of cytokines, lymphokines, antibodies directed against cytokines or oral and parenteral tolerance induction strategies Supportive agents Antiinflammatory compounds such as but not limited to COX-2 inhibitors Chemical radiation sensitizers and protectors Photochemically activated drugs Synthetic poly- or oligonucleotides Other chemotherapeutic or naturally occurring, semi-synthetic or synthetic therapeutic agents, such as cytotoxic antibiotics, antibodies targeting surface molecules of cancer cells, antibodies targeting growth factors or their receptors, inhibitors of metalloproteinases, inhibitors of oncogenes, inhibitors of gene transcription or of RNA translation or protein expression, or complexes of rare earth elements.

The beneficial effects of the invention are mainly based on the additive and synergistic effects of the combined treatment, or to an improved tolerability of the treatment by the patient due, for example, to the administration of lower doses of the therapeutic agents involved.

Within the meaning of the present invention, the compound 1 has the structure of the following general Formula (I):

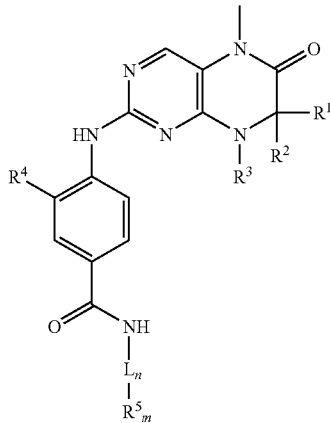

(I)

wherein $R^1$, $R^2$ which may be identical or different, denote hydrogen or optionally substituted $C_1$-$C_6$-alkyl, or $R^1$ and $R^2$ together denote a 2- to 5-membered alkyl bridge which may contain 1 to 2 heteroatoms, $R^3$ denotes hydrogen or a group selected from among optionally substituted $C_1$-$C_{12}$-alkyl, $C_2$-$C_{12}$-alkenyl, $C_2$-$C_{12}$-alkynyl and $C_6$-$C_{14}$-aryl, or a group selected from among optionally substituted and/or bridged $C_3$-$C_{12}$-cycloalkyl, $C_3$-$C_{12}$-cycloalkenyl, $C_7$-$C_{12}$-polycycloalkyl, $C_7$-$C_{12}$-polycycloalkenyl, $C_5$-$C_{12}$-spirocycloalkyl, $C_3$-$C_{12}$-heterocycloalkyl which contains 1 to 2 heteroatoms, and $C_3$-$C_{12}$-heterocycloalkenyl which contains 1 to 2 heteroatoms, or $R^1$ and $R^3$ or $R^2$ and $R^3$ together denote a saturated or unsaturated $C_3$-$C_4$-alkyl bridge which may contain 1 heteroatom, $R^4$ denotes a group selected from among hydrogen, —CN, hydroxy, —$NR^6R^7$ and halogen, or a group selected from among optionally substituted $C_1$-$C_6$-alkyl, $C_2$-$C_6$-alkenyl, $C_2$-$C_6$-alkynyl, $C_1$-$C_5$-alkyloxy, $C_2$-$C_5$-alkenyloxy, $C_2$-$C_5$-alkynyloxy, $C_1$-$C_6$-alkylthio, $C_1$-$C_6$-alkylsulphoxo and $C_1$-$C_6$-alkylsulphonyl, L denotes a linker selected from among optionally substituted $C_2$-$C_{10}$-alkyl, $C_2$-$C_{10}$-alkenyl, $C_6$-$C_{14}$-aryl, —$C_2$-$C_4$-alkyl-$C_6$-$C_{14}$-aryl, —$C_6$-$C_{14}$-aryl-$C_1$-$C_4$-alkyl, optionally bridged $C_3$-$C_{12}$-cycloalkyl and heteroaryl which contains 1 or 2 nitrogen atoms, n denotes 0 or 1 m denotes 1 or 2

$R^5$ denotes a group selected from among optionally substituted morpholinyl, piperidinyl, piperazinyl, piperazinylcarbonyl, pyrrolidinyl, tropenyl, $R^8$-diketomethylpiperazinyl, sulphoxomorpholinyl, sulphonylmorpholinyl, thiomorpholinyl, —$NR^8R^9$ and azacycloheptyl, $R^6$, $R^7$ which may be identical or different, denote hydrogen or $C_1$-$C_4$-alkyl, and $R^8$, $R^9$ denote unsubstituted nitrogen substituents at $R^5$, which may be identical or different, denote either hydrogen or a group selected from among $C_1$-$C_6$-alkyl, —$C_1$-$C_4$-alkyl-$C_3$-$C_{10}$-cycloalkyl, $C_3$-$C_{10}$-cycloalkyl, $C_6$-$C_{14}$-aryl, —$C_1$-$C_4$-alkyl-$C_6$-$C_{14}$-aryl, pyranyl, pyridinyl, pyrimidinyl, $C_1$-$C_4$-alkyloxycarbonyl, $C_6$-$C_{14}$-arylcarbonyl, $C_1$-$C_4$-alkylcarbonyl, $C_6$-$C_{14}$-arylmethyloxycarbonyl, $C_6$-$C_{14}$-arylsulphonyl, $C_1$-$C_4$-alkylsulphonyl- and $C_6$-$C_{14}$-aryl-$C_1$-$C_4$-alkylsulphonyl-, optionally in form of its tautomers, racemates, enantiomers, diastereomers and the mixtures thereof and optionally in form of the pharmacologically acceptable acid addition salts, solvates, hydrates, polymorphs, physiologically functional derivatives or prodrugs thereof.

Preferred compounds of Formula (I) are those wherein $R^1$ to $R^4$, $R^6$ and $R^7$ are as hereinbefore defined, and L denotes a linker selected from among optionally substituted $C_2$-$C_{10}$-alkyl, $C_2$-$C_{10}$-alkenyl, $C_6$-$C_{14}$-aryl, —$C_2$-$C_4$-alkyl-$C_6$-$C_{14}$-aryl, —$C_6$-$C_{14}$-aryl-$C_1$-$C_4$-alkyl, optionally bridged $C_3$-$C_{12}$-cycloalkyl and heteroaryl which contains 1 or 2 nitrogen atoms n denotes 1 m denotes 1 or 2

$R^5$ denotes a group which is bound to L via a nitrogen atom, selected from among optionally substituted morpholinyl, piperidinyl, $R^8$-piperazinyl, pyrrolidinyl, tropenyl, $R^8$-diketomethylpiperazinyl, sulphoxomorpholinyl, sulphonylmorpholinyl, thiomorpholinyl, —$NR^8R^9$ and azacycloheptyl, $R^8$, $R^9$ denote unsubstituted nitrogen substituents at $R^5$, which may be identical or different, hydrogen or a group selected from among $C_1$-$C_6$-alkyl, —$C_1$-$C_4$-alkyl-$C_3$-$C_{10}$- cycloalkyl, $C_3$-$C_{10}$-cycloalkyl, $C_6$-$C_{14}$-aryl, —$C_1$-$C_4$-alkyl-$C_6$-$C_{14}$-aryl, pyranyl, pyridinyl, pyrimidinyl, $C_1$-$C_4$-alkyloxycarbonyl, $C_6$-$C_{14}$-arylcarbonyl, $C_1$-$C_4$-alkylcarbonyl, $C_6$-$C_{14}$-arylmethyloxycarbonyl, $C_6$-$C_{14}$-arylsulphonyl, $C_1$-$C_4$-alkylsulphonyl and $C_6$-$C_{14}$-aryl-$C_1$-$C_4$-alkylsulphonyl.

Also preferred are compounds of Formula (I), wherein $R^1$ to $R^4$, $R^6$ and $R^7$ are as hereinbefore defined,
L denotes a linker selected from among optionally substituted $C_2$-$C_{10}$-alkyl, $C_2$-$C_{10}$-alkenyl, $C_6$-$C_{14}$-aryl, —$C_2$-$C_4$-alkyl-$C_6$-$C_{14}$-aryl, —$C_6$-$C_{14}$-aryl-$C_1$-$C_4$-alkyl, optionally bridged $C_3$-$C_{12}$-cycloalkyl and heteroaryl which contains 1 or 2 nitrogen atoms
n denotes 0 or 1
m denotes 1 or 2
$R^5$ denotes a group which is bound to L via a carbon atom, selected from among $R^5$-piperidinyl, $R^8R^9$-piperazinyl, $R^8$-pyrrolidinyl, $R^8$-piperazinylcarbonyl, $R^8$-tropenyl, $R^8$-morpholinyl and $R^8$-azacycloheptyl, and
$R^8$, $R^9$ denote unsubstituted nitrogen substituents at $R^5$, which may be identical or different, hydrogen or a group selected from among $C_1$-$C_6$-alkyl, —$C_1$-$C_4$-alkyl-$C_3$-$C_{10}$-cycloalkyl, $C_3$-$C_{10}$-cycloalkyl, $C_6$-$C_{14}$-aryl, —$C_1$-$C_4$-alkyl-$C_6$-$C_{14}$-aryl, pyranyl, pyridinyl, pyrimidinyl, $C_1$-$C_4$-alkyloxycarbonyl, $C_6$-$C_{14}$-arylcarbonyl, $C_1$-$C_4$-alkylcarbonyl, $C_6$-$C_{14}$-arylmethyloxycarbonyl, $C_6$-$C_{14}$-arylsulphonyl, $C_1$-$C_4$-alkylsulphonyl and $C_6$-$C_{14}$-aryl-$C_1$-$C_4$-alkylsulphonyl,
optionally in the form of the tautomers, the racemates, the enantiomers, the diastereomers and the mixtures thereof, and optionally the pharmacologically acceptable acid addition salts thereof.

Particularly preferred are compounds of Formula I wherein L, m, n and $R^3$ to $R^9$ are as hereinbefore defined, and
$R^1$, $R^2$ which may be identical or different, denote a group selected from among hydrogen, Me, Et, Pr, or
$R^1$ and $R^2$ together form a $C_2$-$C_4$-alkyl bridge,
optionally in the form of the tautomers, the racemates, the enantiomers, the diastereomers and the mixtures thereof, and optionally the pharmacologically acceptable acid addition salts thereof.

Especially preferred are compounds of Formula I wherein $R^1$, $R^2$, m, n and $R^5$ to $R^8$ are as hereinbefore defined, and
$R^3$ denotes a group selected from among optionally substituted $C_1$-$C_{10}$-alkyl, $C_3$-$C_7$-cycloalkyl, $C_3$-$C_6$-heterocycloalkyl and $C_6$-$C_{14}$-aryl or
$R^1$ and $R^3$ or $R^2$ and $R^3$ together denote a saturated or unsaturated $C_3$-$C_4$-alkyl bridge which may contain 1 to 2 heteroatoms,
$R^4$ denotes a group selected from among hydrogen, OMe, OH, Me, Et, Pr, OEt, NHMe, $NH_2$, F, CL, Br, O-propargyl, O-butynyl, CN, SMe, $NMe_2$, $CONH_2$, ethynyl, propynyl, butynyl and allyl,
and
L denotes a linker selected from among optionally substituted phenyl, phenylmethyl, cyclohexyl and branched $C_1$-$C_6$-alkyl,
optionally in the form of the tautomers, the racemates, the enantiomers, the diastereomers and the mixtures thereof, and optionally the pharmacologically acceptable acid addition salts thereof.

In a further embodiment, the compound 1 in accordance with the present invention is selected from the group consisting of the compounds of Formula (I) shown in the following Table

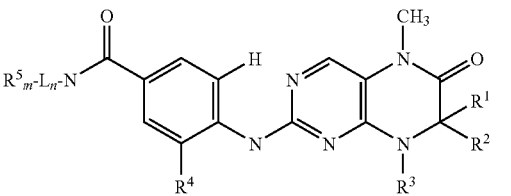

| Ex. | $R^1$ | $R^2$ | Config. $R^1$ or $R^2$ | $R^3$ | $R^4$ | $L_n$-$R^5_m$ |
|---|---|---|---|---|---|---|
| 27 | H | 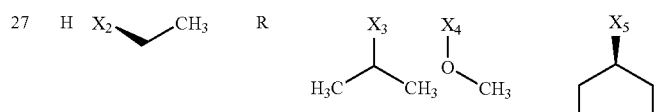 | R |  | | 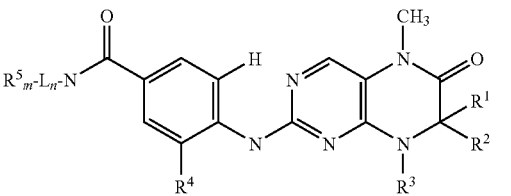 |
| 44 | H | 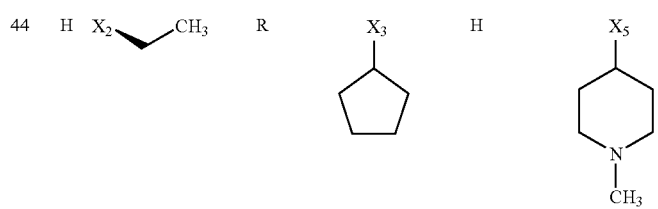 | R |  | H | |

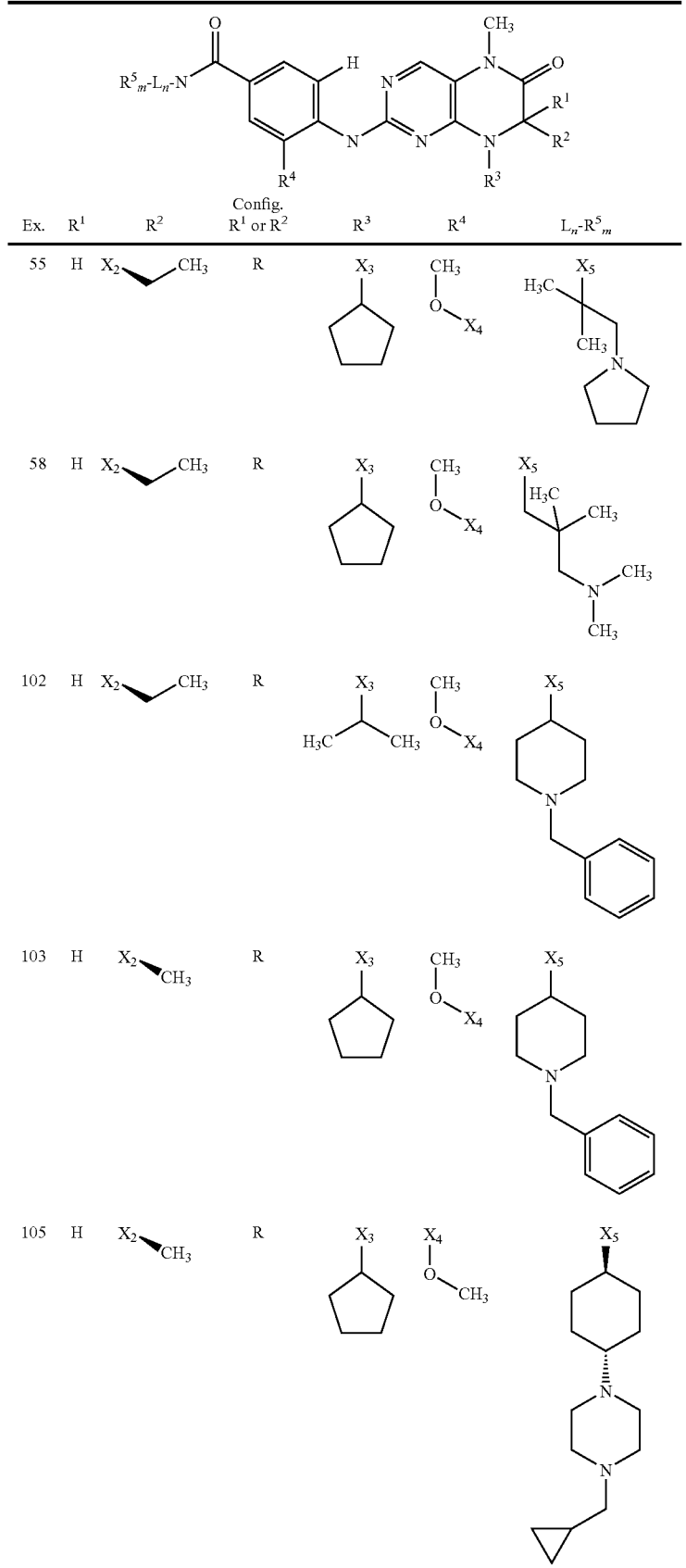

-continued
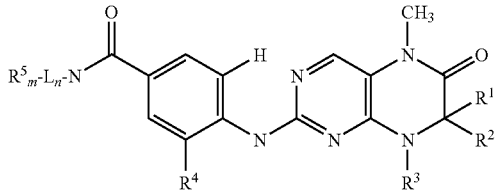
| Ex. | R¹ | R² | Config. R¹ or R² | R³ | R⁴ | Lₙ-R⁵ₘ |
|---|---|---|---|---|---|---|
| 110 | H | X₂—CH₂CH₃ | R | X₃—CH(CH₃)₂ | X₄—O—CH₃ | 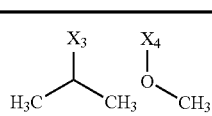 |
| 115 | H | X₂—CH₃ | R | X₃—cyclohexyl | X₄—O—CH₃ | 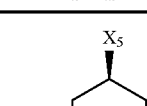 |
| 133 | H | X₂—CH₂CH₃ | R | X₃—cyclopentyl | X₄—O—CH₃ | 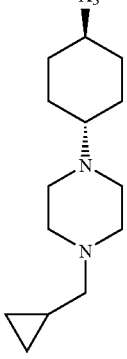 |
| 134 | H | X₂—CH₂CH₃ | R | X₃—cyclopentyl | X₄—O—CH₃ | 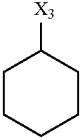 |

-continued

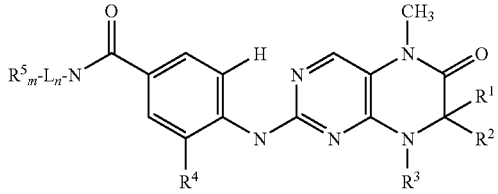

| Ex. | R¹ | R² | Config. R¹ or R² | R³ | R⁴ | $L_n$-$R^5_m$ |
|---|---|---|---|---|---|---|
| 234 | H | $X_1$—CH₃ (with H₃C-CH-CH₃) | R | $X_3$ (H₃C-CH-CH₃) | $X_4$ (O-CH₃) | $X_5$ (cyclohexyl-N-morpholine with H₃C and CH₃) |
| 240 | H | $X_1$—CH₃ | R | $X_3$ (cyclohexyl) | CH₃-O-$X_4$ | $X_3$ (H₃C-C(CH₃)-CH₂-N(CH₃)₂) | wherein the abbreviations $X_1$, $X_2$, $X_3$, $X_4$ and $X_5$ used in the Table in each case denote a link to a position in the general Formula shown in the Table instead of the corresponding groups $R^1$, $R^2$, $R^3$, $R^4$ and L-$R^5$.

This invention thus relates to a pharmaceutical composition comprising effective amounts of:
(i) A compound 1 of Formula (I) or optionally a polymorph, metabolite, hydrate, preferably the mono hydrate, solvate, individual optical isomers, mixtures of the individual enantiomers or racemates thereof, or a pharmaceutically acceptable salt thereof, and
(ii) At least one further chemotherapeutic or naturally occurring, semi-synthetic or synthetic therapeutic agent 2;

optionally in combination with one or more pharmaceutically acceptable excipients, and optionally adapted for a co-treatment with radiotherapy or radio-immunotherapy, in the form of a combined preparation for simultaneous, separate or sequential use in the treatment of diseases involving cell proliferation, migration or apoptosis of cancer cells, or angiogenesis, preferably involving cell proliferation or apoptosis of cancer cells.

In a preferred embodiment the instant invention is directed to a pharmaceutical composition, wherein the further chemotherapeutic or naturally occurring, semi-synthetic or synthetic therapeutic agent 2 is selected from the group consisting of compounds interacting with or binding tubulin, synthetic small molecule VEGF receptor antagonists, small molecule growth factor receptor antagonists, inhibitors of the EGF receptor and/or VEGF receptor and/or integrin receptors or any other protein tyrosine kinase receptors which are not classified under the synthetic small-molecules, inhibitors directed to EGF receptor and/or VEGF receptor and/or integrin receptors or any other protein tyrosine kinase receptors, which are fusion proteins, compounds which interact with nucleic acids and which are classified as alkylating agents or platinum compounds, compounds which interact with nucleic acids and which are classified as anthracyclines, as DNA intercalators or as DNA cross-linking agents, including DNA minor-groove binding compounds, anti-metabolites, naturally occurring, semi-synthetic or synthetic bleomycin type antibiotics, inhibitors of DNA transcribing enzymes, and especially the topoisomerase I or topoisomerase II inhibitors, chromatin modifying agents, mitosis inhibitors, anti-mitotic agents, cell-cycle inhibitors, proteasome inhibitors, enzymes, hormones, hormone antagonists, hormone inhibitors, inhibitors of steroid biosynthesis, steroids, cytokines, hypoxia-selective cytotoxins, inhibitors of cytokines, lymphokines, antibodies directed against cytokines, oral and parenteral tolerance induction agents, supportive agents, chemical radiation sensitizers and protectors, photo-chemically activated drugs, synthetic poly- or oligonucleotides, optionally modified or conjugated, non-steroidal anti-inflammatory drugs, cytotoxic antibiotics, antibodies targeting the surface molecules of cancer cells, antibodies targeting growth factors or their receptors, inhibitors of metalloproteinases, metals, inhibitors of oncogenes, inhibitors of gene transcription or of RNA translation or protein expression, complexes of rare earth elements, and photo-chemotherapeutic agents.

Preferred compounds include small molecule tyrosin kinase or serine/threonine kinase inhibitors, compounds interacting with nucleic acids classified as alkylating agents or anthracyclines, anti-metabolites, inhibitors of DNA transcribing enzymes such as topoisomerase I or II, tubulin binding drugs, anti-mitotic agents, antibodies targeting growth factors or their receptors and antibodies binding to surface molecules of cancer cells or ligands of these surface molecules in form of the hydrates and/or solvates and optionally in the form of the individual optical isomers, mixtures of the individual enantiomers or racemates thereof.

In another preferred embodiment the instant invention is directed to a pharmaceutical combination, wherein the further chemotherapeutic or naturally occurring, semi-synthetic or synthetic therapeutic agent 2 is selected from the group consisting of a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or a pharmaceutically acceptable salt thereof, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, an anti-cancer drug from plants such as paclitaxel (taxol), docetaxel or taxotere, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as bortezomib, an enzyme such as asparaginase, pegylated asparaginase (pegaspargase) or a thymidine-phosphorylase inhibitor, a gestagen or an estrogen such as estramustine (T-66) or megestrol, an anti-androgen such as flutamide, casodex, anandron or cyproterone acetate, an aromatase inhibitor such as aminogluthetimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17β-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon β, an interleukin such as IL-10 or IL-12, an anti-TNFα antibody such as etanercept, an immunomodulatory drug such as thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody, a tolerance induction agent, a biphosphonate or derivative thereof such as minodronic acid or its derivatives (YM-529, Ono-5920, YH-529), zoledronic acid monohydrate, ibandronate sodium hydrate or clodronate disodium, a nitroimidazole such as metronidazole, misonidazole, benznidazole or nimorazole, a nitroaryl compound such as RSU-1069, a nitroxyl or N-oxide such as SR-4233, an halogenated pyrimidine analogue such as bromodeoxyuridine, iododeoxyuridine, a thiophosphate such as WR-2721, a photo-chemically activated drug such as porfimer, photofrin, a benzoporphyrin derivative, a pheophorbide derivative, merocyanin 540 (MC-540) or tin etioporpurin, an ant-template or an anti-sense RNA or DNA such as oblimersen, a non-steroidal inflammatory drug such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lornoxicam, nimesulide, meloxicam, celecoxib, rofecoxib, or a pharmaceutically acceptable salt of a nonsteroidal inflammatory drug, a cytotoxic antibiotic, an antibody targeting the surface molecules of cancer cells such as apolizumab or 1D09C3, an inhibitor of metalloproteinases such as TIMP-1 or TIMP-2, Zinc, an inhibitor of oncogenes such as P53 and Rb, a complex of rare earth elements such as the heterocyclic complexes of lanthanides, a photo-chemotherapeutic agent such as PUVA, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, or a therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamoxifen and testolactone.

Preferred compounds include small molecule VEGF receptor antagonist such as vatalanib (PTK-787/ZK222584), SU-5416, SU-6668, SU-11248, SU-14813, AZD-6474, EGFR/HER2 antagonists such as CI-1033 or GW-2016, an EGFR antagonist such as iressa (gefitinib, ZD-1839), tarceva (erlotinib, OSI-774), PKI-166, EKB-569, HKI-272 or herceptin, an antagonist of the mitogen-activated protein kinase such as BAY-43-9006 or BAY-57-9006, atrasentan, rituximab, cetuximab, Avastin™ (bevacizumab), IMC-1C11, erbitux (C-225), DC-101, EMD-72000, vitaxin, imatinib, an alkylating agent or a platinum compound such as melphalan, cyclophosphamide, cisplatin, carboplatin, oxaliplatin, satraplatin, daunorubicin, doxorubicin (adriamycin), liposomal doxorubicin (doxil), epirubicin, idarubicin, a pyrimidine or purine analogue or antagonist or an inhibitor of the nucleoside diphosphate reductase such as cytarabine, 5-fluorouracile (5-FU), pemetrexed, tegafur/uracil, gemcitabine, capecitabine, mercaptopurine, methotrexate, an anti-cancer drug such as paclitaxel (taxol) or docetaxel, a vinca alkaloid such as navelbine, vinblastin, vincristin, vindesine or vinorelbine, an antimitotic peptide such as dolastatin, an epipodophyllotoxin or a derivative of podophyllotoxin such as etoposide or teniposide, a non-steroidal inflammatory drug such as meloxicam, celecoxib, rofecoxib, an antibody targeting the surface molecules of cancer cells such as apolizumab or 1D09C3 or the heat shock protein HSP90 modulator geldanamycin and its derivative 17-allylaminogeldanamycin or 17-AAG.

In another preferred embodiment the instant invention is directed to a pharmaceutical composition, wherein the further chemotherapeutic or naturally occurring, semi-synthetic or synthetic therapeutic agent 2 is selected from the group consisting of an anti-cancer drug from plants such as paclitaxel (taxol), docetaxel, a vinca alkaloid such as navelbine, vinblastin, vincristin, vindesine or vinorelbine, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an immunomodulatory drug such as thalidomide, its R- and S-enantiomers and its derivatives, or revimid (CC-5013)), an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as prop amidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), uracil mustard, fludarabine, gemcitabine, capecitabine, mercaptopurine, cladribine, thioguanine, methotrexate, pentostatin, hydroxyurea, or folic acid, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, a proteasome inhibitor such as bortezomib, a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, an antagonist of the mitogen-activated protein kinase such as BAY-43-9006 or BAY-57-9006, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, a quinazoline derivative such as 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or a pharmaceutically acceptable salt thereof, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, and an antibody targeting the surface molecules of cancer cells such as apolizumab or 1D09C3.

Preferred compounds include small molecule receptor antagonists such as vatalanib, SU 11248 or AZD-6474, EGFR or HER2 antagonists such as gefitinib, erlotinib, CI-1033 or Herceptin, antibodies such as bevacizumab, cetuximab, rituximab, DNA alkylating drugs such as cisplatin, oxaliplatin or carboplatin, anthracyclines such as doxorubicin or epirubicin, an antimetabolite such as 5-FU, pemetrexed, gemcitabine or capecitabine, a camptothecin such as irinotecan or topotecan, an anti-cancer drug such as paclitaxel or docetaxel, an epipodophyllotoxin such as etoposide or teniposide, a proteasome inhibitor such as bortezomib or antiinflammatory drugs such as celecoxib or rofecoxib, optionally in form of the pharmaceutically acceptable salts, in form of the hydrates and/or solvates and optionally in the form of the individual optical isomers, mixtures of the individual enantiomers or racemates thereof.

In another preferred embodiment the instant invention is directed to a pharmaceutical composition as defined hereinbefore, wherein the further chemotherapeutic or naturally occurring, semi-synthetic or synthetic therapeutic agent 2 is the quinazoline derivative 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or a pharmaceutically acceptable salt thereof.

In another preferred embodiment the instant invention is directed to a pharmaceutical composition as defined hereinbefore, wherein the further chemotherapeutic or naturally occurring, semi-synthetic or synthetic therapeutic agent 2 is the di-maleic acid salt of the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, or 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or the tautomers, stereoisomers or a pharmaceutically acceptable salt thereof.

In another preferred embodiment the instant invention is directed to a pharmaceutical composition as defined hereinbefore, wherein the further chemotherapeutic or naturally occurring, semi-synthetic or synthetic therapeutic agent 2 is the 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or a pharmaceutically acceptable salt thereof.

In another preferred embodiment the instant invention is directed to a pharmaceutical composition as defined hereinbefore, wherein the further chemotherapeutic or naturally occurring, semi-synthetic or synthetic therapeutic agent 2 is the 3-Z-[1-(4-(N-((4-methyl-piperazin-1-yl)-methylcarbonyl)-N-methyl-amino)-anilino)-1-phenyl-methylene]-6-methoxycarbonyl-2-indolinone, or a polymorph, metabolite or pharmaceutically acceptable salt thereof.

In another preferred embodiment the instant invention is directed to a pharmaceutical composition as defined hereinbefore, wherein the further chemotherapeutic or naturally occurring, semi-synthetic or synthetic therapeutic agent 2 is the monoethanesulfonate salt of 3-Z-[1-(4-(N-((4-methylpiperazin-1-yl)-methylcarbonyl)-N-methyl-amino)-anilino)-1-phenyl-methylene]-6-methoxycarbonyl-2-indolinone.

In another preferred embodiment the instant invention is directed to a pharmaceutical composition as defined hereinbefore, wherein the further chemotherapeutic or naturally occurring, semi-synthetic or synthetic therapeutic agent 2 is the 3-Z-[1-(4-dimethylaminomethylanilino)-1-(4-(2-carboxyethyl)phenyl)methylene]-6-fluoro-2-indolinone, or a polymorph, metabolite or pharmaceutically acceptable salt thereof.

In another preferred embodiment the instant invention is directed to a pharmaceutical composition, wherein the further chemotherapeutic or naturally occurring, semi-synthetic or synthetic therapeutic agent 2 is irinotecan, topotecan, oxaliplatin, docetaxel, paclitaxel, gemcitabine, pemetrexed, cisplatin, carboplatin, bevacizumab, cetuximab, gefitinib or erlotinib, particularly preferred irinotecan, docetaxel, gemcitabine, topotecan or paclitaxel.

In another preferred embodiment the instant invention is directed to a pharmaceutical composition as defined hereinbefore, wherein the further naturally occurring, semi-synthetic or synthetic therapeutic agent 2 is a compound which reduces the transport of hyaluronan mediated by one or more ABC transporters, or drug transport inhibitor, such as a P-glycoprotein (P-gp) inhibitor molecule or inhibitor peptide, an MRP1 inhibitor, an antibody directed against and capable of blocking the ABC transporter, an antisense oligomer, iRNA, siRNA or aptamer directed against one or more ABC transporters. Examples of P-glycoprotein (P-gp) inhibitor molecules in accordance with the present invention are zosuquidar (LY 335973), its salts (especially the trichloride salt) and its polymorphs, cyclosporin A (also known as cyclosporine), verapamil or its R-isomer, tamoxifen, quinidine, d-alpha tocopheryl polyethylene glycol 1000 succinate, VX-710, PSC833, phenothiazine, GF120918 (II), SDZ PSC 833, TMBY, MS-073, S-9788, SDZ 280-446, XR(9051) and functional derivatives, analogues and isomers of these.

Furthermore, where the compounds 2 carries an acidic moiety, suitable pharmaceutically acceptable salts thereof may include alkali metal salts (e.g. sodium or potassium salts), alkaline earth metal salts (e.g. calcium or magnesium salts) and salts formed with suitable organic ligands (e.g. quaternary ammonium salts).

The compounds 2 may have chiral centers and may occur as racemates, racemic mixtures and as individual diastereomers, or enantiomers with all isomeric forms being included in the present invention. Hence, where a compound is chiral, the separate enantiomers, substantially free of the others, are included within the scope of the invention. Further included are all mixtures of the two enantiomers. Also included within the scope of the invention are polymorphs and hydrates of the compounds of the instant invention.

The present invention includes within its scope prodrugs of a compound 1 of Formula (I) and of the further active ingredient 2. In general, such prodrugs will be functional derivatives of the compounds or active ingredients of this invention which are readily convertible in vivo into the required compound.

In a further embodiment the invention relates to a composition as defined hereinbefore, which inhibits the proliferation of various human tumour cell lines including but not limited to Saos-2, H4, MDA-MB-435S, MDA-MB453, MCF7, HeLa S3, HCT116, Colo 205, HT29, FaDu, HL-60, K-562, THP-1, HepG2, A549, NCI-H460, GRANTA-519, Raji, Ramos, BRO, SKOV-3, BxPC-3, Mia CaPa-2, DU145, PC-3, NCI-N87, MES-SA, SK-UT-1B and A431.

Another embodiment of the invention relates to the use of a pharmaceutical composition as defined hereinbefore for the preparation of a medicament for the treatment of oncological diseases, such as malignant human neoplasias.

In a preferred embodiment the instant invention relates to the use of a pharmaceutical composition as defined hereinbefore, wherein the oncological disease is selected from the group consisting of solid tumours.

In a further preferred embodiment the invention relates to the use of a pharmaceutical composition as defined hereinbefore, wherein the oncological disease is selected from the group consisting of urogenital cancers (such as prostate cancer, renal cell cancers, bladder cancers), gynecological cancers (such as ovarian cancers, cervical cancers, endometrial cancers), lung cancer, gastrointestinal cancers (such as colorectal cancers, pancreatic cancer, gastric cancer, oesophageal cancers, hepatocellular cancers, cholangiocellular cancers), head and neck cancer, malignant mesothelioma, breast cancer, malignant melanoma or bone and soft tissue sarcomas.

In a further preferred embodiment the invention relates to the use of a pharmaceutical composition as defined hereinbefore wherein the oncological disease is selected from the group consisting of refractory or relapsed multiple myeloma, acute or chronic myelogenous leukaemia, myelodysplastic syndrome, acute lymphoblastic leukaemia, Hodgkin's or non-Hodgkin's lymphoma.

In a further preferred embodiment, the disease is hormone sensitive or hormone refractory prostate cancer, ovarian carcinoma, or small cell lung cancer.

In a further preferred embodiment the invention relates to the use of a composition as defined hereinbefore, wherein the oncological disease is characterized by inappropriate cellular proliferation, migration, apoptosis or angiogenesis, preferably by inappropriate cellular proliferation. Inappropriate cell proliferation means cellular proliferation resulting from inappropriate cell growth, from excessive cell division, from cell division at an accelerated rate and/or from inappropriate cell survival.

In a further preferred embodiment the invention relates to the use according to the invention, wherein the disease is cancer selected from the group consisting of carcinomas, sarcomas, melanomas, myelomas, hematological neoplasias, lymphomas and childhood cancers.

Examples of carcinomas within the scope of the invention include but are not limited to adenocarcinoma (AC), squamous cell carcinoma (SCC) and mixed or undifferentiated carcinomas. Carcinomas within the scope of the invention include but are not limited to the following histologies:

Head and neck tumours: SCC, AC, transitional cell cancers, mucoepidermoid cancers, undifferentiated carcinomas;

Central nervous system tumours: Astrocytoma, glioblastoma, meningeoma, neurinoma, schwannoma, ependymoma, hypophysoma, oligodendroglioma, medulloblastoma;

Bronchial and mediastinal tumours:
Bronchial tumours:
Small cell lung cancers (SCLC): oat-cell lung cancer, intermediate cell cancer, combined oat-cell lung cancer;
Non-small cell lung cancers (NSCLC): SCC, spindle cell carcinoma, AC, bronchioalveolar carcinoma, large cell NSCLC, clear cell NSCLC;

Mesothelioma;
Thymoma;
Thyroid carcinomas: papillary, follicular, anaplastic, medullary;
Tumours of the gastrointestinal tract:
 Oesophageal cancers: SCC, AC, anaplastic, carcinoid, sarcoma;
 Gastric cancers: AC, adenosquamous, anaplastic;
 Colorectal cancers: AC, including hereditary forms of AC, carcinoid, sarcoma;
 Anal cancers: SCC, transitional epithelial cancer, AC, basal cell carcinoma;
 Pancreatic cancers: AC, including ductal and acinary cancers, papillary, adenosquamous, undifferentiated, tumours of the endocrine pancreas;
 Hepatocellular carcinoma, cholangiocarcinoma, angiosarcoma, hepatoblastoma;
 Biliary carcinomas: AC, SCC, small cell, undifferentiated;
 Gastrointestinal stroma tumours (GIST);
Gynaecological cancers:
 Breast cancers: AC, including invasive ductal, lobular and medullary cancers, tubular, mucinous cancers, Paget-carcinoma, inflammatory carcinoma, ductal and lobular carcinoma in situ;
 Ovarian cancers: Epithelial tumours, stroma tumours, germ cell tumours, undifferentiated tumours;
 Cervical cancers: SCC, AC, mixed and undifferentiated tumours;
 Endometrial cancers: AC, SCC, mixed, undifferentiated tumours;
 Vulvar cancers: SCC, AC;
 Vaginal cancers: SCC, AC;
Urinary tract and testicular cancers:
 Testicular cancers: seminoma;
 Non-seminomatous germ cell tumours: teratoma, embryonal cell carcinoma, choriocarcinoma, yolk sac tumour, mixed, Sertoli and Leydig-cell tumours;
 Extragonadal germ cell tumours;
 Prostate cancers: AC, small cell, SCC;
 Renal cell cancers: AC, including clear cell, papillary and chromophobous carcinomas, hereditary forms (e.g. von-Hippel-Lindau syndrome), nephroblastoma;
 Urinary bladder cancers: transitional cell (urothelial) cancers, SCC, AC;
 Urethral cancers: SCC, transitional cell cancers, AC;
 Penile cancers: SCC;
Tumours of endocrine tissue:
 Thyroid cancers: papillary, follicular, anaplastic, medullary carcinomas, including MEN syndrome;
 Tumours of the endocrine pancreas;
 Carcinoids;
 Adrenal tumours, e.g. Pheochromocytoma.
Examples of sarcomas within the scope of the invention include but are not limited to Ewing-sarcoma, osteosarcoma or osteogenic sarcoma, chondrosarcoma, synovial sarcoma, leiomyosarcoma, rhabdomyosarcoma, mesothelial sarcoma or mesothelioma, fibrosarcoma, angiosarcoma or hemangioendothelioma, liposarcoma, glioma or astrocytoma, myxosarcoma, malignant fibrous histiocytoma, mesenchymous or mixed mesodermal tumour, neuroblastoma and clear cell sarcoma.
Examples of skin tumors within the scope of the invention include but are not limited to basal cell carcinoma, Merkel cell carcinoma, sebaceous carcinoma, fibroxanthoma, malignant fibrous histiocytoma, and skin sarcoma.

Examples of melanomas within the scope of the invention include but are not limited to superficial spreading melanoma, nodular and lentigo-maligna melanoma.
Examples of myelomas within the scope of the invention include but are not limited to immunocytoma, plasmocytoma and multiple myeloma.
Examples of childhood cancers within the scope of the invention include but are not limited to Wilms' tumor, neuroblastoma, retinoblastoma, rhabdomyosarcoma, Ewing's sarcoma and peripheral primitive neuroectodermal tumors, germ cell tumors and childhood lymphoma and leukemias.
In another preferred embodiment the invention relates to the use of a composition as defined hereinbefore, wherein the hematologic cancer is leukemia.
Further examples of hematologic neoplasias within the scope of the invention include but are not limited to acute or chronic leukemias of myeloid, erythroid or lymphatic origin, myelodysplastic syndromes (MDS) and myeloproliferative syndromes (MPS, such as chronic myelogenous leukemia, osteomyelofibrosis, polycythemia vera or essential thrombocythemia).
Examples of lymphomas within the scope of the invention include but are not limited to:
 Hodgkin-lymphoma;
 Non-Hodgkin-lymphomas: T- and B-cell lymphomas
  B-cell lymphomas:
   Low and intermediate grade: Chronic lymphocytic leukemia (CLL), prolymphocytic leukemia (PLL), small lymphocytic lymphoma, hairy cell leukemia, plasmacytoid lymphoma, mantle cell lymphoma, follicular lymphoma, marginal zone lymphoma including MALT-lymphoma;
   High grade: diffuse large B-cell lymphoma (DLBCL including immunoblastic and centroblastic variants), lymphoblastic, Burkitt's lymphoma;
  T-cell lymphomas:
   Low grade: T-CLL, T-PLL, Mycosis fungoides, Sezary-syndrome;
   High grade: Anaplastic large cell, T-immunoblastic and lymphoblastic.
In another preferred embodiment the invention relates to the use according to the invention, wherein the disease is cancer selected from the group consisting of mixed tumours, undifferentiated tumours and metastases thereof.
Examples of mixed tumours within the scope of the invention include but are not limited to adenosquamous carcinomas, mixed mesodermal tumours, carcinosarcomas and teratocarcinomas.
Examples of undifferentiated, other tumours or metastases thereof within the scope of the invention include but are not limited to undifferentiated tumours, carcinomas of unknown primary (CUP), metastases of unknown primary (MUP) and pheochromocytoma, carcinoids.
In a further embodiment the invention relates to the use of a composition as defined hereinbefore, for the preparation of a medicament for the treatment of autoimmune disorders selected from the group consisting of amyloidosis, systemic lupus erythematosus, rheumatoid arthritis, Crohn's disease, multiple sclerosis, systemic sclerosis (scleroderma), mixed connective tissue disease, Sjögren's syndrome, ankylosing spondylitis, autoimmune vasculitis, Behcet's syndrome, psoriasis, autoimmune arthritis, sarcoidosis and diabetes mellitus.
In a further embodiment the invention relates to the use of a pharmaceutical composition as defined hereinbefore for the preparation of a medicament for the treatment of further non-oncological diseases, such as diabetic retinopathy and rheumatoid arthritis.

In a further embodiment the invention relates to the use of a composition as defined hereinbefore wherein the composition according to the invention is administered orally, enterically, transdermally, intravenously, peritoneally or by injection, preferably intravenously.

In a further embodiment the invention relates to a pharmaceutical combination preparation kit for the treatment of diseases involving cell proliferation, migration or apoptosis of myeloma cells, or angiogenesis, comprising a therapeutically effective amount of a compound 1 of Formula (I) in accordance with the present invention, or a polymorph, hydrate, metabolite or pharmaceutically acceptable salt thereof, and at least a further chemotherapeutic or naturally occurring, semi-synthetic or synthetic therapeutic agent 2, and optionally adapted for a co-treatment with radiotherapy or radio-immunotherapy, characterised in that the compound 1 of Formula (I) is comprised within a first compartment and the further chemotherapeutic or naturally occurring, semi-synthetic or synthetic therapeutic agent 2 is comprised within a second compartment, such that the administration to a patient in need thereof can be simultaneous, separate or sequential.

In a preferred embodiment the invention relates to a pharmaceutical combination preparation kit, wherein the formulation of the compound 1 of Formula (I) in accordance with the present invention is for oral administration or injection.

In a further embodiment the invention relates to the use of a pharmaceutical combination or a pharmaceutical combination preparation kit, for the manufacture of a medicament, optionally adapted for a co-treatment with radiotherapy or radio-immunotherapy, to treat diseases involving cell proliferation, migration or apoptosis of cancer cells, or angiogenesis, in a human or non-human mammalian body.

In a further embodiment the invention relates to the use of an effective amount of a compound 1 of Formula (I) or a polymorph, hydrate, metabolite or pharmaceutically acceptable salt thereof, in combination with at least a further chemotherapeutic or naturally occurring, semi-synthetic or synthetic therapeutic agent 2, for the manufacture of a pharmaceutical combination preparation, optionally adapted for a co-treatment with radiotherapy or radio-immunotherapy, for simultaneous, separate or sequential use in the treatment of diseases involving cell proliferation, migration or apoptosis of cancer cells, or angiogenesis, in a human or non-human mammalian body.

In a further embodiment the invention relates to a method for the treatment of diseases involving cell proliferation, migration or apoptosis of cancer cells, or angiogenesis, which method comprises simultaneous, separate or sequential co-administration of effective amounts of:
  (i) a compound 1 of Formula (I) or a polymorph, metabolite, hydrate, solvate, an individual optical isomer, mixtures of the individual enantiomers or racemates thereof, or a pharmaceutically acceptable salt thereof, and
  (ii) at least a further chemotherapeutic or naturally occurring, semi-synthetic or synthetic therapeutic agent 2;
in the form of a combined preparation optionally adapted for a co-treatment with radiotherapy or radio-immunotherapy, to a person in need of such treatment.

In a further embodiment the invention relates to the uses described above, characterised in that a compound 1 of Formula (I), or its polymorph, metabolite, hydrate, solvate, an individual optical isomer, mixtures of the individual enantiomers or racemates thereof or a pharmaceutically acceptable salt thereof, is administered intermittent or in a daily dosage such that the plasma level of the active substance lies between 10 and 5000 nM for at least 12 hours of the dosing interval.

The term "therapeutically effective amount" shall mean that amount of a drug or pharmaceutical agent that will elicit the biological or medical response of a tissue, system, animal or human that is being sought by a researcher or clinician.

As used herein, the term "composition" is intended to encompass a product comprising the specified ingredients in the specified amounts, as well as any product which results, directly or indirectly, from a combination of the specified ingredients in the specified amounts.

As already mentioned before, within the meaning of the present invention, the components 1 and 2 of the composition for a combination therapy may be administered separately (which implies that they are formulated separately) or together (which implies that they are formulated together). Hence, the administration of one element of the combination of the present invention may be prior to, concurrent to, or subsequent to the administration of the other element of the combination.

In accordance with the present invention, the elements of the combination of 1 and 2 may be administered by oral (including buccal or sublingual), enterical, parenteral (e.g., intramuscular, intraperitoneal, intravenous, transdermal or subcutaneous injection, or implant), nasal, vaginal, rectal, or topical (e.g. ocular eyedrops) routes of administration and may be formulated, alone or together, in suitable dosage unit formulations containing conventional non-toxic pharmaceutically acceptable carriers, adjuvants and vehicles appropriate for each route of administration.

In a preferred embodiment the element 1 of the combination in accordance with the invention is administered orally, enterically, transdermally, intravenously, peritoneally or by injection, preferably intravenously.

The pharmaceutical compositions for the administration of the components 1 and 2 of this invention may conveniently be presented in dosage unit form and may be prepared by any of the methods well known in the art of pharmacy. All methods include the step of bringing the active ingredient into association with the carrier which is constituted of one or more accessory ingredients. In general, the pharmaceutical compositions are prepared by uniformly and intimately bringing the active ingredients into association with a liquid carrier or a finely divided solid carrier both, and then, if necessary, shaping the product into the desired dosage form. In the pharmaceutical compositions the active compounds are included in an amount sufficient to produce the desired pharmacologic effect.

The pharmaceutical compositions containing the active ingredients 1 and 2, separately or together, that are suitable for oral administration may be in the form of discrete units such as hard or soft capsules, tablets, troches or lozenges, each containing a predetermined amount of the active ingredients, or in the form of a dispersible powder or granules, or in the form of a solution or a suspension in an aqueous liquid or non-aqueous liquid, or in the form of syrups or elixirs, or in the form of an oil-in-water emulsion or a water-in-oil emulsion.

Dosage forms intended for oral use may be prepared according to any method known to the art for the manufacture of pharmaceutical formulations and such compositions.

The excipients used may be, for example: (a) inert diluents such as mannitol, sorbitol, calcium carbonate, pregelatinized starch, lactose, calcium phosphate or sodium phosphate; (b) granulating and disintegrating agents, such as povidone, copovidone, hydroxypropylmethylcellulose, corn starch, alginic acid, crospovidone, sodiumstarchglycolate, croscarmellose, or polacrilin potassium; (c) binding agents such as microcrystalline cellulose or acacia; and (d) lubricating agents such as magnesium stearate, stearic acid, fumaric acid or talc.

In some cases, formulations for oral use may be in the form of hard gelatin or HPMC (hydroxypropylmethylcellulose) capsules wherein the active ingredients 1 or 2, separately or together, is mixed with an inert solid diluent, for example pregelatinized starch, calcium carbonate, calcium phosphate or kaolin, or dispensed via a pellet formulation. They may also be in the form of soft gelatin capsules wherein the active ingredient is mixed with water or an oil medium, for example peanut oil, liquid paraffin, medium chain triglycerides or olive oil.

The tablets, capsules or pellets may be uncoated or they may be coated by known techniques to delay disintegration and absorption in the gastrointestinal tract and thereby provide a delayed action or sustained action over a longer period. For example, a time delay material such as celluloseacetate phthalate or hydroxypropylcellulose acetate succinate or sustained release material such as ethylcellulose or ammoniomethacrylate copolymer (type B) may be employed.

Liquid dosage forms for oral administration in accordance with the present invention include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, perfuming and preserving agents.

Aqueous suspensions in accordance with the present invention normally contain the active materials 1 and 2, separately or together, in admixture with excipients suitable for the manufacture of aqueous suspensions. Such excipients may be (a) suspending agents such as hydroxy ethylcellulose, sodium carboxymethylcellulose, methylcellulose, hydroxypropylmethylcellulose, sodium alginate, polyvinylpyrrolidone, gum tragacanth and gum acacia; (b) dispersing or wetting agents which may be (b.1) a naturally-occurring phosphatide such as lecithin, (b.2) a condensation product of an alkylene oxide with a fatty acid, for example, polyoxyethylene stearate, (b.3) a condensation product of ethylene oxide with a long chain aliphatic alcohol, for example heptadecaethyleneoxycetanol, (b.4) a condensation product of ethylene oxide with a partial ester derived from a fatty acid and a hexitol such as polyoxyethylene sorbitol monooleate, or (b.5) a condensation product of ethylene oxide with a partial ester derived from a fatty acid and a hexitol anhydride, for example polyoxyethylene sorbitan monooleate.

The aqueous suspensions may also contain: one or more preservatives, for example, ethyl or n-propyl p-hydroxybenzoate; one or more coloring agents; one or more flavoring agents; and one or more sweetening agents, such as sucrose or saccharin.

Oily suspensions in accordance with the present invention may be formulated by suspending the active ingredients 1 and 2, separately or together, in a vegetable oil, for example arachis (peanut) oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable formulations for the preparation of an aqueous suspension in accordance with the present invention. In these formulations the active ingredients 1 and 2 are present, separately or together, in admixture with a dispersing or wetting agent, a suspending agent and one or more preservatives. Suitable examples of dispersing or wetting agents, suspending agents and preservatives are those already mentioned hereinbefore. Additional excipients such as, for example, sweetening, flavouring and colouring agents may also be present. Suitable examples of excipients are those already mentioned hereinbefore.

The pharmaceutical compositions of the invention may also be in the form of oil-in-water emulsions. The oily phase may be a vegetable oil such as olive oil or arachis (peanut) oil, or a mineral oil such as liquid paraffin or a mixture thereof.

Suitable emulsifying agents may be (a) naturally-occurring gums such as gum acacia and gum tragacanth, (b) naturally-occurring phosphatides such as soybean and lecithin, (c) esters or partial esters derived from fatty acids and hexitol anhydrides, for example sorbitan monooleate, (d) condensation products of said partial esters with ethylene oxide, for example polyoxyethylene sorbitan monooleate. The emulsions may also contain sweetening and flavouring agents.

Syrups and elixirs in accordance with the present invention may be formulated with sweetening agents, for example glycerol, propylene glycol, sorbitol or sucrose. Such formulations may also contain a preservative and flavoring and coloring agents. The pharmaceutical compositions containing 1 and 2, separately or together, may be in the form of a sterile injectable aqueous or oleagenous suspension or solution. The suspension may be formulated according to known methods using those suitable dispersing or wetting agents and suspending agents which have been mentioned hereinbefore. A suitable sterile injectable preparation may also be a sterile injectable solution or suspension in a non toxic parenterally-acceptable diluent or solvent, for example a solution in 1,3-butane-diol. Examples of suitable acceptable vehicles and solvents that may be employed are water, Ringer's solution and an isotonic sodium chloride solution. In addition, sterile, fixed oils may conventionally be employed as a solvent or suspending medium. For this purpose any bland fixed oil may be employed, including synthetic mono- or diglycerides. In addition, fatty acids such as oleic acid find use in the preparation of injectables in accordance with the present invention.

Preparations for parenteral administration according to the present invention containing 1 and 2, separately or together, include sterile aqueous or non-aqueous solutions, suspension, or emulsions.

Examples of suitables non-aqueous solvents or vehicles for the preparations in accordance with the present invention are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, by filtration through a bacteria-retaining filter, by incorporating sterilizing agents into the compositions, by irradiating the compositions, or by heating the compositions. They may also be manufactured in the form of sterile solid compositions which can be reconstituted in sterile water, or some other sterile injectable medium immediately before use.

The elements 1 and 2 of the combination of this invention may also be administered in the form of suppositories for rectal administration. Such compositions can be prepared by mixing the active ingredient with a suitable non-irritating excipient which is solid at ordinary temperatures but liquid at the rectal temperature and will therefore melt in the rectum to release the active ingredient. Such materials are cocoa butter, hard fat, and polyethylene glycols.

Compositions for buccal, nasal or sublingual administration in accordance with the present invention may be prepared with standard excipients well known in the art.

For topical administration, the elements 1 and 2 of the combination of this invention may be formulated, separately or together, in liquid or semi-liquid preparations. Examples of suitable preparations are: liniments, lotions, applications; oil-in-water or water-in-oil emulsions such as creams, ointments, jellies or pastes, including tooth-pastes; solutions or suspensions such as drops.

The dosage of the active ingredients in the compositions in accordance with the present invention may be varied, although the amount of the active ingredients 1 and 2 shall be such that a suitable dosage form is obtained. Hence, the selected dosage and the selected dosage form shall depend on the desired therapeutic effect, the route of administration and the duration of the treatment. Suitable dosage ranges for the combination are from the maximal tolerated dose for the single agent to lower doses, e.g. to one tenth of the maximal tolerated dose.

In the following, the present invention is illustrated via examples of pharmaceutical compositions comprising a compound 1 of chemical structure (I) in combination with one of the aforementioned combination partners 2, and by in vivo combination studies showing the potency of the combination to inhibit the proliferation and/or to induce the apoptosis of tumour cells. In these examples, the compound 1 of chemical structure (I) is 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide, which is a compound of Formula (I) according to the invention (Exemplified compound Nr. 46 in Table 1).

Combination of Exemplified Compound Nr. 46 of Table 1 and Irinotecan (HCT 116 Colon Cancer Model Combination Study)

Objective of the Study

Exemplified compound Nr. 46 of Table 1 is a potent and selective inhibitor of the serine/threonine kinase PLK-1, irinotecan (sold under the Trade name Campto®) is a standard chemotherapeutic agent for treatment of colorectal carcinomas. Previous studies have shown that exemplified compound Nr. 46 of Table 1 and irinotecan are active on HCT 116 derived tumors in nude mice. The goal of the present study was to assess the anti-cancer efficacy of suboptimal doses of exemplified compound Nr. 46 of Table 1, irinotecan and the combination of exemplified compound Nr. 46 of Table 1 and irinotecan, in the human colon carcinoma model HCT 116 grown as xenograft in nude mice. Suboptimal doses of both compounds were used to facilitate the detection of additive, synergistic or antagonistic effects.

Design of the Study

Model: Human colon carcinoma model HCT 116 grown as subcutaneous xenografts in nude mice.

Treatment groups (10 animals per group):

Controls Vehicle, i.v., once weekly for 6 weeks ((q7d)×6)

Exemplified compound Nr. 46 of Table 1
30 mg/kg, i.v., once weekly for 10 weeks ((q7d)×10)

Irinotecan 12.5 mg/kg, i.p., once weekly for 10 weeks ((q7d)×10)

Combination 30 mg/kg exemplified compound Nr. 46 of Table 1, i.v., once weekly for 10 weeks ((q7d)×10) and 12.5 mg/kg irinotecan, i.p., once weekly (~1 h after exemplified compound Nr. 46 of Table 1) for 10 weeks ((q7d)×10)

Tumor volumes and animal weights were recorded 3 times per week. Evaluation of therapy results was based on the absolute volumes of individual tumors.

Material and Methods:

Mice were female BomTac:NMRI-nu/nu. Exemplified compound Nr. 46 of Table 1 was dissolved in hydrochloric acid (0.1 N) diluted with 0.9% NaCl and injected intravenously into the tail vein, irinotecan infusion concentrate was diluted with 0.9% NaCl and injected intraperitoneally. The administration volume was 10 ml per kg body weight for both compounds. HCT 116 tumors were established from cultured HCT 116 cells. Tumor volumes were determined three times a week using a caliper. The weight of mice was determined as an indicator of tolerability on the same days. Plasma samples were taken on the last treatment day.

Main Results (See FIGS. 1.1-1.3)

BRIEF DESCRIPTION OF THE FIGURES

FIG. 1.1

HCT 116 tumor responses to treatment with 30 mg/kg exemplified compound Nr. 46 of Table 1, 12.5 mg/kg irinotecan or both.

HCT 116 tumor-bearing mice were treated intravenously with 30 mg/kg exemplified compound Nr. 46 of Table 1 once weekly ((q7d)×10), with 12.5 mg/kg irinotecan once weekly ((q7d)×10), with both in parallel ((q7d)×10) or once weekly with the vehicle only, and median tumor volumes were plotted over time. Day 1 was the first day, day 64 the last day of treatment and day 121 the final day of the study. The triangles indicate the treatment days.

FIG. 1.2

Days until HCT 116 tumors reach 1000 mm$^3$ in volume.

HCT 116 tumor-bearing mice were treated with 30 mg/kg exemplified compound Nr. 46 of Table 1 i.v. once weekly ((q7d)×10), with 12.5 mg/kg irinotecan i.p. once weekly ((q7d)×10), or a combination of both compounds ((q7d)×10) at respective doses. Vehicle treated mice (once weekly) were used as controls. Individual days until HCT 116 tumors reach 1000 mm$^3$ in volume were plotted. Each symbol represents one individual tumor. The horizontal lines represent the mean days.

FIG. 1.3

Change of body weight in response to treatment with 30 mg/kg exemplified compound Nr. 46 of Table 1, 12.5 mg/kg irinotecan or both. HCT 116 tumor-bearing mice were treated intravenously with 30 mg/kg exemplified compound Nr. 46 of Table 1 once weekly ((q7d)×10), with 12.5 mg/kg irinotecan once weekly ((q7d)×10), with both in parallel ((q7d)×10) or once weekly with the vehicle only and average changes of body weight were plotted over time. Day 1 was the first day, day 64 the last day of treatment and day 121 the final day of the study. The triangles indicate the treatment days. The triangles indicate the treatment days.

Results on Day 39 (End of the Controls):

30 mg/kg exemplified compound Nr. 46 of Table 1 i.v. significantly delays HCT 116 tumor growth (T/C=20%, p<0.001)

12.5 mg/kg irinotecan i.p. significantly delays tumor growth (T/C=25%, p<0.001)

Combined administration of 30 mg/kg exemplified compound Nr. 46 of Table 1 and of 12.5 mg/kg irinotecan significantly delays tumor growth (T/C=8%, p<0.001).

30 mg/kg exemplified compound Nr. 46 of Table 1, 12.5 mg/kg irinotecan and their combination are well tolerated. Control mice gained 10.3% body weight. Mice treated with 30 mg/kg exemplified compound Nr. 46 of Table 1 showed 8.6% body weight increase, mice treated with 12.5 mg/kg irinotecan gained 5.9% body weight in average, and mice treated with the combination gained 5.5. % body weight.

Results on Day 121 (End of the Study):

Weekly treatment (until day 64) with exemplified compound Nr. 46 of Table 1, irinotecan or a combination thereof delays the average time to reach 1000 mm$^3$ in tumor volume for 33.7 days, 35.1 days or 56.0 days, respectively.

CONCLUSIONS

A treatment with suboptimal doses of exemplified compound Nr. 46 of Table 1 or irinotecan significantly delays tumor growth and is well tolerated.

Treatment with the combination of suboptimal doses of exemplified compound Nr. 46 of Table 1 and irinotecan shows a significant growth delay and a higher efficacy than either of the compounds alone, without a decrease in tolerability.

The comparison of the growth delay (time until 1000 mm$^3$ in tumor size) shows an additive/synergistic effect.

Combination of Exemplified Compound Nr. 46 of Table 1 and Docetaxel
(NCI-H460 Lung Model)
Objective of the Study Exemplified compound Nr. 46 of Table 1 is a potent and selective inhibitor of the PLK1 serine/threonine kinase. Docetaxel (sold under the Trade Name Taxotere®) is a standard chemotherapeutic agent for treatment of lung cancer. Previous studies have shown that exemplified compound Nr. 46 of Table 1 is active on nude mice xenografts derived from the human lung cancer cell line NCI-H460. The goal of the present study was to assess the anti-cancer effects of suboptimal doses of exemplified compound Nr. 46 of Table 1 and docetaxel on NCI-H460 tumor growth when administered alone or in combination. Suboptimal doses of both compounds were used to facilitate the detection of additive, synergistic or antagonistic effects.

Design of the Study

Model: Human non-small cell lung carcinoma model NCI-H460 grown as subcutaneous xenografts in nude mice.

Treatment groups (intravenous administration, 10 animals per group):
Controls Vehicle, once weekly for 4 weeks ((q7d)×4)
Exemplified compound Nr. 46 of Table 1
50 mg/kg, once weekly for 4 weeks ((q7d)×4)
Docetaxel 15 mg/kg, once weekly for 4 weeks ((q7d)×4)
Combination 50 mg/kg exemplified compound Nr. 46 of Table 1, once weekly for 4 weeks ((q7d)×4) and 15 mg/kg Docetaxel, once weekly (3 days after exemplified compound Nr. 46 of Table 1) for 4 weeks ((q7d)×4)

Tumor volumes and animal weights were recorded 3 times per week. Evaluation of therapy results was based on the absolute volumes of individual tumors.

Material and Methods:

Mice were female BomTac:NMRI-nu/nu. Exemplified compound Nr. 46 of Table 1 was dissolved in hydrochloric acid (0.1 N) diluted with 0.9% NaCl and injected intravenously into the tail vein. Docetaxel infusion concentrate was diluted with 0.9% NaCl and injected intravenously. The administration volume was 10 ml per kg body weight. NCI-H460 tumors were established from cultured NCI-H460 cells. Tumor volumes were determined three times a week using a caliper. The weight of mice was determined as an indicator of tolerability on the same days. Plasma samples were taken on the last treatment day.

Main Results (See FIGS. 2.1-2.3)

BRIEF DESCRIPTION OF THE FIGURES

FIG. 2.1

NCI-H460 tumor responses to treatment with 50 mg/kg exemplified compound Nr. 46 of Table 1, 15 mg/kg Docetaxel or both.

NCI-H460 tumor-bearing mice were treated intravenously with 50 mg/kg exemplified compound Nr. 46 of Table 1 once weekly ((q7d)×4), with 15 mg/kg Docetaxel once weekly ((q7d)×4), with both in parallel or once weekly with the vehicle only, and median tumor volumes were plotted over time. Day 1 was the first day, day 25 the last day of treatment and day 43 the last day of the calculation of the median tumor volume. The triangles indicate the treatment days.

FIG. 2.2

Days until NCI-H460 tumors reach 1000 mm$^3$ in volume.

NCI-H460 tumor-bearing mice were treated with 50 mg/kg exemplified compound Nr. 46 of Table 1 i.v. once weekly ((q7d)×4), with 15 mg/kg Docetaxel i.v. once weekly ((q7d)×4), or a combination of both compounds at the same doses. Vehicle treated mice (once weekly) were used as controls. Individual days until NCI-H460 tumors reach 1000 mm$^3$ in volume were plotted. Each symbol represents one individual tumor. The horizontal lines represent the median days.

FIG. 2.3

Change of body weight in response to treatment with 50 mg/kg exemplified compound Nr. 46 of Table 1, 15 mg/kg Docetaxel or both. NCI-H460 tumor-bearing mice were treated intravenously with 50 mg/kg exemplified compound Nr. 46 of Table 1 once weekly ((q7d)×4), with 15 mg/kg Docetaxel once weekly ((q7d)×4), with both in parallel or once weekly with the vehicle only and average changes of body weight were plotted over time. Day 1 was the first day, day 25 the last day of treatment and day 43 the last day of the calculation of the median body weights. The triangles indicate the treatment days.

Results on Day 17 (End of the Controls)

50 mg/kg exemplified compound Nr. 46 of Table 1 i.v. once weekly does not significantly delay NCI-H460 tumor growth (T/C=65%, p>0.05).

15 mg/kg Docetaxel i.v. once weekly significantly delays tumor growth (T/C=42%, p<0.05).

Combined administration of 50 mg/kg exemplified compound Nr. 46 of Table 1 and of 15 mg/kg Docetaxel significantly delays tumor growth (T/C=26%, p<0.001).

50 mg/kg exemplified compound Nr. 46 of Table 1 is well tolerated.

15 mg/kg Docetaxel administered alone or in combination is not well tolerated. Mice treated with 15 mg/kg Docetaxel on average lost 4.8% body weight until day 17. The combination of exemplified compound Nr. 46 of Table 1 and Docetaxel induced a body weight loss of 8.3. %.

Results Until Day 71 (End of the Study)

Weekly treatment (until day 25) with exemplified compound Nr. 46 of Table 1, Docetaxel or a combination thereof delays the average time to reach 1000 mm$^3$ in tumor volume for 4.0 days, 10.5 days or 28.0 days compared to the controls, respectively.

Mice treated with 15 mg/kg Docetaxel further lost body weight (up to 9.4% on day 24) and one mouse had to be euthanized due to severe loss of body weight. Mice treated simultaneously with exemplified compound Nr. 46 of Table 1 and Docetaxel further lost body weight (up to 10.4% on day 24) and two mice had to be euthanized due to severe loss of body weight.

CONCLUSIONS

A treatment with suboptimal doses of exemplified compound Nr. 46 of Table 1 does not significantly delay tumor growth (T/C=65%, p>0.05).

Docetaxel significantly delays tumor growth (T/C=42%, p<0.05).

A combination of exemplified compound Nr. 46 of Table 1 and Docetaxel shows a significant growth delay compared to the controls (T/C=26%, p<0.001). The difference to the single treatment with exemplified compound Nr. 46 of Table 1 is also significant (p<0.01), indicating that the two agents might act at least additively.

Combination of Exemplified Compound Nr. 46 of Table 1 and Gemcitabine
(BxPC-3 Pancreas Model)

Objective of the Study

Exemplified compound Nr. 46 of Table 1 is a potent and selective inhibitor of the serine/threonine kinase PLK1. Gemcitabine (sold under the Trade Name Gemzar®) is a standard chemotherapeutic agent for treatment of pancreatic adenocarcinomas. The goal of the present study was to assess the anti-cancer efficacy of suboptimal doses of exemplified compound Nr. 46 of Table 1, gemcitabine and their combination in the human pancreas adenocarcinoma model BxPC-3 grown as xenograft in nude mice. Suboptimal doses of both compounds were used to facilitate the detection of additive, synergistic or antagonistic effects.

Design of the Study

Model: Human adenocarcinoma model BxPC-3 grown as subcutaneous xenografts in nude mice.

Treatment groups (10 animals per group):
Controls Vehicle, i.v., once weekly for 4 weeks ((q7d)×4)
Exemplified compound Nr. 46 of Table 1 50 mg/kg, i.v., once weekly for 6 weeks ((q7d)×6)
Gemcitabine 100 mg/kg, i.p., once weekly for 6 weeks ((q7d)×6)
Combination 50 mg/kg exemplified compound Nr. 46 of Table 1, i.v., once weekly for 6 weeks ((q7d)×6) and 100 mg/kg gemcitabine, i.p., once weekly (~1 h after exemplified compound Nr. 46 of Table 1) for 6 weeks ((q7d)×6)

Tumor volumes and animal weights were recorded 3 times per week. Evaluation of therapy results was based on the absolute volumes of individual tumors.

Material and Methods:

Mice were female BomTac:NMRI-nu/nu. Exemplified compound Nr. 46 of Table 1 was dissolved in hydrochloric acid (0.1 N) diluted with 0.9% NaCl and injected intravenously into the tail vein. Gemcitabin infusion concentrate was diluted with 0.9% NaCl and injected intraperitoneally. The administration volume was 10 ml per kg body weight for both compounds. BxPC-3 tumours were established from cultured BxPC-3. Tumour volumes were determined three times a week using a caliper. The weight of mice was determined as an indicator of tolerability on the same days. Plasma samples were taken on the last treatment day.

Main Results (See FIGS. 3.1-3.2)

BRIEF DESCRIPTION OF THE FIGURES

FIG. 3.1

BxPC-3 tumor responses to treatment with 50 mg/kg exemplified compound Nr. 46 of Table 1, 100 mg/kg gemcitabine or both.

BxBC-3 tumor-bearing mice were treated intravenously with 50 mg/kg exemplified compound Nr. 46 of Table 1 once weekly ((q7d)×6), with 100 mg/kg gemcitabine once weekly ((q7d)×6), with both in parallel or once weekly with the vehicle only, and median tumour volumes were plotted over time. Day 1 was the first day, day 36 the last day of treatment and day 26 the last day of the calculation of the median tumour volume.

FIG. 3.2

Change of body weight in response to treatment with 50 mg/kg exemplified compound Nr. 46 of Table 1, 100 mg/kg gemcitabine or both.

BxPC-3 tumour-bearing mice were treated intravenously with 50 mg/kg exemplified compound Nr. 46 of Table 1 once weekly ((q7d)×6), with 100 mg/kg gemcitabine once weekly ((q7d)×6), with both in parallel or once weekly with the vehicle only and average changes of body weight were plotted over time. Day 1 was the first day, day 36 the last day of treatment and day 43 the last day of the calculation of the median body weights. The triangles indicate the treatment days.

Results on Day 26 (End of the Controls):

50 mg/kg exemplified compound Nr. 46 of Table 1 i.v. significantly delays HCT 116 tumour growth (T/C=28%).

100 mg/kg gemcitabine i.p. only marginally delays tumour growth (T/C=65%) Higher doses of gemcitabine were not tolerated.

A combined administration of 50 mg/kg exemplified compound Nr. 46 of Table 1 and of 100 mg/kg gemcitabine delays tumour growth to the same extend as exemplified compound Nr. 46 of Table 1 alone (T/C=24%).

50 mg/kg exemplified compound Nr. 46 of Table 1, 100 mg/kg gemcitabine and their combination were well tolerated. Control mice gained 6.2% body weight. Mice treated with 50 mg/kg exemplified compound Nr. 46 of Table 1 showed 8.2% body weight increase, mice treated with 100 mg/kg gemcitabine gained 8.8% in average and mice treated with the combination gained 8.5. % body weight.

Results on Day 43 (End of the Study):

Weekly treatment (until day 36) with exemplified compound Nr. 46 of Table 1 or a combination of exemplified compound Nr. 46 of Table 1 and gemcitabine delays the average time to reach 1000 mm$^3$ in tumour volume to the same extend. There is no significant difference between the two treatment groups.

CONCLUSIONS

Treatment with suboptimal doses of exemplified compound Nr. 46 of Table 1 significantly delays tumour growth and is tolerated well. In contrast, the maximal tolerated dose of gemcitabine does not result in significant anti-tumour activity.

Treatment with the combination of suboptimal doses of exemplified compound Nr. 46 of Table 1 and gemcitabine shows a comparable growth delay as exemplified compound Nr. 46 of Table 1 alone, indicating that the two agents do not act antagonistically in this model.

A process for the manufacture of exemplified compound Nr. 46 of Table 1, i.e. the compound 4-[[(7R)-8-cyclopentyl-7-ethyl-5,6,7,8-tetrahydro-5-methyl-6-oxo-2-pteridinyl] amino]-3-methoxy-N-(1-methyl-4-piperidinyl)-benzamide, is described in WO 03/20722 as well as in WO 04/76454, which are incorporated herein by reference.

However, for the sake of completeness, a process for the manufacture of the compound 4-[[(7R)-8-cyclopentyl-7-ethyl-5,6,7,8-tetrahydro-5-methyl-6-oxo-2-pteridinyl] amino]-3-methoxy-N-(1-methyl-4-piperidinyl)-benzamide is described as well hereinafter. This method is to be understood as an illustration of the invention without restricting it to the subject matter thereof.

Synthesis of 4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide For the synthesis, first of all an intermediate compound Z3 is prepared as described below.

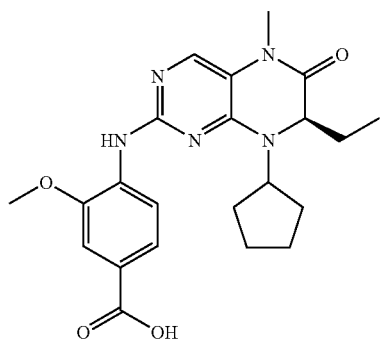

54.0 g (0.52 mol) D-2-aminobutyric acid are suspended in 540 mL methanol and slowly combined with 132 g (1.1 mol) thionyl chloride while cooling with ice. The mixture is refluxed for 1.5 h and then evaporated down. The oil remaining is combined with 540 mL tert-butylmethylether and the colourless crystals formed are suction filtered.

Yield: 78.8 g of a compound Z3a (colourless crystals)

74.2 g of the compound Z3a and 43.5 mL (0.49 mol) cyclopentanone are dissolved in 800 mL dichloromethane. After the addition of 40.0 g (0.49 mol) sodium acetate and 150.0 g (0.71 mol) sodium triacetoxyborohydride at 0° C. the mixture is stirred for 12 h at ambient temperature and then 500 mL of 20% sodium hydrogen carbonate solution are added. The aqueous phase is extracted with dichloromethane. The combined organic phases are washed with water, dried over $MgSO_4$ and evaporated down.

Yield: 85.8 g of a compound Z3b (light yellow oil)

40.0 g of the compound Z3b and 30.0 g (0.22 mol) potassium carbonate are suspended in 600 mL acetone and combined with 45.0 g (0.23 mol) 2,4-dichloro-5-nitropyrimidin in 200 mL acetone while cooling with ice. After 12 h a further 5.0 g 2,4-dichloro-5-nitropyrimidin are added and stirred for 3 h. The reaction mixture is evaporated down, taken up in 800 mL ethyl acetate and 600 mL water and the aqueous phase is extracted with ethyl acetate. The combined organic phases are washed with water, dried over $MgSO_4$ and evaporated down.

Yield: 75.0 g of a compound Z3c (brown oil)

100 g of the compound Z3c are dissolved in 650 mL glacial acetic acid and at 70° C. 20 g of iron powder are added batchwise. The mixture is stirred for 1 h at 70° C., then for 1.5 h at 100° C. and then filtered hot through diatomite (kieselguhr). The reaction mixture is evaporated down, taken up in methanol/dichloromethane, applied to silica gel and purified with ethyl acetate by Soxhlet extraction. The solvent is removed and the residue stirred with methanol.

Yield: 30.0 g of a compound Z3d (light brown crystals)

25.0 g of the compound Z3d and 6.5 mL (0.1 mol) methyl iodide are placed in 250 mL dimethylacetamide and at −10° C. 3.8 g (0.95 mol) sodium hydride as a 60% dispersion in mineral oil is added. It is stirred for 20 min at 0° C., then for 30 min at ambient temperature and finally ice is added. The reaction mixture is evaporated down and combined with 300 mL water. The precipitate formed is suction filtered and washed with petroleum ether.

Yield: 23.0 g of a compound Z3e (colourless solid)

6.0 g of the compound Z3e and 5.1 g (31 mmol) 4-amino-3-methoxybenzoic acid are suspended in 90 mL ethanol and 350 mL water, combined with 3.5 mL concentrated hydrochloric acid and refluxed for 48 h. The reaction mixture is evaporated down, the residue stirred with methanol/diethyl ether and the precipitate formed is suction filtered.

Yield: 6.3 g of a compound Z3 (light beige crystals)

4-[[(7R)-8-cyclopentyl-7-ethyl-5,6,7,8-tetrahydro-5-methyl-6-oxo-2-pteridinyl]amino]-3-methoxy-N-(1-methyl-4-piperidinyl)-benzamide is obtained as described below.

0.15 g of the compound Z3, 0.12 g TBTU, 0.12 mL DIPEA are dissolved in 5 mL dichloromethane and stirred for 30 minutes at 25° C. Then 50 mg 1-methyl-4-aminopiperidin are added and the mixture is stirred for a further 2.5 hours at 25° C. The solution is then extracted with water and then evaporated down. The residue is dissolved in warm ethyl acetate and crystallised from ether and petroleum ether.

Yield: 0.025 g of white crystals. M.p.: 203° C. as the base.

All compounds of Formula (I) according to the invention may be prepared by the synthesis methods A described hereinafter, while the substituents of general Formula (A1) to (A9) have the meanings given hereinbefore. This method is to be understood as an illustration of the invention without restricting it to the subject matter thereof.

Method A

Step 1A

A compound of Formula (A1) is reacted with a compound of Formula (A2) to obtain a compound of Formula (A3) (Diagram 1A). This reaction may be carried out according to WO 00/43369 or WO 00/43372. Compound (A1) is commercially obtainable, for example, from City Chemical LLC, 139 Allings Crossing Road, West Haven, Conn., 06516, USA. Compound (A2) may be prepared by procedures known from the literature: (a) F. Effenberger, U. Burkhart, J. Willfahrt *Liebigs Ann. Chem.* 1986, 314-333; (b) T. Fukuyama, C.-K. Jow, M. Cheung, *Tetrahedron Lett.* 1995, 36, 6373-6374; (c) R. K. Olsen, *J. Org. Chem.* 1970, 35, 1912-1915; (d) F. E. Dutton, B. H. Byung *Tetrahedron Lett.* 1998, 30, 5313-5316; (e) J. M. Ranajuhi, M. M. Joullie *Synth. Commun.* 1996, 26, 1379-1384.).

Diagram 1A

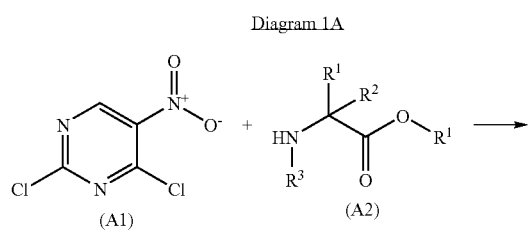

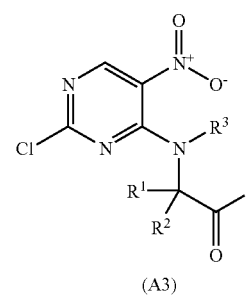

In Step 1A, 1 equivalent of the compound (A1) and 1 to 1.5 equivalents, preferably 1.1 equivalents of a base, preferably potassium carbonate, potassium hydrogen carbonate, sodium carbonate or sodium hydrogen carbonate, calcium carbonate, most preferably potassium carbonate, are stirred in a diluent optionally mixed with water, for example acetone, tetrahydrofuran, diethylether, cyclohexane, petroleum ether or dioxane, preferably cyclohexane or diethylether.

At a temperature of 0 to 15° C., preferably 5 to 10° C., 1 equivalent of an amino acid of Formula (A2), dissolved in an organic solvent, for example acetone, tetrahydrofurane, diethylether, cyclohexane or dioxane, is added dropwise. The reaction mixture is heated to a temperature of 18° C. to 30° C., preferably about 22° C., with stirring and then stirred for a further 10 to 24 hours, preferably about 12 hours. Then the diluent is distilled off, the residue is combined with water and the mixture is extracted two to three times with an organic solvent, such as diethylether or ethyl acetate, preferably ethyl acetate. The combined organic extracts are dried and the solvent is distilled off. The residue (compound A3) may be used in Step 2 without any prior purification.

Step 2A

The compound obtained in Step 1A (A3) is reduced at the nitro group and cyclised to form the compound of Formula (A4) (Diagram 2A).

Diagram 2A

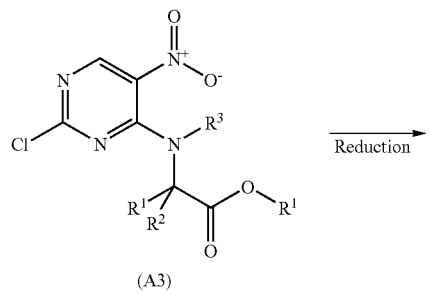

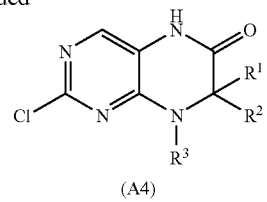

In Step 2A, 1 equivalent of the nitro compound (A3) is dissolved in an acid, preferably glacial acetic acid, formic acid or hydrochloric acid, preferably glacial acetic acid, and heated to 50 to 70° C., preferably about 60° C. Then a reducing agent, for example zinc, tin or iron, preferably iron filings, is added to complete the exothermic reaction and the mixture is stirred for 0.2 to 2 hours, preferably 0.5 hours, at 100 to 125° C., preferably at about 117° C. After cooling to ambient temperature the iron salt is filtered off and the solvent is distilled off. The residue is taken up in a solvent or mixture of solvents, for example ethyl acetate or dichloromethane/methanol 9/1 and semisaturated NaCl solution, and filtered through kieselgur, for example. The organic phase is dried and evaporated down. The residue (compound (A4)) may be purified by chromatography or by crystallisation or used as the crude product in Step 3A of the synthesis.

Step 3A

The compound obtained in Step 2A (A4) may be reacted by electrophilic substitution as shown in Diagram 3A to obtain the compound of Formula (A5).

Diagram 3A

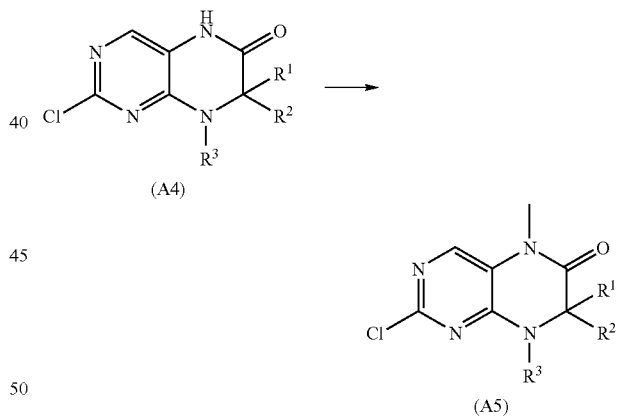

In Step 3A 1 equivalent of the amide of Formula (A4) is dissolved in an organic solvent, for example dimethylformamide or dimethylacetamide, preferably dimethylacetamide, and cooled to about −5 to 5° C., preferably 0° C.

Then 0.9 to 1.3 equivalents of sodium hydride and 0.9 to 1.3 equivalents of a methylating reagent, e.g. methyl iodide, are added. The reaction mixture is stirred for 0.1-3 hours, preferably about 1 hour, at about 0 to 10° C., preferably at about 5° C., and may optionally be left to stand for a further 12 hours at this temperature. The reaction mixture is poured onto ice water and the precipitate is isolated. The residue (compound (A5)) may be purified by chromatography, preferably over silica gel, or by crystallisation, or used as the crude product in step 4A of the synthesis.

Step 4A

The amination of the compound (A5) obtained in Step 3A to yield the compound of Formula (A9) (Diagram 4A) may be carried out using the methods known from the literature, for variants 4.1 A from e.g. (a) M. P. V. Boarland, J. F. W. McOmie *J. Chem. Soc.* 1951, 1218-1221 or (b) F. H. S. Curd, F. C. Rose *J. Chem. Soc.* 1946, 343-348, for variants 4.2 A from e.g. (a) Banks *J. Am. Chem. Soc.* 1944, 66, 1131, (b) Ghosh and Dolly *J. Indian Chem. Soc.* 1981, 58, 512-513 or (c) N. P. Reddy and M. Tanaka *Tetrahedron Lett.* 1997, 38, 4807-4810.

For example, in variant 4.2 A, 1 equivalent of the compound (A5) and 1 to 3 equivalents of the compound (A6) are stirred with acid, for example 1-10 equivalents of 10-38% hydrochloric acid and/or an alcohol, for example ethanol, propanol, butanol, preferably ethanol, at reflux temperature for 1 to 48 hours, preferably about 5 hours. The product precipitated (A9) is filtered off and optionally washed with water, dried and crystallised from a suitable organic solvent.

For example, in variant 4.3 A, 1 equivalent of the compound (A5) and 1 to 3 equivalents of the compound (A7) are dissolved in a solvent, for example toluene or dioxane and

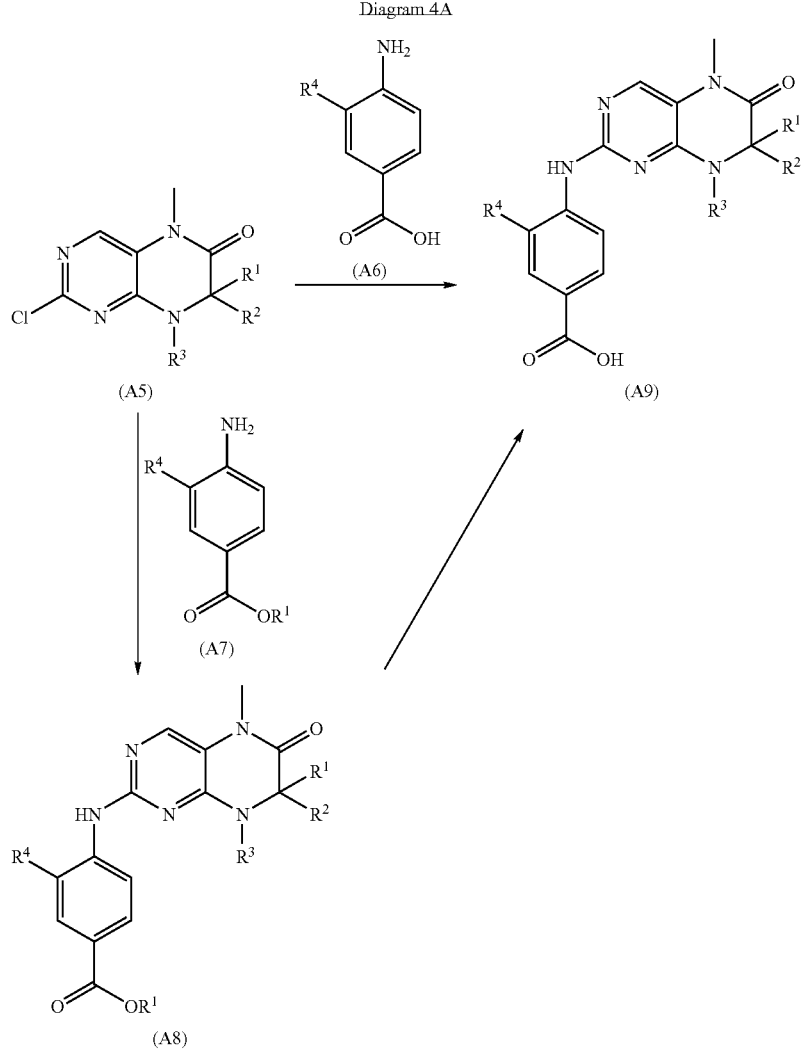

Diagram 4A

For example, in variant 4.1 A, 1 equivalent of the compound (A5) and 1 to 3 equivalents, preferably about 2 equivalents of the compound (A6) are heated without a solvent or in an organic solvent such as for example sulpholane, dimethylformamide, dimethylacetamide, toluene, N-methylpyrrolidone, dimethylsulphoxide or dioxane, preferably sulpholane, for 0.1 to 4 hours, preferably 1 hour, at 100 to 220° C., preferably at about 160° C. After cooling, the product (A9) is crystallised by the addition of organic solvents or mixtures of solvents, e.g. diethylether/methanol, ethyl acetate, methylene chloride, or diethylether, preferably diethylether/methanol 9/1, or purified by chromatography.

combined with a phosphine ligand, for example 2, 2'-bis-(diphenylphosphino)-1,1'-binaphthyl and a palladium catalyst, for example tris(dibenzylidene-acetone)-dipalladium(0) and a base, for example caesium carbonate, and refluxed for 1-24 h, preferably 17 h. The reaction mixture is purified for example over silica gel and the product (A8) is isolated from the solution or obtained by suitable crystallisation. The product (A8) is dissolved in a suitable solvent, for example dioxane and mixed with acid, for example semiconcentrated hydrochloric acid, for example in the ratio of solvent to acid of 3:1. Then the mixture is refluxed for 1-48 h, for example 12 h, and the precipitate formed is isolated. If desired the product (A9) is purified by crystallisation.

Step 5A

Diagram 5A

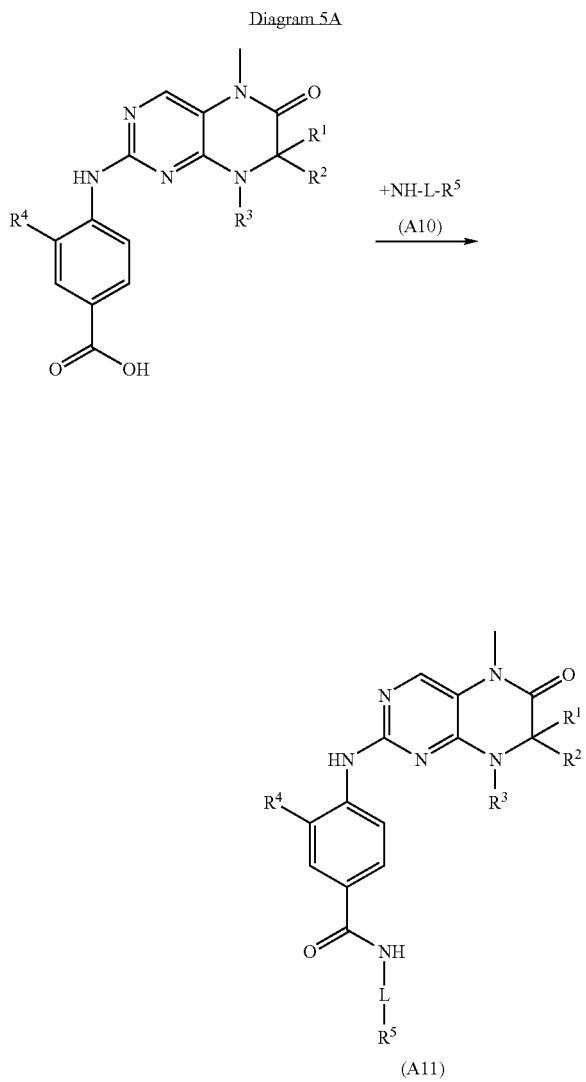

For example, 1 equivalent of the compound (A9) is dissolved with 1 equivalent of an activating reagent, e.g. O-benzotriazolyl-N,N,N',N'-tetramethyluronium tetrafluoroborate (TBTU) and a base, for example 1.5 equivalents of diisopropylethylamine (DIPEA) in an organic diluent, for example dichloromethane, tetrahydrofuran, dimethylformamide, N-methylpyrrolidone, dimethylacetamide, preferably dichloromethane or dimethylformamide. After the addition of 1 equivalent of the amine (A10) the reaction mixture is stirred for 0.1 to 24 hours, preferably about 2 hours at 20° C. to 100° C. The product of Formula (A11) is obtained for example by crystallisation or chromatographic purification.

The compounds of general Formula (I) may be synthesised analogously to the following examples of synthesis. The numbering of the Examples corresponds to the numbering used in Table 1. These Examples are, however, intended only as examples of procedures to illustrate the invention further, without restricting the invention to their subject matter.

The preparation of some intermediate compounds used to synthesise the compounds is also described hereinafter.

Preparation of the Acids

To synthesise the compounds of Examples 94 and 95 of Table 1, first an intermediate compound Z1

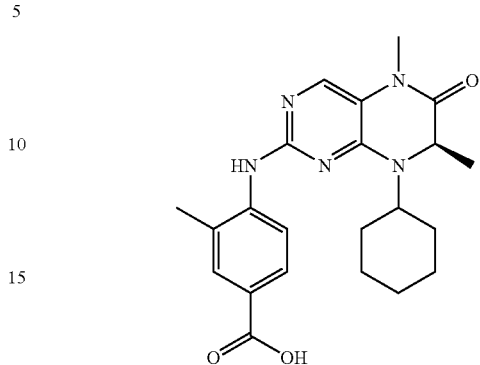

is prepared as described hereinafter.

50.0 g (0.48 mol) of D-alanine methyl ester×HCl and 49.1 g (0.50 mol) cyclohexanone are placed in 300 mL dichloromethane and then combined with 41.0 g (0.50 mol) sodium acetate and 159.0 g (0.75 mol) sodium triacetoxyborohydride. The mixture is stirred overnight and then 300 mL of 10% sodium hydrogen carbonate solution are added. The aqueous phase is extracted with dichloromethane. The combined organic phases are washed with 10% sodium hydrogen carbonate solution, dried over $Na_2SO_4$ and evaporated down.

Yield: 72.5 g of a compound Z1a (clear liquid)

72.5 g of the compound Z1a are placed in 500 mL water and 76.6 g (0.39 mol) of 2,4-dichloro-5-nitropyrimidine in 500 mL diethyl ether are added. At a temperature of −5° C. 100 mL 10% potassium hydrogen carbonate solution are added dropwise. The mixture is stirred for 3 h at −5° C. and for a further 12 h at ambient temperature. The organic phase is separated off and dried over $Na_2SO_4$. On evaporation, the product crystallizes out.

Yield: 48.0 g of a compound Z1b (yellow crystals)

48.0 g of the compound Z1b are dissolved in 350 mL glacial acetic acid and heated to 60° C. 47.5 g of iron powder are added, while the temperature rises to 105° C. The reaction mixture is stirred for three hours at 80° C., then filtered hot through cellulose and evaporated down. The residue is stirred in water and ethyl acetate, suction filtered and the light-grey precipitate is washed with ethyl acetate. The filtrate is washed with dilute ammonia and water, the organic phase is dried over $Na_2SO_4$, filtered through activated charcoal and evaporated down. Some more light-grey solids are obtained.

Yield: 29.5 g of a compound Z1c (light-grey crystals)

32.1 g of the compound Z1c are placed in 300 mL dimethylacetamide and combined with 13 mL (0.2 mol) methyl iodide. At −5° C. 6.4 g (0.16 mol) sodium hydride as a 60% dispersion in mineral oil is added batchwise. After 2 h the reaction mixture is poured onto 800 mL ice water. The precipitate formed is suction filtered and washed with petroleum ether.

Yield: 33.0 g of a compound Z1d (beige crystals)

4.0 g of the compound Z1d and 2.3 g (15 mmol) 4-amino-3-methylbenzoic acid are suspended in 50 mL ethanol and 120 mL water, combined with 2 mL concentrated hydrochloric acid and refluxed for 48 h. The precipitate formed on cooling is suction filtered and washed with water, ethanol and diethyl ether.

Yield: 2.9 g of a compound Z1 (colourless crystals)

To synthesise the compounds Example 188 and Example 203 of Table 1, first of all an intermediate compound Z2

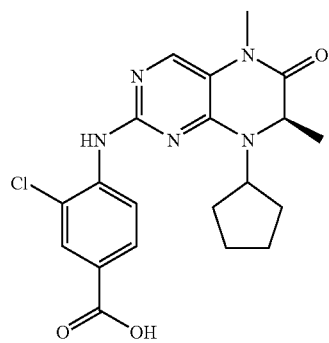

is prepared as described below.

A solution of 128.2 g (0.83 mol) D-alanine ethyl ester×HCl and 71.5 g (0.85 mol) cyclopentanone in 1500 mL dichloromethane is combined with 70.1 (0.85 mol) sodium acetate and 265.6 g (1.25 mol) sodium triacetoxyborohydride. The reaction mixture is stirred for 12 h and then poured into 1.5 L of a 10% sodium hydrogen carbonate solution. The aqueous phase is extracted with dichloromethane. The combined organic phases are dried over $Na_2SO_4$ and evaporated down.

Yield: 143.4 g of a compound Z2a (colourless oil)

66.0 g of the compound Z2a are placed in 500 mL water and combined with 85.0 g (0.44 mol) 2,4-dichloro-5-nitropyrimidine in 500 mL diethyl ether. At −5° C. 100 mL 10% potassium hydrogen carbonate solution are added dropwise and the reaction mixture is stirred for 48 h at ambient temperature. The aqueous phase is extracted with diethyl ether, the combined organic phases are dried over $Na_2SO_4$ and evaporated down. The dark red solid is stirred with petroleum ether and suction filtered.

Yield: 88.0 g of a compound Z2b (yellow crystals)

88.0 g of the compound Z2b are dissolved in 1000 mL glacial acetic acid and at 60° C. combined batchwise with 85 g iron powder, while the temperature rises to 110° C. It is stirred for 1 h at 60° C., then suction filtered hot through cellulose and evaporated down. The brown solid is stirred with 700 mL water and suction filtered.

Yield: 53.3 g of a compound Z2c (light brown crystals)

53.3 g of the compound Z2c are dissolved in 300 mL dimethylacetamide and combined with 13 mL (0.21 mol) methyl iodide. At −5° C. 5.0 g (0.21 mol) sodium hydride as a 60% dispersion in mineral oil are added batchwise. After 12 h the reaction mixture is poured onto 1000 mL ice water and the precipitate formed is suction filtered.

Yield: 40.0 g of a compound Z2d (colourless crystals)

4.0 g of the compound Z2d and 2.8 g (16 mmol) 4-amino-3-chlorobenzoic acid are suspended in 25 mL ethanol and 60 mL water, combined with 3 mL concentrated hydrochloric acid and refluxed for 43 h. The precipitate formed on cooling is suction filtered and washed with water, ethanol and diethyl ether.

Yield: 0.9 g of a compound Z2 (colourless crystals)

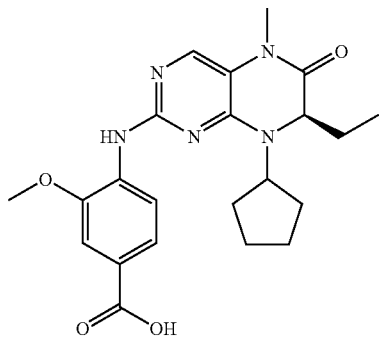

To synthesise the compounds of Examples 19, 21, 22, 23, 45, 46, 55, 58, 116, 128, 131, 133, 134, 136, 138, 177, 217, 231, 239, 46, 184, 166 and 187 of Table 1, first of all an intermediate compound Z3 is prepared as described below.

54.0 g (0.52 mol) D-2-aminobutyric acid are suspended in 540 mL methanol and slowly combined with 132 g (1.1 mol) thionyl chloride while cooling with ice. The mixture is refluxed for 1.5 h and then evaporated down. The oil remaining is combined with 540 mL tert-butylmethylether and the colourless crystals formed are suction filtered.

Yield: 78.8 g of a compound Z3a (colourless crystals)

74.2 g of the compound Z3a and 43.5 mL (0.49 mol) cyclopentanone are dissolved in 800 mL dichloromethane. After the addition of 40.0 g (0.49 mol) sodium acetate and 150.0 g (0.71 mol) sodium triacetoxyborohydride at 0° C. the mixture is stirred for 12 h at ambient temperature and then 500 mL of 20% sodium hydrogen carbonate solution are added. The aqueous phase is extracted with dichloromethane. The combined organic phases are washed with water, dried over $MgSO_4$ and evaporated down.

Yield: 85.8 g of a compound Z3b (light yellow oil)

40.0 g of the compound Z3b and 30.0 g (0.22 mol) potassium carbonate are suspended in 600 mL acetone and combined with 45.0 g (0.23 mol) 2,4-dichloro-5-nitropyrimidin in 200 mL acetone while cooling with ice. After 12 h a further 5.0 g 2,4-dichloro-5-nitropyrimidin are added and stirred for 3 h. The reaction mixture is evaporated down, taken up in 800 mL ethyl acetate and 600 mL water and the aqueous phase is extracted with ethyl acetate. The combined organic phases are washed with water, dried over $MgSO_4$ and evaporated down.

Yield: 75.0 g of a compound Z3c (brown oil)

100 g of the compound Z3c are dissolved in 650 mL glacial acetic acid and at 70° C. 20 g of iron powder are added batchwise. The mixture is stirred for 1 h at 70° C., then for 1.5 h at 100° C. and then filtered hot through kieselgur. The reaction mixture is evaporated down, taken up in methanol/dichloromethane, applied to silica gel and purified with ethyl acetate by Soxhlet extraction. The solvent is removed and the residue stirred with methanol.

Yield: 30.0 g of a compound Z3d (light brown crystals)

25.0 g of the compound Z3d and 6.5 mL (0.1 mol) methyl iodide are placed in 250 mL dimethylacetamide and at −10° C. 3.8 g (0.95 mol) sodium hydride as a 60% dispersion in mineral oil is added. It is stirred for 20 min at 0° C., then for 30 min at ambient temperature and finally ice is added. The reaction mixture is evaporated down and combined with 300 mL water. The precipitate formed is suction filtered and washed with petroleum ether.

Yield: 23.0 g of a compound Z3e (colourless solid)

6.0 g of the compound Z3e and 5.1 g (31 mmol) 4-amino-3-methoxybenzoic acid are suspended in 90 mL ethanol and 350 mL water, combined with 3.5 mL concentrated hydrochloric acid and refluxed for 48 h. The reaction mixture is evaporated down, the residue stirred with methanol/diethyl ether and the precipitate formed is suction filtered.

Yield: 6.3 g of a compound Z3 (light beige crystals)

To synthesise the compound of Examples 81, 82, 93 and 137 of Table 1, first of all an intermediate compound Z4

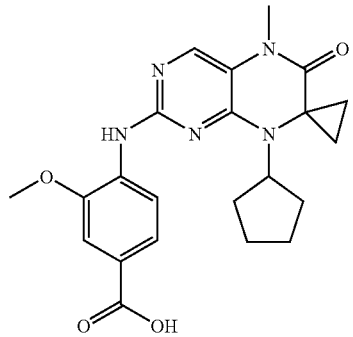

Z4 is prepared as described below.

25.0 g (0.19 mol) of ethyl-aminocyclopropane-1-carboxylate×HCl and 16.8 g (0.20 mol) of cyclopentanone are dissolved in 300 mL of dichloromethane and combined with 16.4 g (0.20 mol) of sodium acetate and 61.7 g (0.29 mol) of sodium triacetoxyborohydride. It is stirred overnight and the reaction mixture is then poured onto 400 mL of 10% sodium hydrogen carbonate solution. The aqueous phase is extracted with dichloromethane. The combined organic phases are dried over $Na_2SO_4$ and evaporated down.

Yield: 34.5 g of a compound Z4a (colourless oil)

42.5 g (0.22 mol) of 2,4-dichloro-5-nitropyrimidine in 350 mL of diethyl ether are added to a mixture of 34.5 g of the compound Z4a in 350 mL water. At −5° C. the mixture is combined with 80 mL 10% potassium hydrogen carbonate solution and stirred overnight at ambient temperature. The aqueous phase is extracted with diethyl ether. The combined organic phases are dried over $Na_2SO_4$ and evaporated down.

Yield: 53.8 g of a compound Z4b (brown oil)

20.1 g of the compound Z4b are dissolved in 200 mL glacial acetic acid and combined batchwise at 60° C. with 19.1 g iron powder, during which time the temperature rose to 100° C. The mixture is stirred for 3 h at 60° C., then suction filtered through cellulose and evaporated down. The residue is stirred in water and ethyl acetate and the yellow precipitate is suction filtered. The filtrate is washed with dilute ammonia and water, the organic phase dried over $Na_2SO_4$ and evaporated down. After the addition of diethyl ether additional product crystallised out.

Yield: 4.0 g of a compound Z4c (yellow crystals)

7.8 g of the compound Z4c and 2.6 mL (0.04 mol) methyl iodide are dissolved in 100 mL dimethylacetamide and at −5° C. 1.5 g (0.04 mol) sodium hydride are added batchwise as a 60% dispersion in mineral oil. After 2 h the reaction mixture is poured onto ice water and the precipitate formed is suction filtered.

Yield: 7.5 g of a compound Z4d (light brown crystals)

3.0 g of the compound Z4d and 1.9 g (11 mmol) 4-amino-3-methoxybenzoic acid are suspended in 40 mL ethanol and 80 mL water, combined with 2 mL concentrated hydrochloric acid and refluxed for 20 h. A further 0.5 g of 4-amino-3-methoxybenzoic acid are added and refluxed for 48 h. The precipitate formed on cooling is suction filtered and washed with water, ethanol and diethyl ether.

Yield: 2.1 g of a compound Z4 (colourless crystals) m.p.: 222-223° C.

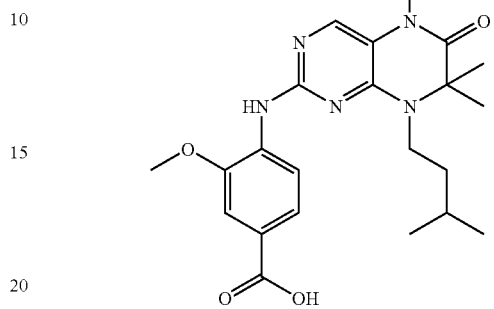

is prepared as described below.

To synthesise the compounds of Examples 162, 43, 53, 161, 202, 211, 215 and 212 of Table 1, first of all an intermediate compound Z5

A mixture of 73.4 mL (0.5 mol) ethyl 2-bromoisobutyrate, 87.1 mL (0.75 mol) of 3-methyl-1-butylamine, 82.5 g (0.6 mol) sodium iodide and 76.0 g (0.6 mol) of potassium carbonate in 1000 mL ethyl acetate is refluxed for 3 days. Any salts present are filtered off and the filtrate evaporated down.

Yield: 97.0 g of a compound Z5a (red oil)

49.0 g (0.25 mol) of 2,4-dichloro-5-nitropyrimidine and 38.3 g (0.28 mol) of potassium carbonate are suspended in 500 mL acetone and at 0° C. combined with 93.0 g of the compound Z5a in 375 mL acetone. The reaction mixture is stirred overnight at ambient temperature, filtered and evaporated down. The residue dissolved in ethyl acetate is washed with water and the organic phase dried over $MgSO_4$ and evaporated down.

Yield: 102.7 g of a compound Z5b (brown oil)

22.7 g of the compound Z5b are dissolved in 350 mL glacial acetic acid and at 60° C. combined batchwise with 17.4 g iron powder. After the addition ends the mixture is refluxed for 0.5 h, filtered hot and evaporated down. The residue is taken up in 200 mL dichloromethane/methanol (9:1) and washed with sodium chloride solution. The organic phase is suction filtered through kieselguhr, dried over $MgSO_4$, evaporated down and purified by column chromatography (eluant: ethyl acetate/cyclohexane 1:1).

Yield: 1.9 g of a compound Z5c (colourless crystals)

1.9 g of the compound Z5c are dissolved in 32 mL dimethylacetamide and while cooling with ice combined with 0.3 g (7 mmol) sodium hydride as a 60% dispersion in mineral oil. After 10 min 0.5 mL (7 mmol) methyl iodide are added and stirred for 3 h at ambient temperature. The reaction mixture is evaporated down and combined with water. The precipitate formed is suction filtered and washed with petroleum ether.

Yield: 1.6 g of a compound Z5d (colourless crystals)

14.0 g of the compound Z5d and 10.0 g (0.06 mol) 4-amino-3-methoxybenzoic acid are suspended in 200 mL dioxane and 80 mL water, combined with 10 mL concentrated hydrochloric acid and refluxed for 40 h. The precipitate formed on cooling is suction filtered and washed with water, dioxane and diethyl ether.

Yield: 13.9 g of a compound Z5 (colourless crystals)

To synthesise the compounds of Examples 88, 194, 229 and 89 of Table 1, first of all an intermediate compound Z6

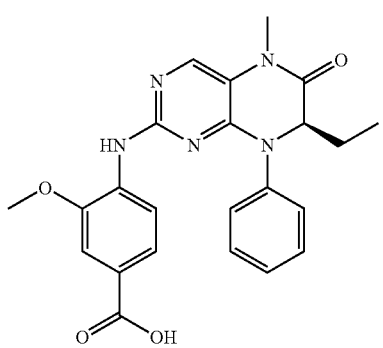

is prepared as described below.

6.0 g (0.06 mol) L-2-aminobutyric acid is placed in 80 mL 0.5 M sulphuric acid and at 0° C. combined with 5.5 g (0.08 mol) sodium nitrite in 15 mL water. The reaction mixture is stirred for 22 h at 0° C., combined with ammonium sulphate and filtered. The filtrate is extracted with diethyl ether and the combined organic dried over MgSO$_4$ and evaporated down.

Yield: 6.0 g of a compound Z6a (yellow oil)

200 mL methanol are combined successively with 65.0 mL (0.89 mol) thionyl chloride and 76.0 g of the compound Z6a in 50 mL methanol while cooling with ice. The resulting mixture is stirred for 1 h at 0° C. and 2 h at ambient temperature and then the methanol and remaining thionyl chloride are eliminated in vacuo at 0° C.

Yield: 40.0 g of a compound Z6b (yellow oil)

30.0 mL (0.17 mol) of trifluoromethanesulphonic acid anhydride are placed in 150 mL dichloromethane and while cooling with ice a solution of 20.0 g of the compound Z6b and 14.0 mL (0.17 mol) pyridine in 50 mL dichloromethane is added within one hour. The mixture is stirred for 2 h at ambient temperature, any salts formed are suction filtered and then washed with 100 mL water. The organic phase is dried over MgSO$_4$ and evaporated down.

Yield: 42.0 g of a compound Z6c (light yellow oil)

42.0 g of the compound Z6c in 200 mL dichloromethane is added dropwise within one hour to a solution of 15.5 mL (0.17 mol) of aniline and 24.0 mL (0.17 mol) of triethylamine in 400 mL dichloromethane while cooling with ice. The mixture is stirred for 1 h at ambient temperature and a further 2 h at 35° C. The reaction mixture is washed with water, dried over MgSO$_4$ and evaporated down. The residue remaining is purified by distillation (95-100° C., 1*10$^{-3}$ mbar).

Yield: 14.0 of a compound Z6d (colourless oil)

14.0 g of the compound Z6d and 16.0 g (0.1 mol) potassium carbonate are suspended in 100 mL acetone and at 10° C. combined with 16.0 g (0.08 mol) of 2,4-dichloro-5-nitropyrimidine. The mixture is stirred for 4 h at 40° C., any salts formed are suction filtered and the filtrate evaporated down. The residue is taken up in 300 mL ethyl acetate and washed with water. The organic phase is dried over MgSO$_4$ and evaporated down.

Yield: 31.0 g of a compound Z6e (brown oil)

31.0 g of the compound Z6e are dissolved in 200 mL glacial acetic acid and at 60° C. combined batchwise with 10 g iron powder, during which time the temperature rose to 85° C. The mixture is stirred for a further hour at 60° C., filtered through kieselguhr and evaporated down. The residue is stirred with methanol.

Yield: 4.5 g of a compound Z6f (brown crystals)

At −20° C. 0.6 g (16 mmol) of sodium hydride as a 60% dispersion in mineral oil are added batchwise to a mixture of 4.5 g of the compound Z6f and 1.0 mL (16 mmol) methyl iodide in 100 mL dimethylacetamide. After 1 h the reaction mixture is combined with 50 mL water and evaporated down. The residue is stirred with 200 mL water, the precipitate is suction filtered and washed with petroleum ether.

Yield: 4.5 g of a compound Z6g (colourless crystals)

A suspension of 1.5 g of the compound Z6g and 1.4 g (8 mmol) of methyl 4-amino-3-methoxybenzoate in 30 mL toluene is combined with 0.4 g (0.6 mmol) of 2,2'-bis-(diphenylphosphino)-1,1'-binaphthyl, 0.23 g (0.3 mmol) of tris(dibenzylideneacetone)-dipalladium(0) and 7.0 g (21 mmol) of caesium carbonate and refluxed for 17 h. The reaction mixture is applied to silica gel and purified by column chromatography (eluant:dichloromethane/methanol 9:1).

Yield: 1.7 g of a compound Z6h (yellow crystals)

1.7 g of the compound Z6h are dissolved in 50 mL dioxane, combined with 15 mL of semiconcentrated hydrochloric acid and refluxed for 12 h. After cooling the precipitate formed is suction filtered.

Yield: 1.1 g of a compound Z6 (colourless solid)

To synthesise the compounds of Examples 26, 20, 32, 56, 101, 112 and 209 of Table 1, first of all an intermediate compound Z7

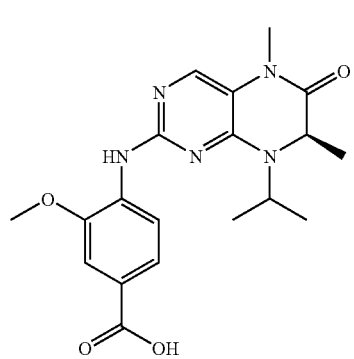

is prepared as described below.

50.0 g (0.36 mol) D-alanine methyl ester×HCl is suspended in 500 mL of dichloromethane and 35 mL of acetone and combined with 30.0 g (0.37 mol) of sodium acetate and 80.0 g (0.38 mol) of sodium triacetoxyborohydride. The mixture is stirred for 12 h and then poured onto 400 mL of 10% sodium hydrogen carbonate solution. The organic phase is dried over Na$_2$SO$_4$ and evaporated down.

Yield: 51.0 g of a compound Z7a (yellow oil)

A suspension of 51.0 g of the compound Z7a in 450 mL water is combined with 80.0 g (0.41 mol) of 2,4-dichloro-5-nitropyridine in 450 mL of diethyl ether. At −5° C. 100 mL of 10% potassium hydrogen carbonate solution are added dropwise. The reaction mixture is stirred for 3 h, the organic phase dried over Na$_2$SO$_4$ and evaporated down.

Yield: 74 g of a compound Z7b (yellow oil)

18.6 g of the compound Z7b are dissolved in 200 mL glacial acetic acid and at 60° C. combined batchwise with 20.0 g iron powder. The mixture is stirred for 2 h at 60° C. and then suction filtered through cellulose. The residue is dissolved in ethyl acetate and washed with water and concentrated ammonia. The organic phase is dried over Na$_2$SO$_4$ and evaporated down. The residue is crystallised from diethyl ether.

Yield: 9.8 g of a compound Z7c (colourless crystals)

17.0 g of the compound Z7c and 7 mL (0.1 mol) methyl iodide are dissolved in 200 mL dimethylacetamide and at −5° C. combined with 4.0 g (0.1 mol) of sodium hydride as a 60% dispersion in mineral oil. The reaction mixture is stirred for 30 min and then poured onto 300 mL ice water. The precipitate formed is suction filtered and stirred with petroleum ether.

Yield: 14.8 g of a compound Z7d (beige crystals)

0.9 g of the compound Z7d and 1.5 g (9 mmol) 4-amino-3-methoxybenzoic acid are heated to 210° C. for 30 min. After cooling the residue is stirred with ethyl acetate and the precipitate obtained is suction filtered.

Yield: 1.2 g of a compound Z7 (grey crystals)

The following acids can, for example, be prepared analogously to the methods of synthesis hereinbefore described.

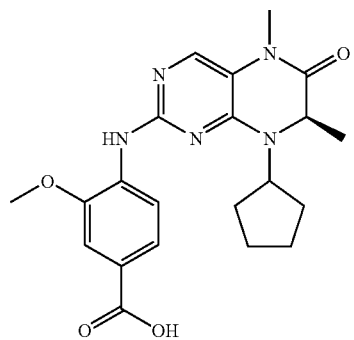

Z8

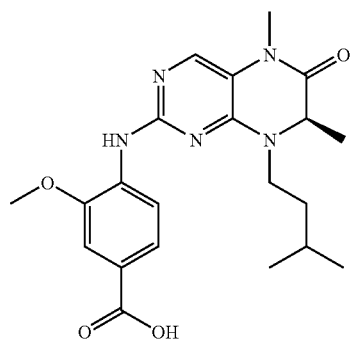

Z9

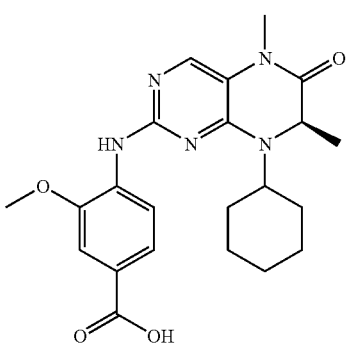

Z10

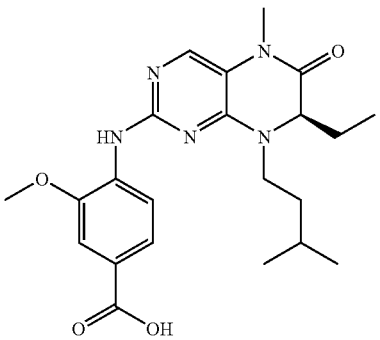

Z11

Synthesis of the Amino Components L-R5

The following amines, 1,1-dimethyl-2-dimethylamino-1-yl-ethylamine and 1,1-dimethyl-2-piperidin-1-yl-ethylamine,

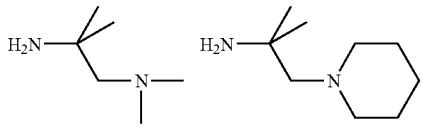

may be obtained as follows.

The compounds may be prepared according to the following references: (a) S. Schuetz et al. *Arzneimittel-Forschung* 1971, 21, 739-763, (b) V. M. Belikov et al. *Tetrahedron* 1970, 26, 1199-1216 and (c) E. B. Butler and McMillan *J. Amer. Chem. Soc.* 1950, 72, 2978. Z8

Other amines can be prepared as follows, in a modified manner compared with the literature described above.

1,1-dimethyl-2-morpholin-1-yl-ethylamine

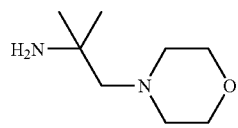

8.7 mL morpholine and 9.3 mL 2-nitropropane are prepared while cooling the reaction with ice, 7.5 mL formaldehyde (37%) and 4 mL of a 0.5 mol/L NaOH solution are slowly added dropwise (<10° C.). Then the mixture is stirred for 1 h at 25° C. and 1 h at 50° C. The solution is treated with water and ether and the aqueous phase is extracted 3× with ether. The combined organic phase is dried over NaSO4 and combined with HCl in dioxane (4 mol/l), the precipitate formed is suction filtered. Yield: 21.7 of white powder 5 g of the white powder are dissolved in 80 mL methanol and with the addition of 2 g RaNi treated with hydrogen at 35° C. and 50 psi for 40 minutes. This yields 3.6 g of 1,1-dimethyl-2-morpholin-1-yl-ethylamine.

The following amines can be prepared analogously.

1,1-dimethyl-N-methylpiperazin-1-yl-ethylamine

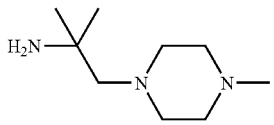

1,1-dimethyl-2-pyrrolidin-1-yl-ethylamine

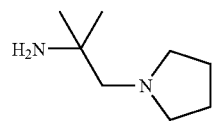

1,3-Dimorpholin-2-Amino-Propane

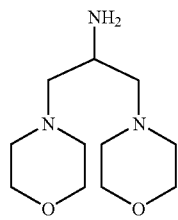

5 g of 1,3 Dimorpholine-2-nitropropane obtained from Messrs. Aldrich is dissolved in 80 mL methanol and treated with hydrogen for 5.5 h at 30° C. and 50 psi with the addition of 2 g RaNi. This yields 4.2 g of 1,3 dimorpholin-2-aminopropane.

4-Aminobenzylmorpholine

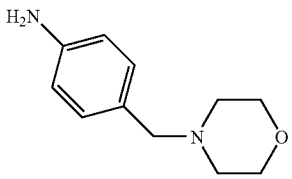

The preparation of this amine is described in the following reference:
S. Mitsuru et al. *J. Med. Chem.* 2000, 43, 2049-2063.

4-amino-1-tetrahydro-4H-pyran-4-yl-piperidine

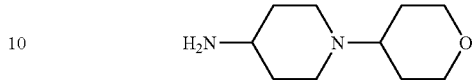

20 g (100 mmol) of 4-tert-butyloxycarbonyl-aminopiperidine are dissolved in 250 mL CH$_2$Cl$_2$ and stirred for 12 h at RT with 10 g (100 mmol) tetrahydro-4H-pyran-4-one and 42 g (200 mmol) NaBH(OAc)$_3$. Then water and potassium carbonate are added, the organic phase is separated off, dried and the solvent is eliminated in vacuo. The residue is dissolved in 200 mL CH$_2$Cl$_2$ and stirred for 12 h at RT with 100 mL trifluoroacetic acid. The solvent is eliminated in vacuo, the residue taken up with CHCl$_3$ and evaporated down again, then taken up in acetone and the hydrochloride is precipitated with ethereal HCl. Yield: 14.3 g (56%).

Cis- and trans-4-morpholino-cyclohexylamine

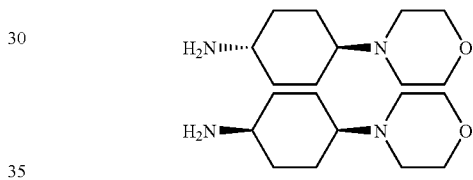

3.9 g (30 mmol) of 4-dibenzylcyclohexanone are dissolved in 100 mL of CH$_2$Cl$_2$ and stirred for 12 h at RT with 3.9 g (45 mmol) of morpholine and 9.5 g (45 mmol) NaBH(OAc)$_3$. Then water and potassium carbonate are added, the organic phase is separated off, dried and the solvent is eliminated in vacuo. The residue is purified through a silica gel column (about 20 mL silica gel; about 500 mL of ethyl acetate 90/methanol 10+1% concentrated ammonia). The appropriate fractions are evaporated down in vacuo. Yield: 6.6 g (60%) of cis-isomer and 2 g (18%) of trans-isomer.

Alternatively, the trans-dibenzyl-4-morpholino-cyclohexylamine may be prepared by the following method:

33 g (112 mmol) of 4-dibenzylcyclohexanone are dissolved in 300 mL MeOH, combined with 17.4 g (250 mmol) of hydroxylamine hydrochloride and stirred for 4 h at 60° C. The solvent is evaporated down in vacuo, combined with 500 mL water and 50 g potassium carbonate and extracted twice with 300 mL of dichloromethane. The organic phase is dried, evaporated down in vacuo, the residue is crystallised from petroleum ether, dissolved in 1.5 L of EtOH and heated to 70° C. 166 g of sodium are added batchwise and the mixture is refluxed until the sodium dissolves. The solvent is eliminated in vacuo, the residue combined with 100 mL water and extracted twice with 400 mL of ether. The organic phase is washed with water, dried, evaporated down in vacuo and the trans isomer is isolated using a column (about 1.5 L silica gel; about 2 L of ethyl acetate 80/methanol 20+2% concentrated ammonia). Yield: 12.6 g (41.2%).

6.8 g (23 mmol) of trans-1-amino-4-dibenzylaminocyclohexane is dissolved in 90 mL of DMF and stirred for 8 h at 100° C. with 5 mL (42 mmol) of 2,2'-dichloroethyl ether and 5 g of potassium carbonate. After cooling 30 mL of water is added, the precipitated crystals are suction filtered and purified through a short column (about 20 mL silica gel, about 100 mL ethyl acetate). The residue is crystallised from methanol and concentrated HCl as the dihydrochloride. Yield: 7.3 g (72.4%).

Trans-4-morpholino-cyclohexylamine 7.2 g (16.4 mmol) of trans-dibenzyl-4-morpholino-cyclohexylamine are dissolved in 100 mL of MeOH and hydrogenated on 1.4 g of Pd/C (10%) at 30-50° C. The solvent is eliminated in vacuo and the residue is crystallised from ethanol and concentrated HCl.
Yield: 3.9 g (93%).
The cis isomer may be prepared analogously.

Cis- and trans-4-piperidino-cyclohexylamine

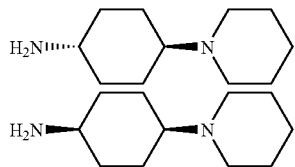

Trans-dibenzyl-4-piperidino-cyclohexylamine 2.0 g (6.8 mmol) of trans-1amino-4-dibenzylaminocyclohexane (see Example 2) is dissolved in 50 mL DMF and stirred for 48 h at RT with 1.6 g (7 mmol) of 1,5-dibromopentane and 2 g of potassium carbonate. The mixture is cooled, combined with water, extracted twice with 100 mL of dichloromethane, dried and the solvent is eliminated in vacuo. The residue is purified over a column (about 100 mL silica gel, about 500 mL ethyl acetate 80/methanol 20+1% concentrated ammonia). The desired fractions are evaporated down in vacuo and crystallised from petroleum ether. Yield: 1.2 g (49%).

Trans-4-piperidino-cyclohexylamine 1.7 g (4.8 mmol) of trans-dibenzyl-4-piperidino-cyclohexylamine are dissolved in 35 mL MeOH and hydrogenated on 350 mg of Pd/C (10%) at 20° C. The solvent is eliminated in vacuo and the residue crystallised from ethanol and concentrated HCl.
Yield: 1.1 g (78%).
The cis isomer may be prepared analogously.

Cis- and trans-4-(4-phenyl-piperazin-1-yl)-cyclohexylamine

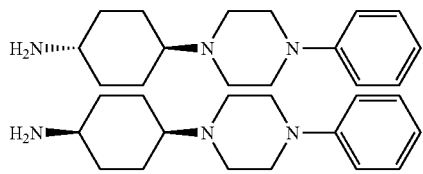

4.1 g (25.3 mmol) of 4-dibenzylcyclohexanone is dissolved in 50 mL of dichloromethane and stirred for 12 h at RT with 7.4 g (25.3 mmol) of N-phenylpyperazine and 7.4 g (35 mmol) of NaBH(OAc)$_3$. Then water and potassium carbonate are added, the organic phase is separated off, dried and the solvent is eliminated in vacuo. The residue is purified over a silica gel column (ethyl acetate 80/methanol 20+0.5% concentrated ammonia). Yield: 1.7 g (15.8%) of cis-isomer and 0.27 (2.5%) of trans-isomer.

Trans-4-(4-phenyl-piperazin-1-yl)-cyclohexylamine 270 mg (0.61 mmol) of trans-dibenzyl-[4-(4-phenyl-piperazin-1-yl)-cyclohexyl]-amine are dissolved in 5 mL MeOH and hydrogenated on 40 mg of Pd/C (10%) at 20-30° C. The solvent is eliminated in vacuo and the residue crystallised from ethanol and concentrated HCl. Yield: 110 mg (69%).
The cis isomer may be prepared analogously.

Cis- and trans-4-(4-cyclopropylmethyl-piperazin-1-yl)-cyclohexylamine

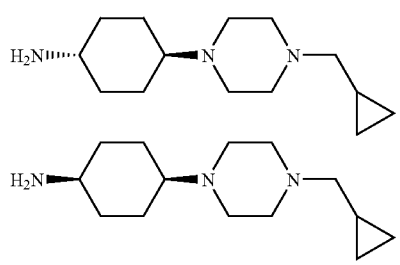

9.8 g (33.4 mmol) of 4-dibenzylcyclohexanone is dissolved in 100 mL dichloromethane and stirred for 12 h at RT with 5.6 g (40 mmol) of N-cyclopropylmethylpiperazine and 8.5 g (40 mmol) of NaBH(OAc)$_3$. Then water and potassium carbonate are added, the organic phase is separated off, dried and the solvent is eliminated in vacuo. The residue is purified over a silica gel column (about 50 mL silica gel, about 3 L ethyl acetate 95/methanol 5+0.25% concentrated ammonia. The appropriate fractions are evaporated down in vacuo. The faster eluting cis compound crystallised from ethyl acetate. The trans-compound is crystallised from ethanol+concentrated HCl. Yield: 8.5 g (61%) cis-isomer and 2.2 (13%) trans-isomer.

cis-4-(4-cyclopropylmethyl-piperazin-1-yl)-cyclohexylamine 8.5 g (20 mmol) of cis-dibenzyl-[4-(4-cyclopropylmethyl-piperazin-1-yl)-cyclohexyl]-amine are dissolved in 170 mL MeOH and hydrogenated on 1.7 g Pd/C (10%) at 30-50° C. The solvent is eliminated in vacuo and the residue is crystallised from ethanol and concentrated HCl. Yield: 4.4 g (91%).
The trans-isomer may be prepared analogously.

SYNTHESIS OF THE EXAMPLES

Example 152

0.15 g of the compound Z10, 0.14 g TBTU, 0.13 mL DIPEA are dissolved in dichloromethane and stirred for 20 minutes at 25° C. Then 90 µL 1-(3-aminopropyl)-4-methylpiperazine is added and stirred for a further 2 hours at 25° C.

The solution is then diluted with dichloromethane and extracted with water. The product is precipitated by the addition of petroleum ether, ether and ethyl acetate to the organic phase. Yield: 0.16 g of beige solid.

Example 164

0.10 g of the compound Z10, 0.1 g TBTU, 0.08 mL DIPEA are dissolved in 4 mL dichloromethane and stirred for 20 minutes at 25° C. Then 44 µL dimethylaminopropylamine are added and stirred for a further 2 hours at 25° C. The solution is then diluted with dichloromethane and extracted with water. The product is precipitated by the addition of petroleum ether, ether and acetone to the organic phase.
Yield: 0.08 g yellow solid.

Example 242

0.15 g of the compound Z10, 0.14 g TBTU, 0.13 mL DIPEA are dissolved in 5 mL dichloromethane and stirred for 20 minutes at 25° C. Then 75 µL 1-(2-aminoethyl)piperidine are added and stirred for a further 2 hours at 25° C. The solution is then diluted with dichloromethane and extracted with water. The product is precipitated by the addition of petroleum ether, ether and ethyl acetate to the organic phase. Yield: 0.14 g yellow solid.

Example 188

0.1 g of the compound Z2, 0.09 g TBTU, 0.05 mL DIPEA are dissolved in 15 mL dichloromethane and stirred for 20 minutes at 25° C. Then 33 mg 1-methyl-4-aminopiperidin are added and the mixture is stirred for a further 3 hours at 25° C. The solution is extracted with 20 mL water, then evaporated down in vacuo. The product is crystallised using ether. Yield: 0.047 g of white crystals.

Example 203

0.1 g of the compound Z2, 0.09 g TBTU, 0.5 mL DIPEA are dissolved in 15 mL dichloromethane and stirred for 30 minutes at 25° C. Then 50 mg 4-amino-1-benzylpiperidin are added and the mixture is stirred for a further 3 hours at 25° C. The solution is extracted with 20 mL water, then evaporated down in vacuo. Then the residue is chromatographed over silica gel and the isolated product is crystallised with ether. Yield: 0.015 g of white crystals.

Example 94

0.17 g of the compound Z1, 0.19 g TBTU, 0.11 mL DIPEA are dissolved in 50 mL dichloromethane and stirred for 30 minutes at 25° C. Then 63 mg of 1-methyl-4-aminopiperidine are added and the mixture is stirred for a further 17 hours at 25° C. 50 mL of water and 1 g of potassium carbonate are added to the solution and the organic phase is separated off using a phase separation cartridge, then evaporated down in vacuo. Then the product is purified by silica gel chromatography and the purified product is crystallised with ether. Yield: 0.1 g of white crystals.

Example 95

0.17 g of the compound Z1, 0.19 g TBTU, 0.11 mL DIPEA are dissolved in 50 mL dichloromethane and stirred for 30 minutes at 25° C. Then 77 mg of exo-3-β-amino-tropane are added and the mixture is stirred for a further 17 hours at 25° C. 50 mL of water and 1 g of potassium carbonate are added to the solution and the organic phase is separated off using a phase separation cartridge, then evaporated down in vacuo. Then the product is purified by silica gel chromatography and the purified product is crystallised with ether. Yield: 0.03 g of white crystals.

Example 46

0.15 g of the compound Z3, 0.12 g TBTU, 0.12 mL DIPEA are dissolved in 5 mL dichloromethane and stirred for 30 minutes at 25° C. Then 50 mg 1-methyl-4-aminopiperidin are added and the mixture is stirred for a further 2.5 hours at 25° C. The solution is then extracted with water and then evaporated down. The residue is dissolved in warm ethyl acetate and crystallised from ether and petroleum ether. Yield: 0.025 g of white crystals.

Example 80

0.2 g of the compound Z8, 0.2 g of TBTU, 0.1 mL of DIPEA are dissolved in 10 mL dichloromethane and stirred for 30 minutes at 25° C. Then 100 mg of 1-methyl-4-aminopiperidine are added and the mixture is stirred for a further 17 hours at 25° C. The solution is then extracted with a dilute potassium carbonate solution and evaporated down. The residue is crystallised using ether. Yield: 0.12 g of white crystals.

Example 190

0.2 g of compound Z8, 0.2 g of TBTU, 0.3 mL of DIPEA are dissolved in 5 mL dichloromethane and stirred for 1 h at 25° C. Then 0.13 g of 4-amino-1-benzylpiperidine are added and the mixture is stirred for a further hour at 25° C. The solution is then diluted with 10 mL methylene chloride and extracted with 20 mL water. Then the product is purified over silica gel and crystallised from ethyl acetate and ether. Yield: 0.23 g of the compound Z8.

0.23 g of the benzylamine Z8 are dissolved in 10 mL methanol, combined with 50 mg of Pd/C and hydrogenated under 3 bar for 3 h at 25° C. By adding petroleum ether and ethyl acetate white crystals are produced. These are chromatographed over silica gel and crystallised from ethyl acetate and ether. Yield: 0.075 g of white crystals.

Example 196

0.1 g of compound Z10, 0.09 g of TBTU, 0.3 mL of DIPEA are dissolved in 4 mL of dichloromethane and stirred for 20 minutes at 25° C. Then 67 mg xx amine is added and stirred for a further 2 hours at 25° C. The solution is then diluted with dichloromethane and extracted with water. It is then chromatographed over silica gel and the residue is dissolved in acetone, combined with ethereal HCl and the precipitate formed is isolated.
Yield: 0.09 g light yellow solid.

Example 166

0.1 g of the compound Z10, 0.11 g of TBTU, 0.14 mL of DIPEA are dissolved in 2 mL dimethylformamide and stirred for 3 h at 50° C. Then 55 mg of 4-morpholinomethylphenylamine is added. The reaction mixture is then cooled to ambient temperature within 17 h. Then the dimethylformamide is eliminated in vacuo, the residue is taken up in dichloromethane and extracted with water. It is then chromato-

Example 81

0.2 g of the compound Z4, 0.2 g of TBTU, 0.1 mL of DIPEA are dissolved in 10 mL dichloromethane and stirred for 30 minutes at 25° C. Then 0.1 g of 1-methyl-4-aminopiperidine are added and the mixture is stirred for a further 17 hours at 25° C. The solution is then extracted with aqueous potassium carbonate solution and then evaporated down. The product is crystallised using ether. Yield: 0.16 g of white crystals.

Example 162

0.1 g of the compound Z5, 0.07 g of TBTU, 0.15 mL of DIPEA are dissolved in 5 mL dichloromethane and stirred for 20 minutes at 25° C. Then 0.04 g 1-methyl-4-aminopiperidine are added and the mixture is stirred for a further 2 hours at 25° C. The solution is then diluted with 15 mL dichloromethane and extracted with 20 mL water. The residue is dissolved in MeOH and acetone, combined with 1 mL ethereal HCl and evaporated down. A crystalline product is produced using ether, ethyl acetate and a little MeOH. Yield: 0.1 g of white crystals.

Example 88

0.1 g of the compound Z6, 0.12 g of TBTU, 0.12 mL of DIPEA are in 10 mL dichloromethane dissolved and stirred for 30 minutes at 25° C. Then 0.04 g of 1-methyl-4-aminopiperidine are added and the mixture is stirred for a further 2 hours at 25° C. The solution is then diluted with 10 mL dichloromethane and extracted with 10 mL water. A crystalline product is produced using ether, ethyl acetate and petroleum ether. Yield: 0.6 g of white crystals.

Example 89

0.1 g of the compound Z6, 0.08 g of TBTU, 0.08 mL of DIPEA are dissolved in 10 mL dichloromethane and stirred for 30 minutes at 25° C. Then 37 µL g N,N-dimethylneopentanediamine are added and the mixture is stirred for a further 2 hours at 25° C. The solution is then diluted with 10 mL dichloromethane and extracted with 10 mL water. The product is then chromatographed over silica gel and crystallised from ethyl acetate, ether and petroleum ether. Yield: 0.005 g of white crystals.

Example 26

0.15 g of the compound Z7, 0.16 g of TBTU, 1 mL of DIPEA are dissolved in 5 mL dichloromethane and stirred for 30 minutes at 25° C. Then 0.1 g 4-morpholinocyclohexylamine are added and the mixture is stirred for a further 17 hours at 25° C. The residue is then combined with 10 mL of 10% potassium carbonate solution, the precipitate is isolated and washed with water. It is then dissolved in dichloromethane and evaporated down again. The product is crystallised from ethyl acetate. Yield: 0.1 g of white crystals.

Example 9

150 mg of the compound Z9 and 93 mg of amine are dissolved in 5 mL dichloromethane and stirred with 160 mg of TBTU and 1 mL of DIPEA for 12 h at RT. The solvent is eliminated in vacuo, the residue is combined with 10 mL of 10% potassium carbonate solution. The precipitate is suction filtered, washed with water, taken up in dichloromethane, dried and the solvent eliminated in vacuo. The residue is crystallised from ethyl acetate. Yield: 82.0 mg.

Example 16

150 mg of the compound Z8 and 73 mg of trans-4-piperidino-cyclohexylamine are dissolved in 5 mL dichloromethane and stirred with 160 mg (0.50 mmol) of TBTU and 1 mL of DIPEA for 12 h at RT. The solvent is eliminated in vacuo, the residue is combined with 10 mL of 10% potassium carbonate solution. The precipitate is suction filtered, washed with water, taken up in dichloromethane, dried and the solvent eliminated in vacuo. The residue is crystallised from ethyl acetate. Yield: 87.0 mg. 100 mg of the compound Z9 and 42 mg of 3-amino-1-ethyl-pyrrolidine are dissolved in 10 mL dichloromethane and stirred with 90 mg of TBTU and 0.5 mL of DIPEA for 12 h at RT. The solvent is eliminated in vacuo, the residue is combined with 10 mL of 10% potassium carbonate solution. The precipitate is suction filtered, washed with water, taken up in dichloromethane, dried and the solvent is eliminated in vacuo. The residue is crystallised from ethyl acetate/petroleum ether. Yield: 24.0 mg.

Example 120

100 mg of the compound Z 11 and 73 mg of 4-amino-1tetrahydro-4H-pyran-4-yl-piperidine are dissolved in 10 mL dichloromethane and stirred with 90 mg of TBTU and 0.5 mL of DIPEA for 1 h at RT. The solvent is eliminated in vacuo, the residue is combined with 10 mL of 10% potassium carbonate solution. The precipitate is suction filtered, washed with water, taken up in dichloromethane, dried and the solvent is eliminated in vacuo. The residue is crystallised from ethyl acetate/petroleum ether.
Yield: 89 mg.

Example 212

150 mg of the compound Z5 and 150 mg of trans-4-(4-cyclopropylmethyl-piperazin-1-yl)-cyclohexylamine (as the hydrochloride) are dissolved in 5 mL of dichloromethane and stirred with 160 mg of TBTU and 2 mL of DIPEA for 2 h at RT. The solvent is eliminated in vacuo, the residue is combined with 10 mL of 10% potassium carbonate solution. The precipitate is suction filtered, washed with water, taken up in dichloromethane, dried and the solvent eliminated in vacuo. The residue is purified over a column (20 mL silica gel, 300 mL ethyl acetate 90/methanol 10+2% concentrated ammonia). The appropriate fractions are evaporated down in vacuo and crystallised from ethyl acetate. Yield: 140 mg.

Example 232

390 mg of the compound Z 11 and 240 mg of trans-4-(4-butyloxycarbonyl-piperazin-1-yl)-cyclohexylamine are dissolved in 2.5 mL of NMP and stirred with 482 mg of TBTU and 1 mL triethylamine for 2 h at RT. Then 100 mL of water and 200 mg of potassium carbonate are added, the precipitate is suction filtered, washed with water and purified through a silica gel column. The appropriate fractions are evaporated down in vacuo, dissolved in 2 mL dichloromethane, combined with 2 mL of trifluoroacetic acid and stirred for 2 h at RT, combined with another 100 ml of water and 200 mg potassium carbonate and the precipitate is suction filtered and washed with water. Then the precipitate is purified through a silica gel column. The appropriate fractions are evaporated down in vacuo and the residue is crystallised from ethanol and concentrated hydrochloric acid. Yield: 95 mg.

Example 213

60 mg of the compound of Example 232 is dissolved in 10 mL ethyl acetate and stirred with 1 mL of acetic anhydride and 1 mL of triethylamine for 30 min. at RT. The solvent is eliminated in vacuo, the residue combined with water and ammonia, the crystals precipitated are suction filtered and washed with water and a little cold acetone.
Yield: 40 mg.

Example 218

1.2 g of the compound Z9 and 0.5 g of 1,4-dioxaspiro[4.5]dec-8-ylamine were dissolved in 20 mL dichloromethane and stirred with 1.28 g of TBTU and 4 mL of triethylamine for 12 h at RT. Then 50 mL of water and 0.5 g of potassium carbonate are added, the organic phase is separated off, dried and evaporated down in vacuo. The residue is crystallised from ethyl acetate, combined with 25 mL of 1 N hydrochloric acid and 20 mL of methanol and stirred for 30 min at 50° C. The methanol is eliminated in vacuo, the precipitate is suction filtered, washed with water and dried.

The residue is taken up in 20 mL dichloromethane, stirred with 0.5 g of thiomorpholine and 0.5 g of NaBH(OAc)$_3$ for 12 h at RT. Then water and potassium carbonate are added, the organic phase is separated off, dried and the solvent is eliminated in vacuo. The residue is purified over a silica gel column. The appropriate fractions are evaporated down in vacuo and the hydrochloride is precipitated with ethereal HCl.
Yield: 86 mg of trans-isomer; amorphous powder.

Example 187

200 mg of the compound Z3 in 5 mL dichloromethane is combined with 0.1 mL of diisopropylethylamine and 180 mg of TBTU and stirred for 30 min. Then 191 mg of 4-(4-methylpiperazin-1-yl)-phenylamine are added and the mixture is stirred overnight. The reaction mixture is combined with water and the aqueous phase extracted with dichloromethane. The combined organic phases are dried over Na$_2$SO$_4$ and evaporated down. The residue is purified by column chromatography (eluant:dichloromethane/methanol 100:7).
Yield: 128 mg (light yellow crystals).

The compounds of Formula (I) listed in Table 1, inter alia, are obtained analogously to the procedure described hereinbefore. The abbreviations $X_1$, $X_2$, $X_3$, $X_4$ and $X_5$ used in Table 1 in each case denote a link to a position in the general Formula shown under Table 1 instead of the corresponding groups $R^1$, $R^2$, $R^3$, $R^4$ and $L$-$R^5$.

Table 1

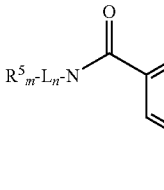

| Example | $R^1$ | $R^2$ | Config. $R^1$ or $R^2$ | $R^3$ | $R^4$ | $L_n$-$R^5_m$ |
|---|---|---|---|---|---|---|
| 1 | H | $X_2$—CH$_3$ | R |  | $X_4$—O—CH$_3$ | 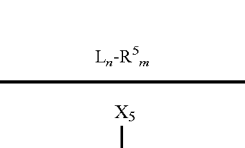 |
| 2 | H | $X_2$—CH$_3$ | R | 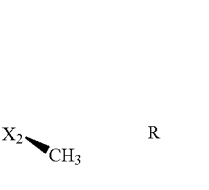 | $X_4$—O—CH$_3$ |  |
| 3 | H | $X_2$—CH$_3$ | R | 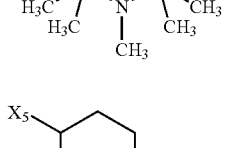 | H | 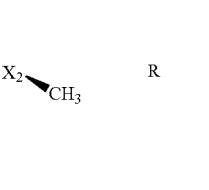 |

Table 1-continued

| Example | R¹ | R² | Config. R¹ or R² | R³ | R⁴ | L$_n$-R$^5_m$ |
|---------|----|----|-----|----|----|------|
| 4 | H | X₂—CH₃ | R | X₃-CH₂CH(CH₃)₂ (isobutyl via X₃) | H | X₅-(1-ethylpiperidin-4-yl) |
| 5 | H | X₂—CH₃ | R | X₃-CH₂C(CH₃)₃ (neopentyl via X₃) | X₄-O-CH₃ | X₅-(1,2,2,6,6-pentamethylpiperidin-4-yl) |
| 6 | H | X₂—CH₃ | R | X₃-CH₂C(CH₃)₃ | X₄-O-CH₃ | X₅-(1-ethylpiperidin-4-yl) |
| 7 | H | X₂—CH₃ | R | X₃-CH₂C(CH₃)₃ | X₄-O-CH₃ | X₅-(1-isopropylpiperidin-4-yl) |
| 8 | H | X₂—CH₃ | R | X₃-CH₂C(CH₃)₃ | H | X₅-(1,2,2,6,6-pentamethylpiperidin-4-yl) |
| 9 | H | X₂—CH₃ | R | X₃-CH₂CH(CH₃)₂ | X₄-O-CH₃ | X₅-(trans-4-morpholinocyclohexyl) |

TABLE 1-continued

| Example | R¹ | R² | Config. R¹ or R² | R³ | R⁴ | Lₙ-R⁵ₘ |
|---|---|---|---|---|---|---|
| 10 | H | X₂—CH₃ | R | X₃-CH₂-C(CH₃)₃ | H | X₅-(4-piperidinyl)-N-benzyl |
| 11 | H | X₂—CH₃ | R | X₃-CH₂-C(CH₃)₃ | H | X₅-(4-piperidinyl)-N-ethyl |
| 12 | H | X₂—CH₃ | R | X₃-CH₂-C(CH₃)₃ | H | X₅-(4-piperidinyl)-N-isopropyl |
| 13 | H | X₂—CH₃ | R | X₃-cyclopentyl | CH₃-O-X₄ | X₅-(4-piperidinyl)-N-isopropyl |
| 14 | H | X₂—CH₃ | R | X₃-cyclopentyl | H | X₅-(4-piperidinyl)-N-isopropyl |
| 15 | H | X₂—CH₃ | R | X₃-cyclopentyl | X₄-O-CH₃ | X₅-trans-(4-cyclohexyl)-N-pyrrolidinyl |

TABLE 1-continued

| Example | R¹ | R² | Config. R¹ or R² | R³ | R⁴ | Lₙ-R⁵ₘ |
|---|---|---|---|---|---|---|
| 16 | H | X₂—CH₃ | R | X₃-cyclopentyl | X₄-O-CH₃ | X₅-cyclohexyl-N-piperidinyl |
| 17 | H | X₂—CH₃ | R | X₃-cyclopentyl | CH₃-O-X₄ | X₅-(1-ethylpiperidin-4-yl) |
| 18 | H | X₂—CH₃ | R | X₃-cyclopentyl | H | X₅-(1-ethylpiperidin-4-yl) |
| 19 | H | X₂-CH₃ | R | X₃-cyclopentyl | X₄-O-CH₃ | X₅-cyclohexyl-N-pyrrolidinyl |
| 20 | H | X₂—CH₃ | R | X₃-isopropyl | CH₃-O-X₄ | X₅-(1-ethylpiperidin-4-yl) |

TABLE 1-continued

| Example | R¹ | R² | Config. R¹ or R² | R³ | R⁴ | Lₙ-R⁵ₘ |
|---|---|---|---|---|---|---|
| 21 | H | X₂―CH₃ | R | X₃―cyclopentyl | CH₃―O―X₄ | 1,2,2,6,6-pentamethylpiperidin-4-yl (X₅) |
| 22 | H | X₂―CH₃ | R | X₃―cyclopentyl | CH₃―O―X₄ | 1-ethylpiperidin-4-yl (X₅) |
| 23 | H | X₂―CH₃ | R | X₃―cyclopentyl | CH₃―O―X₄ | 1-isopropylpiperidin-4-yl (X₅) |
| 24 | H | X₂◂CH₃ | R | X₃―cyclopentyl | X₄―O―CH₃ | 4-morpholinocyclohexyl (X₅) |
| 25 | H | X₂◂CH₃ | R | X₃―cyclopentyl | X₄―O―CH₃ | 4-piperidin-1-yl-cyclohexyl (X₅) |

Table 1-continued

| Example | R¹ | R² | Config. R¹ or R² | R³ | R⁴ | $L_n$-$R^5_m$ |
|---|---|---|---|---|---|---|
| 26 | H | X₂–CH₃ (wedge) | R | X₃-CH(CH₃)₂ (isobutyl) | X₄-O-CH₃ | X₅-cyclohexyl-N-morpholine (trans) |
| 27 | H | X₂–CH₃ | R | X₃-CH(CH₃)₂ | X₄-O-CH₃ | X₅-cyclohexyl-N-morpholine (trans) |
| 28 | H | X₂–CH₃ | R | X₃-CH(CH₃)₂ | X₄-O-CH₃ | X₅-cyclohexyl-N-morpholine (trans) |
| 29 | H | X₂–CH₃ (wedge) | R | X₃-CH₂CH(CH₃)₂ | X₄-O-CH₃ | X₅-cyclohexyl-N-piperidine (trans) |
| 30 | H | X₂–CH₃ (wedge) | R | X₃-cyclopentyl | CH₃-O-X₄ | X₅-(2,2,6,6-tetramethyl-1-methyl-piperidin-4-yl) |

Table 1-continued

| Example | R¹ | R² | Config. R¹ or R² | R³ | R⁴ | Lₙ-R⁵ₘ |
|---------|----|----|------------------|----|----|--------|
| 31 | H | X₂⁃CH₃ | R | cyclopentyl-X₃ | H | 2,2,6,6-tetramethyl-1-methyl-piperidin-4-yl-X₅ |
| 32 | H | X₂⁃CH₃ | R | (CH₃)₂CH-X₃ | CH₃-O-X₄ | 2,2,6,6-tetramethyl-1-methyl-piperidin-4-yl-X₅ |
| 33 | H | X₂⁃CH₃ | R | (CH₃)₂CH-X₃ | H | 2,2,6,6-tetramethyl-1-methyl-piperidin-4-yl-X₅ |
| 34 | H | X₂⁃CH₃ | R | (CH₃)₂CHCH₂CH₂-X₃ | CH₃-O-X₄ | 4-(pyrrolidin-1-yl)cyclohexyl-X₅ |
| 35 | H | X₂⁃CH₃ | R | (CH₃)₂CHCH₂CH₂-X₃ | CH₃-O-X₄ | 4-(pyrrolidin-1-yl)cyclohexyl-X₅ |

TABLE 1-continued

| Example | R¹ | R² | Config. R¹ or R² | R³ | R⁴ | Lₙ-R⁵ₘ |
|---|---|---|---|---|---|---|
| 36 | H | X₂—CH₃ | R | X₃-cyclopentyl | X₄-O-CH₃ | X₅-cyclohexyl-pyrrolidine |
| 37 | H | X₂—CH₃ | R | X₃-CH₂CH(CH₃)₂ (isobutyl-like) | X₄-O-CH₃ | X₅-pyrrolidine-N-ethyl |
| 38 | H | X₂—CH₃ | R | X₃-CH₂CH(CH₃)₂ | X₄-O-CH₃ | X₅-cyclohexyl-morpholine |
| 39 | H | X₂—CH₃ | R | X₃-CH₂CH(CH₃)₂ | H | X₅-pyrrolidine-N-ethyl |
| 40 | H | X₂—CH₃ | R | X₃-cyclopentyl | X₄-O-CH₃ | X₅-cyclohexyl-morpholine |

TABLE 1-continued

| Example | R¹ | R² | Config. R¹ or R² | R³ | R⁴ | Lₙ-R⁵ₘ |
|---|---|---|---|---|---|---|
| 41 | H | X₂–CH₃ | R | X₃–phenyl | O–CH₃ (X₄) | X₅-(1-methylpiperidin-4-yl) |
| 42 | H | X₂–CH₂CH₃ | R | X₃–CH₂CH₂CH(CH₃)₂ | O–CH₃ (X₄) | X₅-(8-methyl-8-azabicyclo[3.2.1]oct-3-yl) |
| 43 | X₁–CH₃ | X₂–CH₃ | | X₃–CH₂CH₂CH(CH₃)₂ | H₃C–O–X₄ | X₅-(8-methyl-8-azabicyclo[3.2.1]oct-3-yl) |
| 44 | H | X₂–CH₂CH₃ | R | X₃–cyclopentyl | H | X₅-(1-methylpiperidin-4-yl) |
| 45 | H | X₂–CH₂CH₃ | R | X₃–cyclopentyl | H₃C–O–X₄ | X₅-(8-methyl-8-azabicyclo[3.2.1]oct-3-yl) |
| 46 | H | X₂–CH₂CH₃ | R | X₃–cyclopentyl | H₃C–O–X₄ | X₅-(1-methylpiperidin-4-yl) |

Table 1-continued

| Example | R¹ | R² | Config. R¹ or R² | R³ | R⁴ | Lₙ-R⁵ₘ |
|---------|----|----|------------------|----|----|--------|
| 47 | H | X₂–CH₃ (ethyl) | R | X₃-cyclopentyl | H | X₅-(N-methyl tropane) |
| 48 | H | X₂–CH₃ | R | X₃-phenyl | H | X₅-(1-methylpiperidin-4-yl) |
| 49 | H | X₂–CH₃ | R | X₃-cyclopentyl | CH₃-O-X₄ | X₅-C(CH₃)₂-CH₂-pyrrolidinyl |
| 50 | H | X₂–CH₃ | R | X₃-CH₂-C(CH₃)₃ | X₄-O-CH₃ | X₅-C(CH₃)₂-CH₂-pyrrolidinyl |
| 51 | H | X₂-cyclopropyl | R | X₃-cyclopentyl | CH₃-O-X₄ | X₅-CH₂-C(CH₃)(CH₃)-CH₂-N(CH₃)₂ |
| 52 | H | X₂–CH₃ | R | X₃-CH₂-C(CH₃)₃ | CH₃-O-X₄ | X₅-CH₂-C(CH₃)(CH₃)-CH₂-N(CH₃)₂ |

Table 1-continued

| Example | R¹ | R² | Config. R¹ or R² | R³ | R⁴ | $L_n$-$R^5_m$ |
|---|---|---|---|---|---|---|
| 53 | X₁—CH₃ | X₂—CH₃ | | 3-methylbutyl (X₃-CH₂CH₂CH(CH₃)₂) | OCH₃ (O-X₄) | X₅-CH₂C(CH₃)(CH₃)-CH₂-N(CH₃)₂ |
| 54 | H | X₂—CH₂CH₃ | R | isopropyl (X₃-CH(CH₃)₂) | OCH₃ | X₅-CH₂C(CH₃)(CH₃)-CH₂-pyrrolidinyl |
| 55 | H | X₂—CH₂CH₃ | R | cyclopentyl (X₃) | OCH₃ | X₅-CH₂C(CH₃)(CH₃)-CH₂-pyrrolidinyl |
| 56 | H | X₂—CH₃ | R | isopropyl | OCH₃ | X₅-CH₂C(CH₃)(CH₃)-CH₂-pyrrolidinyl |
| 57 | H | X₂—CH₂CH₃ | R | isopropyl | OCH₃ | X₅-CH₂C(CH₃)(CH₃)-CH₂-N(CH₃)₂ |
| 58 | H | X₂—CH₂CH₃ | R | cyclopentyl | OCH₃ | X₅-CH₂C(CH₃)(CH₃)-CH₂-N(CH₃)₂ |

Table 1-continued

| Example | R¹ | R² | Config. R¹ or R² | R³ | R⁴ | L$_n$-R$^5{}_m$ |
|---|---|---|---|---|---|---|
| 59 | H | X₂—CH₃ | R | X₃—phenyl | H₃C—O—X₄ | X₅—(1-methylpiperidin-4-yl) |
| 60 | H | X₂—CH₃ | R | X₃—cyclopentyl | CH₃—O—X₄ | X₅—CH₂C(CH₃)₂CH₂N(CH₃)₂ |
| 61 | X₁—CH₃ | X₂—CH₃ |  | X₃—CH₂CH(CH₃)₂ | H₃C—O—X₄ | X₅—(1-methylpiperidin-4-yl) |
| 62 | H | X₂—CH₃ | R | X₃—cyclopentyl | CH₃—O—X₄ | (H₃CH₂C)₂N—CH₂CH₂—X₅ |
| 63 | H | X₂—CH₃ | R | X₃—cyclopentyl | CH₃—O—X₄ | morpholine-N—(CH₂)₃—X₅ |
| 64 | H | X₂—CH₃ | R | X₃—cyclopentyl | CH₃—O—X₄ | piperidine-N—(CH₂)₃—X₅ |
| 65 | H | X₂—CH₃ | R | X₃—cyclopentyl | CH₃—O—X₄ | morpholine-N—CH₂CH₂—X₅ |
| 66 | H | X₂—CH₃ | R | X₃—cyclopentyl | CH₃—O—X₄ | piperidine-N—CH₂CH₂—X₅ |

TABLE 1-continued

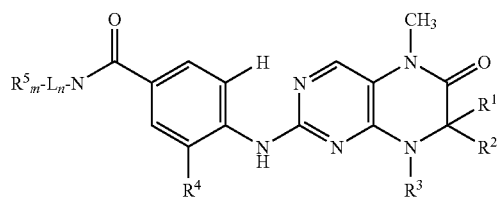

| Example | R¹ | R² | Config. R¹ or R² | R³ | R⁴ | Lₙ-R⁵ₘ |
|---|---|---|---|---|---|---|
| 67 | H | X₂⏤CH₃ | R | cyclopentyl-X₃ | CH₃O-X₄ | H₃C-N(CH₃)-CH₂CH₂-X₅ |
| 68 | H | X₂⏤CH₃ | R | cyclopentyl-X₃ | H | N-methyl azabicyclic-X₅ |
| 69 | H | X₂⏤CH₃ | R | cyclopentyl-X₃ | H | morpholino-(CH₂)₃-X₅ |
| 70 | H | X₂⏤CH₃ | R | cyclopentyl-X₃ | H | piperidino-CH₂CH₂-X₅ |
| 71 | H | X₂—CH₃ | R | CH(CH₃)₂-X₃ | CH₃O-X₄ | X₅-CH₂CH₂-morpholino |
| 72 | H | X₂—CH₃ | R | CH(CH₃)₂-X₃ | CH₃O-X₄ | X₅-CH₂CH₂-piperidino |
| 73 | H | X₂—CH₃ | R | CH(CH₃)₂-X₃ | H | X₅-CH₂CH₂-N(CH₂CH₃)₂ |
| 74 | H | X₂—CH₃ | R | CH(CH₃)₂-X₃ | CH₃O-X₄ | X₅-CH₂CH₂-N(CH₂CH₃)₂ |

TABLE 1-continued

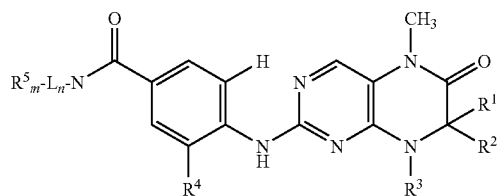

| Example | R¹ | R² | Config. R¹ or R² | R³ | R⁴ | $L_n$-$R^5_m$ |
|---|---|---|---|---|---|---|
| 75 | H | X₂—CH₃ | R | cyclopentyl-X₃ | CH₃—O—X₄ | (H₃C)(CH₃)N—CH₂CH₂CH₂—X₅ |
| 76 | H | X₂—CH₃ | R | cyclopentyl-X₃ | CH₃—O—X₄ | (H₃C-CH₂)(CH₂-CH₃)N—CH₂CH₂CH₂—X₅ |
| 77 | H | X₂—CH₃ | R | isopropyl-X₃ | H | piperidinyl-CH₂CH₂—X₅ |
| 78 | H | X₂—CH₃ | R | isopropyl-X₃ | H | morpholinyl-CH₂CH₂—X₅ |
| 79 | H | X₂—CH₃ | R | cyclopentyl-X₃ | H | (1-methylpiperidin-4-yl)—X₅ |
| 80 | H | X₂—CH₃ | R | cyclopentyl-X₃ | CH₃—O—X₄ | (1-methylpiperidin-4-yl)—X₅ |
| 81 | H | X₂—cyclopropyl | R | cyclopentyl-X₃ | CH₃—O—X₄ | (1-methylpiperidin-4-yl)—X₅ |

Table 1-continued

| Example | R¹ | R² | Config. R¹ or R² | R³ | R⁴ | Lₙ-R⁵ₘ |
|---|---|---|---|---|---|---|
| 82 | H | X₂-cyclopropyl | R | X₃-cyclopentyl | OCH₃, X₄ | X₅-(N-methyl-azabicyclic) |
| 83 | H | X₂-CH₃ | R | X₃-cyclopentyl | H₃C-X₄ | N-methyl-piperidin-4-yl-X₅ |
| 84 | H | X₂-CH₃ | R | X₃-cyclohexyl | OCH₃, X₄ | X₅-(1-methylpiperidin-4-yl) |
| 85 | H | X₂-CH₃ | R | X₃-cyclohexyl | H | X₅-(1-methylpiperidin-4-yl) |
| 86 | H | X₂-CH₃ | R | X₃-cyclohexyl | OCH₃, X₄ | X₅-CH₂-C(CH₃)(H₃C)-N(CH₃)₂ |
| 87 | H | X₂-CH₃ | R | X₃-cyclohexyl | OCH₃, X₄ | X₅-C(CH₃)(H₃C)-CH₂-pyrrolidin-1-yl |
| 88 | H | X₂-CH₂CH₃ | R | X₃-phenyl | H₃C-O-X₄ | X₅-(1-methylpiperidin-4-yl) |

Table 1-continued

| Example | R¹ | R² | Config. R¹ or R² | R³ | R⁴ | Lₙ-R⁵ₘ |
|---|---|---|---|---|---|---|
| 89 | H | X₂-CH₂CH₃ | R | phenyl (X₃) | H₃C-O-X₄ | X₅-CH₂-C(CH₃)₂-CH₂-N(CH₃)₂ |
| 90 | H | X₂-CH₂CH₃ | R | X₃-CH₂CH₂-CH(CH₃)₂ | CH₃-O-X₄ | X₅-C(CH₃)₂-CH₂-N(CH₃)₂ (with H₃C) |
| 91 | H | X₂-CH₃ | R | X₃-cyclohexyl | CH₃-O-X₄ | X₅-(N-methyl tropane) |
| 92 | H | X₂-CH₃ | R | X₃-cyclohexyl | H | X₅-(N-methyl tropane) |
| 93 | H | X₂-cyclopropyl | R | X₃-cyclopentyl | H | H₃C-N-piperidine-X₅ |
| 94 | H | X₂-CH₃ | R | X₃-cyclohexyl | H₃C-X₄ | X₅-(N-methyl piperidine) |
| 95 | H | X₂-CH₃ | R | X₃-cyclohexyl | H₃C-X₄ | X₅-(N-methyl tropane) |

Table 1-continued

| Example | R¹ | R² | Config. R¹ or R² | R³ | R⁴ | Lₙ-R⁵ₘ |
|---------|----|----|------------------|----|----|--------|
| 96 | H | X₂—CH₃ (wedge) | R | cyclohexyl-X₃ | H₃C—O—X₄ | X₅—(1-methylpiperidin-4-yl) |
| 97 | H | X₂—CH₃ (wedge) | R | cyclohexyl-X₃ | H₃C—O—X₄ | X₅—(4-morpholinocyclohexyl) |
| 98 | H | X₂—CH₃ (hash) | R | cyclohexyl-X₃ | X₄—O—CH₃ | X₅—(4-pyrrolidin-1-yl-cyclohexyl) |
| 99 | H | X₂—CH₃ | R | isopropyl-X₃ (H₃C-CH-CH₃) | X₄—O—CH₃ | X₅—(4-(4-(cyclopropylmethyl)piperazin-1-yl)cyclohexyl) |

Table 1-continued
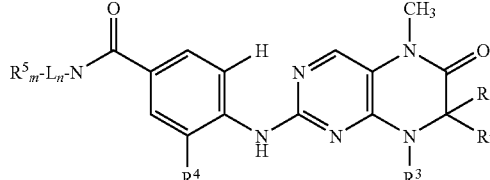
| Example | R¹ | R² | Config. R¹ or R² | R³ | R⁴ | Lₙ-R⁵ₘ |
|---|---|---|---|---|---|---|
| 100 | H | X₂–CH₃ | R | isopentyl via X₃ | X₄–O–CH₃ | X₅–(trans-cyclohexyl)–piperazine–N–CH₂–cyclopropyl |
| 101 | H | X₂–CH₃ | R | isopropyl via X₃ | CH₃–O–X₄ | X₅–piperidine–N–benzyl |
| 102 | H | X₂–CH₂CH₃ | R | isopropyl via X₃ | CH₃–O–X₄ | X₅–piperidine–N–benzyl |
| 103 | H | X₂–CH₃ | R | cyclopentyl via X₃ | CH₃–O–X₄ | X₅–piperidine–N–benzyl |

TABLE 1-continued

| Example | R¹ | R² | Config. R¹ or R² | R³ | R⁴ | Lₙ-R⁵ₘ |
|---|---|---|---|---|---|---|
| 104 | H | X₂–CH₃ | R | X₃–phenyl | CH₃–O–X₄ | X₅–(1-benzylpiperidin-4-yl) |
| 105 | H | X₂–CH₃ | R | X₃–cyclopentyl | X₄–O–CH₃ | X₅–trans-4-(4-(cyclopropylmethyl)piperazin-1-yl)cyclohexyl |
| 106 | H | X₂–CH₃ | R | X₃–cyclopentyl | X₄–O–CH₃ | X₅–trans-4-(4-methylpiperazin-1-yl)cyclohexyl |
| 107 | H | X₂–CH₃ | R | X₃–cyclopentyl | X₄–O–CH₃ | X₅–trans-4-(4-(cyclopropylmethyl)piperazin-1-yl)cyclohexyl |

Table 1-continued

| Example | R¹ | R² | Config. R¹ or R² | R³ | R⁴ | L$_n$-R$^5_m$ |
|---|---|---|---|---|---|---|
| 108 | H | X₂—CH₃ (wedge) | R | X₃-CH(CH₃)₂ | CH₃-O-X₄ | X₅-piperidine-N-tetrahydropyran |
| 109 | H | X₂—CH₃ (dash) | R | X₃-cyclopentyl | CH₃-O-X₄ | X₅-piperidine-N-tetrahydropyran |
| 110 | H | X₂—CH₃ (wedge) | R | X₃-CH(CH₃)₂ | X₄-O-CH₃ | X₅-cyclohexyl-piperazine-N-CH₂-cyclopropyl |
| 111 | H | X₂—CH₃ (dash) | R | X₃-CH₂-CH(CH₃)₂ | CH₃-O-X₄ | X₅-piperidine-N-tetrahydropyran |

Table 1-continued

| Example | R¹ | R² | Config. R¹ or R² | R³ | R⁴ | Lₙ-R⁵ₘ |
|---------|----|----|------------------|----|----|--------|
| 112 | H | X₂–CH₃ | R | X₃–CH(CH₃)₂ | X₄–O–CH₃ | X₅–cyclohexyl–piperazine–CH₂–cyclopropyl |
| 113 | H | X₂–CH₂CH₃ | R | X₃–CH(CH₃)₂ | X₄–O–CH₃ | X₅–cyclohexyl–N-methylpiperazine |
| 114 | H | X₂–CH₃ | R | X₃–CH₂CH₂CH(CH₃)₂ | X₄–O–CH₃ | X₅–cyclohexyl–N(CH₃)₂ |
| 115 | H | X₂–CH₃ | R | X₃–cyclohexyl | CH₃–O–X₄ | X₅–piperidine–CH₂–phenyl |

Table 1-continued

| Example | R¹ | R² | Config. R¹ or R² | R³ | R⁴ | Lₙ-R⁵ₘ |
|---|---|---|---|---|---|---|
| 116 | H | X₂–CH₃ (ethyl) | R | X₃–cyclopentyl | CH₃–O–X₄ | X₅–piperidinyl-N-(tetrahydropyran-4-yl) |
| 117 | H | X₂–CH₃ | R | X₃–cyclohexyl | CH₃–O–X₄ | X₅–(1,2,2,6,6-pentamethylpiperidin-4-yl) |
| 118 | H | X₂–CH₃ | R | X₃–cyclohexyl | CH₃–O–X₄ | X₅–(1-isopropylpiperidin-4-yl) |
| 119 | H | X₂–CH₃ | R | X₃–cyclohexyl | CH₃–O–X₄ | X₅–(1-ethylpiperidin-4-yl) |
| 120 | H | X₂–CH₃ | R | X₃–cyclohexyl | CH₃–O–X₄ | X₅–piperidinyl-N-(tetrahydropyran-4-yl) |

Table 1-continued

| Example | R¹ | R² | Config. R¹ or R² | R³ | R⁴ | Lₙ-R⁵ₘ |
|---------|----|----|------------------|----|----|--------|
| 121 | H | X₂—CH₃ | R | X₃-cyclohexyl | CH₃O—X₄ | X₅-(3R)-1-ethylpyrrolidinyl |
| 122 | H | X₂—CH₃ | R | X₃-cyclohexyl | CH₃O—X₄ | X₅-(3R)-1-isopropylpyrrolidinyl |
| 123 | H | X₂—CH₃ | R | X₃-cyclohexyl | CH₃O—X₄ | X₅-(3R)-1-ethylpyrrolidinyl |
| 124 | H | X₂—CH₃ | R | X₃-cyclohexyl | CH₃O—X₄ | X₅-(3R)-1-isopropylpyrrolidinyl |
| 125 | H | X₂—CH₃ | R | X₃-cyclohexyl | X₄—O—CH₃ | X₅-trans-4-(pyrrolidin-1-yl)cyclohexyl |

TABLE 1-continued

| Example | R¹ | R² | Config. R¹ or R² | R³ | R⁴ | Lₙ-R⁵ₘ |
|---|---|---|---|---|---|---|
| 126 | H | X₂▬CH₃ | R | X₃–cyclohexyl | X₄–O–CH₃ | X₅–cyclohexyl–N-piperidinyl |
| 127 | H | X₂▬CH₃ | R | X₃–cyclohexyl | X₄–O–CH₃ | X₅–cyclohexyl–N-piperidinyl |
| 128 | H | X₂–CH₃ | R | X₃–cyclopentyl | X₄–O–CH₃ | X₅–cyclohexyl–N-piperidinyl |
| 129 | H | X₂–CH₃ | R | X₃–CH(CH₃)₂ | X₄–O–CH₃ | X₅–cyclohexyl–N-piperidinyl |

Table 1-continued
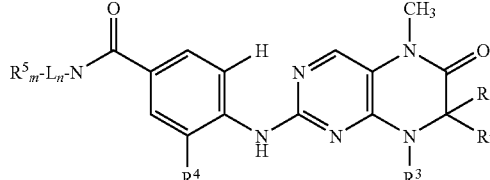
| Example | R¹ | R² | Config. R¹ or R² | R³ | R⁴ | $L_n$-$R^5_m$ |
|---|---|---|---|---|---|---|
| 130 | H | $X_2$\CH₃ | R | $X_3$ cyclohexyl | $X_4$ O-CH₃ | $X_5$ cyclohexyl-morpholine |
| 131 | H | $X_2$/CH₃ | R | $X_3$ cyclopentyl | $X_4$ O-CH₃ | $X_5$ cyclohexyl-morpholine |
| 132 | H | $X_2$/CH₃ | R | $X_3$ CH(CH₃)₂ | $X_4$ O-CH₃ | $X_5$ cyclohexyl-pyrrolidine |
| 133 | H | $X_2$/CH₃ | R | $X_3$ cyclopentyl | $X_4$ O-CH₃ | $X_5$ cyclohexyl-morpholine |

Table 1-continued

| Example | R¹ | R² | Config. R¹ or R² | R³ | R⁴ | Lₙ-R⁵ₘ |
|---|---|---|---|---|---|---|
| 134 | H | X₂—CH₃ | R | X₃-cyclopentyl | X₄-O-CH₃ | X₅-cyclohexyl-N(piperazine)-phenyl |
| 135 | H | X₂—CH₃ | R | X₃-CH(CH₃)₂ | X₄-O-CH₃ | X₅-cyclohexyl-N-pyrrolidine |
| 136 | H | X₂—CH₃ | R | X₃-cyclopentyl | X₄-O-CH₃ | X₅-cyclohexyl-N-piperidine |
| 137 | H | X₂—CH₃ | R | X₃-cyclohexyl | X₄-O-CH₃ | X₅-cyclohexyl-N-morpholine |

Table 1-continued

| Example | R¹ | R² | Config. R¹ or R² | R³ | R⁴ | Lₙ-R⁵ₘ |
|---------|----|----|------------------|----|----|--------|
| 138 | H | X₂–CH₃ | R | X₃–cyclopentyl | X₄–O–CH₃ | X₅–(trans-cyclohexyl)–pyrrolidin-1-yl |
| 139 | H | X₂–CH₃ | R | X₃–CH(CH₃)₂ | H₃C–O–X₄ | X₅–(8-methyl-8-azabicyclo[3.2.1])yl |
| 140 | H | X₂–CH₃ | R | X₃–CH(CH₃)₂ | H₃C–O–X₄ | X₅–(1-methylpiperidin-4-yl) |
| 141 | H | X₂–CH₃ | R | X₃–CH(CH₃)₂ | H₃C–O–X₄ | X₅–(CH₂)₃–morpholin-4-yl |
| 142 | H | X₂–CH₃ | R | X₃–CH(CH₃)₂ | H₃C–O–X₄ | X₅–(CH₂)₃–piperidin-1-yl |
| 143 | H | X₂–CH₃ | R | X₃–CH(CH₃)₂ | H | X₅–(CH₂)₃–morpholin-4-yl |

TABLE 1-continued

| Example | R¹ | R² | Config. R¹ or R² | R³ | R⁴ | Lₙ-R⁵ₘ |
|---|---|---|---|---|---|---|
| 144 | H | X₂–CH₃ | R | X₃–CH(CH₃)₂ | H | X₅–(1-methylpiperidin-4-yl) |
| 145 | H | H₃C–X₂ (CH₃) | R | H₃C–C(CH₃)₂–CH₂–X₃ | X₄–O–CH₃ | X₅–(1-methylpiperidin-4-yl) |
| 146 | H | X₂–CH₃ | R | X₃–CH₂–CH(CH₃)₂ | X₄–O–CH₃ | X₅–(1-methylpiperidin-4-yl) |
| 147 | H | H₃C–X₂ (CH₃) | R | H₃C–C(CH₃)₂–CH₂–X₃ | H | X₅–(2-methyl-2-azabicyclic, N-CH₃) |
| 148 | H | X₂–CH₂–CH₃ | R | X₃–CH₂–CH(CH₃)₂ | X₄–O–CH₃ | X₅–CH₂CH₂–piperidin-1-yl |
| 149 | H | X₂–CH₂–CH₃ | R | X₃–CH₂–CH(CH₃)₂ | X₄–O–CH₃ | X₅–CH₂CH₂–N(CH₂CH₃)₂ |
| 150 | H | X₂–CH₂–CH₃ | R | X₃–CH₂–CH(CH₃)₂ | H | X₅–CH₂CH₂–piperidin-1-yl |

Table 1-continued

| Example | R¹ | R² | Config. R¹ or R² | R³ | R⁴ | Lₙ-R⁵ₘ |
|---|---|---|---|---|---|---|
| 151 | H | X₂–CH₃ | R | X₃–CH₂CH(CH₃)₂ (isobutyl) | OCH₃ (X₄) | X₅–(CH₂)₃–morpholine |
| 152 | H | X₂–CH₃ | R | X₃–CH₂CH(CH₃)₂ | OCH₃ (X₄) | X₅–(CH₂)₃–N-methylpiperazine |
| 153 | H | X₂–CH₃ | R | X₃–CH₂CH(CH₃)₂ | OCH₃ (X₄) | X₅–(CH₂)₄–N(CH₂CH₃)₂ |
| 154 | H | X₂–CH₃ | R | X₃–CH₂CH(CH₃)₂ | H | X₅–(CH₂)₃–N-methylpiperazine |
| 155 | H | X₂–CH₃ | R | X₃–CH₂CH(CH₃)₂ | H | X₅–(CH₂)₃–morpholine |

Table 1-continued

| Example | R¹ | R² | Config. R¹ or R² | R³ | R⁴ | $L_n$-$R^5_m$ |
|---|---|---|---|---|---|---|
| 156 | H | X₂-CH₃ (ethyl) | R | X₃-CH₂CH₂CH(CH₃)₂ | CH₃-O-X₄ | X₅-CH₂CH₂-morpholine |
| 157 | H | X₂-CH₃ (ethyl) | R | X₃-CH₂CH₂CH(CH₃)₂ | CH₃-O-X₄ | X₅-CH₂CH₂CH₂-pyrrolidine |
| 158 | H | X₂-CH₃ (ethyl) | R | X₃-CH₂CH₂CH(CH₃)₂ | CH₃-O-X₄ | X₅-CH₂CH₂-N(CH₂CH₃)₂ |
| 159 | H | X₂-CH₃ (ethyl) | R | X₃-CH₂CH₂CH(CH₃)₂ | CH₃-O-X₄ | X₅-CH₂CH₂-N(CH₃)₂ |
| 160 | H | X₂-CH₃ (ethyl) | R | X₃-CH₂CH₂CH(CH₃)₂ | CH₃-O-X₄ | X₅-CH₂CH₂-N(CH(CH₃)₂)₂ |
| 161 | X₁-CH₃ | X₂-CH₃ | | X₃-CH₂CH₂CH(CH₃)₂ | H₃C-O-X₄ | X₅-CH₂CH₂-N(CH₂CH₃)₂ |

Table 1-continued

| Example | R¹ | R² | Config. R¹ or R² | R³ | R⁴ | Lₙ-R⁵ₘ |
|---|---|---|---|---|---|---|
| 162 | X₁—CH₃ | X₂—CH₃ | | X₃-CH₂CH(CH₃)₂ | H₃C-O-X₄ | X₅-(1-methylpiperidin-4-yl) |
| 163 | H | X₂—CH₂CH₃ | R | X₃-CH₂CH(CH₃)₂ | CH₃O-X₄ | X₅-quinuclidinyl |
| 164 | H | X₂—CH₂CH₃ | R | X₃-CH₂CH(CH₃)₂ | CH₃O-X₄ | X₅-(CH₂)₃N(CH₃)₂ |
| 165 | H | X₂—CH₂CH₃ | R | X₃-CH₂CH(CH₃)₂ | CH₃O-X₄ | X₅-(CH₂)₃N(CH₂CH₃)₂ |
| 166 | H | X₁—CH₂CH₃ | R | X₃-cyclopentyl | CH₃O-X₄ | X₅-(4-morpholinomethyl)phenyl |
| 167 | H | X₂—CH₂CH₃ | R | X₃-CH₂CH(CH₃)₂ | CH₃O-X₄ | X₅-(1-methylpyrrolidin-2-yl)ethyl |

TABLE 1-continued

| Example | R¹ | R² | Config. R¹ or R² | R³ | R⁴ | $L_n$-$R^5{}_m$ |
|---|---|---|---|---|---|---|
| 168 | H | X₂—CH₃ | R | X₃—CH₂CH₂CH(CH₃)₂ | CH₃O—X₄ | X₅—C(CH₃)₂CH₂N(CH₃)₂ (with H₃C–N–CH₃) |
| 169 | H | X₂—CH₃ | R | X₃—CH₂CH₂CH(CH₃)₂ | CH₃O—X₄ | X₅—(CH₂)₃-piperidinyl |
| 170 | H | X₂—CH₃ | R | X₃—CH₂CH₂CH(CH₃)₂ | CH₃O—X₄ | X₅—(CH₂)₂-pyrrolidinyl |
| 171 | H | X₂—CH₃ | R | X₃—CH₂CH₂CH(CH₃)₂ | CH₃O—X₄ | X₅—(1-methylpiperidin-4-yl) |
| 172 | H | X₂—CH₃ | R | X₃—CH₂CH₂CH(CH₃)₂ | CH₃O—X₄ | X₅—(1-methylazepan-4-yl) |
| 173 | H | X₂—CH₃ | R | X₃—CH₂CH₂CH(CH₃)₂ | CH₃O—X₄ | X₅—(N-methyl-tropanyl) |

TABLE 1-continued

| Example | R¹ | R² | Config. R¹ or R² | R³ | R⁴ | Lₙ-R⁵ₘ |
|---|---|---|---|---|---|---|
| 174 | H | X₂-CH₃ | R | X₃-CH₂CH(CH₃)₂ (isopentyl) | OCH₃ / X₄ | 1-benzylpiperidin-4-yl (X₅) |
| 175 | H | X₂⋯CH₃ | R | X₃-cyclopentyl | OCH₃ / X₄ | (CH₃)₂N-CH₂-C(CH₃)₂-X₅ |
| 176 | H | X₂-CH₃ | R | X₃-CH(CH₃)₂ | OCH₃ / X₄ | (CH₃)₂N-CH₂-C(CH₃)₂-X₅ |
| 177 | H | X₂-CH₃ | R | X₃-cyclopentyl | OCH₃ / X₄ | (CH₃)₂N-CH₂-C(CH₃)₂-X₅ |
| 178 | H | X₂-CH₃ | R | X₃-CH(CH₃)₂ | OCH₃ / X₄ | piperidin-4-yl (X₅) |
| 179 | H | X₂-CH₃ | R | X₃-CH₂CH(CH₃)₂ | OCH₃ / X₄ | piperidin-4-yl (X₅) |

Table 1-continued

| Example | R¹ | R² | Config. R¹ or R² | R³ | R⁴ | Lₙ-R⁵ₘ |
|---|---|---|---|---|---|---|
| 180 | H | X₂—CH₃ | R | X₃-cyclohexyl | H₃C-O-X₄ | X₅-(4-piperidinyl)-N-benzyl |
| 181 | H | X₂◀CH₃ | R | X₃-tetrahydropyran-4-yl | CH₃-O-X₄ | X₅-(4-piperidinyl)-N-benzyl |
| 182 | H | X₂◀CH₃ | R | X₃-cyclopentyl | CH₃-O-X₄ | H₃C-C(CH₃)₂-CH₂-N(morpholino)-X₅ |
| 183 | H | X₂—CH₃ | R | X₃-CH(CH₃)₂ | CH₃-O-X₄ | H₃C-C(CH₃)₂-CH₂-N(morpholino)-X₅ |
| 184 | H | X₂—CH₃ | R | X₃-cyclopentyl | CH₃-O-X₄ | H₃C-C(CH₃)₂-CH₂-N(morpholino)-X₅ |

Table 1-continued

| Example | R¹ | R² | Config. R¹ or R² | R³ | R⁴ | Lₙ-R⁵ₘ |
|---|---|---|---|---|---|---|
| 185 | H | X₂–CH₃ | R | 4-methoxyphenyl (X₃) | OCH₃ (X₄) | neopentyl-morpholine (X₅) |
| 186 | H | X₂–CH₃ | R | cyclohexyl (X₃) | OCH₃ (X₄) | 4-(4-methylpiperazin-1-yl)phenyl (X₅) |
| 187 | H | X₂–CH₂CH₃ | R | cyclopentyl (X₃) | OCH₃ (X₄) | 4-(4-methylpiperazin-1-yl)phenyl (X₅) |
| 188 | H | X₂–CH₃ | R | cyclopentyl (X₃) | Cl (X₄) | 1-methylpiperidin-4-yl (X₅) |
| 189 | H | X₂–CH₂CH₃ | R | cyclohexyl (X₃) | OCH₃ (X₄) | trans-4-morpholinocyclohexyl (X₅) |

Table 1-continued

| Example | R¹ | R² | Config. R¹ or R² | R³ | R⁴ | L$_n$-R⁵$_m$ |
|---|---|---|---|---|---|---|
| 190 | H | X₂―CH₃ | R | X₃-cyclopentyl | CH₃-O-X₄ | X₅-(4-piperidinyl, NH) |
| 191 | H | X₂-cyclopropyl | R | X₃-CH(CH₃)₂ | H₃C-CH₂-O-X₄ | X₅-(1-methyl-4-piperidinyl) |
| 192 | H | X₂―CH₃ | R | X₃-cyclohexyl | CH₃-O-X₄ | H₃C, CH₃ neopentyl-morpholine with X₅ |
| 193 | H | X₂―CH₃ | R | X₃-cyclohexyl | CH₃-O-X₄ | H₃C, CH₃ neopentyl-morpholine with X₅ |
| 194 | H | X₂―CH₃ | R | X₃-phenyl | CH₃-O-X₄ | H₃C, CH₃ neopentyl-morpholine with X₅ |
| 195 | H | X₂―CH₃ | R | X₃-CH₂CH(CH₃)₂ | CH₃-O-X₄ | H₃C, CH₃ neopentyl-morpholine with X₅ |

TABLE 1-continued

| Example | R¹ | R² | Config. R¹ or R² | R³ | R⁴ | Lₙ-R⁵ₘ |
|---|---|---|---|---|---|---|
| 196 | H | X₂–CH₂CH₃ | R | X₃–CH₂CH₂CH(CH₃)₂ | CH₃O–X₄ | neopentyl-N(4-methylpiperazine)–X₅ |
| 197 | H | X₂-cyclopropyl |  | X₃–CH₂CH₂CH(CH₃)₂ | CH₃O–X₄ | neopentyl-N(4-methylpiperazine)–X₅ |
| 198 | H | X₂,X₃-cyclobutyl | R |  | H₃C–O–X₄ | 1-methylpiperidin-4-yl–X₅ |
| 199 | H | X₂,X₃-cyclobutyl | R |  | H₃C–O–X₄ | trans-4-morpholinocyclohexyl–X₅ |
| 200 | H | X₂,X₃-cyclopentyl | R |  | CH₃O–X₄ | 1-methylpiperidin-4-yl–X₅ |

TABLE 1-continued
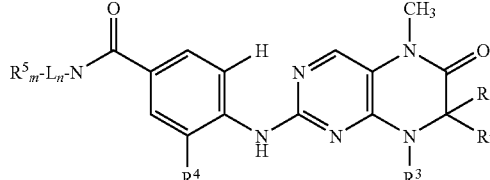
| Example | R¹ | R² | Config. R¹ or R² | R³ | R⁴ | L$_n$-R$^5_m$ |
|---|---|---|---|---|---|---|
| 201 | H | (cyclohexyl with X₂, X₃) | R | | CH₃-O-X₄ | 1-benzylpiperidin-4-yl (X₅) |
| 202 | X₁-CH₃ | X₂-CH₃ | | X₃-CH(CH₃)-CH₂- (isopentyl) | CH₃-O-X₄ | 4-(morpholinomethyl)phenyl (X₅) |
| 203 | H | X₂◂CH₃ | R | cyclopentyl (X₃) | Cl-X₄ | 1-benzylpiperidin-4-yl (X₅) |
| 204 | H | X₂◂CH₃ | R | X₃-CH₂-CH(CH₃)-CH₃ | CH₃-O-X₄ | 1-benzylpiperidin-4-yl (X₅) |

Table 1-continued

| Example | R¹ | R² | Config. R¹ or R² | R³ | R⁴ | Lₙ-R⁵ₘ |
|---|---|---|---|---|---|---|
| 205 | H | X₂▰CH₃ | R | X₃-CH₂CH(CH₃)CH₃ | X₄-O-CH₃ | X₅-cyclohexyl-morpholine |
| 206 | H | X₂▰CH₃ | R | X₃-CH₂C(CH₃)₃ | X₄-O-CH₃ | X₅-cyclohexyl-piperazine-CH₂-cyclopropyl |
| 207 | H | X₂▰CH₃ | R | X₃-CH₂C(CH₃)₃ | X₄-O-CH₃ | X₅-cyclohexyl-morpholine |
| 208 | H | X₂▰CH₃ | R | X₃-CH₂C(CH₃)₃ | X₄-O-CH₃ | X₅-cyclohexyl-piperazine-CH₂-cyclopropyl |

Table 1-continued
| Example | R¹ | R² | Config. R¹ or R² | R³ | R⁴ | Lₙ-R⁵ₘ |
|---|---|---|---|---|---|---|
| 209 | H | X₂─CH₃ | R | X₃ isobutyl | X₄─O─CH₃ | X₅ cyclohexyl-N-piperazinyl-N-CH₃ |
| 210 | H | X₂─CH₃ | R | X₃ cyclopentyl | X₄─O─CH₃ | X₅ cyclohexyl-N-piperazinyl-N-CH₃ |
| 211 | X₁─CH₃ | X₂─CH₃ | | X₃ isopentyl | X₄─O─CH₃ | X₅ cyclohexyl-N-morpholinyl |
| 212 | X₁─CH₃ | X₂─CH₃ | | X₃ isopentyl | X₄─O─CH₃ | X₅ cyclohexyl-N-piperazinyl-N-CH₂-cyclopropyl |

TABLE 1-continued

| Example | R¹ | R² | Config. R¹ or R² | R³ | R⁴ | Lₙ-R⁵ₘ |
|---|---|---|---|---|---|---|
| 213 | H | X₂◂CH₃ | R | X₃–cyclohexyl | X₄–O–CH₃ | X₅–cyclohexyl–piperazinyl–C(O)CH₃ |
| 214 | H | X₂–CH₂CH₃ | R | X₃–CH(CH₃)₂ | X₄–O–CH₃ | X₅–cyclohexyl–N-methylpiperazinyl |
| 215 | X₁–CH₃ | X₂–CH₃ | | X₃–CH₂CH(CH₃)₂ | X₄–O–CH₃ | X₅–cyclohexyl–N-methylpiperazinyl |
| 216 | H | X₂◂CH₃ | R | X₃–cyclohexyl | X₄–O–CH₃ | X₅–cyclohexyl–N-methylpiperazinyl |

Table 1-continued

| Example | R¹ | R² | Config. R¹ or R² | R³ | R⁴ | Lₙ-R⁵ₘ |
|---|---|---|---|---|---|---|
| 217 | H | X₂—CH₃ | R | X₃-cyclopentyl | X₄-O-CH₃ | X₅-cyclohexyl-N(piperazine)-CH₃ |
| 218 | H | X₂▬CH₃ | R | X₃-CH₂CH(CH₃)₂ (isobutyl-like, 3-methylbutyl) | X₄-O-CH₃ | X₅-cyclohexyl-N(thiomorpholine) |
| 219 | H | X₂—CH₃ | R | X₃-CH₂CH(CH₃)₂ | X₄-O-CH₃ | X₅-cyclohexyl-N(morpholine) |
| 220 | H | X₂▬CH₃ | R | X₃-CH₂C(CH₃)₃ | X₄-O-CH₃ | X₅-cyclohexyl-N(morpholine) |

TABLE 1-continued

| Example | R¹ | R² | Config. R¹ or R² | R³ | R⁴ | Lₙ-R⁵ₘ |
|---|---|---|---|---|---|---|
| 221 | H | X₂–CH₃ (wedge) | R | X₃–CH₂CH(CH₃)CH₃ | X₄–O–CH₃ | X₅–cyclohexyl-N(piperazine)-N-CH₃ (trans) |
| 222 | H | X₂–CH₂CH₃ | R | X₃–CH₂CH(CH₃)CH₃ | X₄–O–CH₃ | X₅–cyclohexyl-N(piperazine)-N-CH₃ (trans) |
| 223 | H | X₂–CH₃ (wedge) | R | X₃–phenyl | CH₃CH₂–O–X₄ | X₅–piperidine-N-CH₃ |
| 224 | H | X₂–CH₃ (wedge) | R | X₃–(3-methoxyphenyl) | CH₃–O–X₄ | X₅–piperidine-N-CH₃ |
| 225 | H | X₂–CH₃ (wedge) | R | X₃–(3-methoxyphenyl) | H | X₅–piperidine-N-CH₃ |

TABLE 1-continued

| Example | R¹ | R² | Config. R¹ or R² | R³ | R⁴ | Lₙ-R⁵ₘ |
|---|---|---|---|---|---|---|
| 226 | H | X₂▰CH₃ | R | X₃-(2-methoxyphenyl) | H₃C-O-X₄ | X₅-(1-methylpiperidin-4-yl) |
| 227 | H | X₂▰CH₃ | R | X₃-(2-methoxyphenyl) | CH₃-O-X₄ | H₃C-C(CH₃)-CH₂-N(pyrrolidine), X₅ |
| 228 | H | X₂▰CH₃ | R | X₃-CH₂CH₂CH(CH₃)₂ | X₄-O-CH₃ | X₅-(4,4-dimethylpiperidin-1-yl)cyclohexyl |
| 229 | H | X₂—CH₃ | R | X₃-phenyl | CH₃-O-X₄ | H₃C-C(CH₃)-CH₂-N(piperidine), X₅ |
| 230 | H | X₂▰CH₃ | R | X₃-cyclohexyl | CH₃-O-X₄ | H₃C-C(CH₃)-CH₂-N(piperidine), X₅ |

Table 1-continued
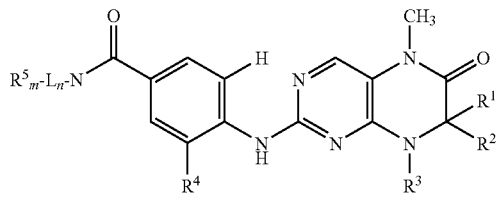
| Example | R¹ | R² | Config. R¹ or R² | R³ | R⁴ | $L_n\text{-}R^5{}_m$ |
|---|---|---|---|---|---|---|
| 231 | H |  | R | 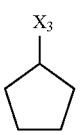 | 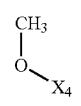 | 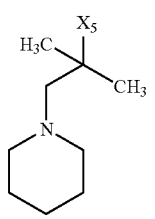 |
| 232 | H | 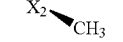 | R | 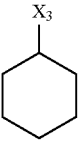 | 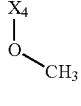 | 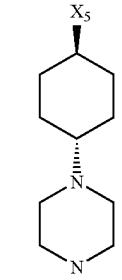 |
| 233 | H |  | R | 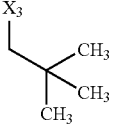 | 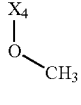 | 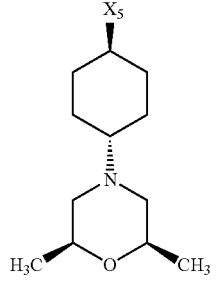 |
| 234 | H |  | R | 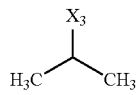 | 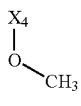 | 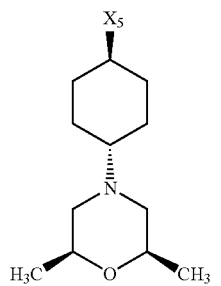 |

TABLE 1-continued

| Example | R¹ | R² | Config. R¹ or R² | R³ | R⁴ | Lₙ-R⁵ₘ |
|---|---|---|---|---|---|---|
| 235 | H | X₁–CH₃ | R | X₃–CH₂CH(CH₃)₂ (isobutyl) | X₄–O–CH₃ | X₅–cyclohexyl–N(thiomorpholine S-oxide) |
| 236 | H | X₁–CH₃ | R | X₃–CH₂CH(CH₃)₂ | X₄–O–CH₃ | X₅–cyclohexyl–N(thiomorpholine S-oxide) |
| 237 | H | X₁–CH₂CH₃ | R | X₃–CH(CH₃)₂ | CH₃–O–X₄ | X₅–piperidin-4-yl |
| 238 | H | X₁–CH₃ | R | X₃–cyclopentyl | CH₃–O–X₄ | X₅–piperidin-4-yl |
| 239 | H | X₁–CH₂CH₃ | R | X₃–cyclopentyl | CH₃–O–X₄ | X₅–C(CH₃)₂–CH₂–N(morpholine) |
| 240 | H | X₁–CH₃ | R | X₃–cyclohexyl | CH₃–O–X₄ | X₅–C(CH₃)₂–CH₂–N(CH₃)₂ |

Table 1-continued

| Example | R¹ | R² | Config. R¹ or R² | R³ | R⁴ | $L_n$-$R^5_m$ |
|---|---|---|---|---|---|---|
| 241 | H | $X_1$-CH₂CH₃ | R | $X_3$-CH₂CH₂CH(CH₃)₂ | CH₃-O-$X_4$ | $X_5$-C(CH₃)₂-CH₂-N(piperazine)-N-CH₃ |
| 242 | H | $X_1$-CH₂CH₃ | R | $X_3$-CH₂CH₂CH(CH₃)₂ | CH₃-O-$X_4$ | $X_5$-CH₂CH₂-piperidine |
| 243 | H | $X_1$-CH₂CH₃ | R | $X_3$-CH₂CH₂CH(CH₃)₂ | CH₃-O-$X_4$ | $X_5$-CH₂CH₂CH₂-N(CH₃)₂ |
| 244 | H | $X_1$-CH₂CH₃ | R | $X_3$-CH₂CH₂CH(CH₃)₂ | CH₃-O-$X_4$ | $X_5$-CH₂CH₂CH₂-N(piperazine)-N-CH₃ |

What is claimed is:

1. A pharmaceutical composition comprising:
   (i) a compound 1 of Formula (I)

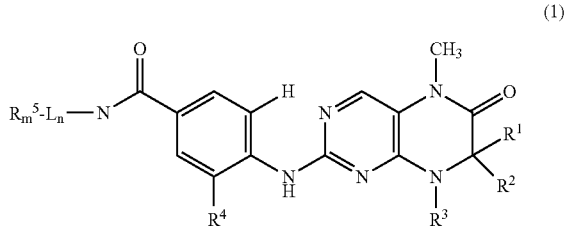

wherein the compound (1) is selected from the group consisting of the compounds of formula shown in the following Table:

| $R^1$ | $R^2$ | Config. $R^1$ or $R^2$ | $R^3$ | $R^4$ | $L_n$—$R^5_m$ |
|---|---|---|---|---|---|
| H | $X_2$⌒$CH_3$ | R | $X_3$–cyclopentyl | $H_3C$–O–$X_4$ | $X_5$–(N-methylpiperidinyl) |
| H | $X_2$⌒$CH_3$ | R | $X_3$–CH($CH_3$)$_2$ | $H_3C$–O–$X_4$ | $X_5$–(cyclohexyl-piperazinyl-CH$_2$-cyclopropyl) | optionally in form of its tautomers, racemates, enantiomers, diastereomers and the mixtures thereof and optionally in form of the pharmacologically acceptable acid addition salts; and (ii) at least one further chemotherapeutic or naturally occurring, semi-synthetic or synthetic therapeutic agent 2, which is selected from the group consisting of 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-{[4-(homomorpholin-4-yl)-1-oxo-2-buten-1-yl]amino}-7-[(S)-(tetrahydrofuran-3-yl)oxy]-quinazoline, 3-Z-[1-(4-(N-((4-methyl-piperazin-1-yl)-methylcarbonyl)-N-methyl-amino)-anilino)-1-phenyl-methylene]-6-methoxycarbonyl-2-indolinone, 3-Z-[1-(4-dimethylaminomethylanilino)-1-(4-(2-carboxyethyl)phenyl)methylene]-6-fluoro-2-indolinone, irinotecan, topotecan, oxaliplatin, docetaxel, paclitaxel, gemcitabine, pemetrexed, cisplatin, carboplatin, bevacizumab, cetuximab, gefitinib, 5-fluorouracil (5-FU) and erlotinib, or a tautomer, stereoisomer or a pharmaceutically acceptable salt thereof;
optionally in combination with one or more pharmaceutically acceptable excipients, and optionally for a co-treatment with radiotherapy or radio-immunotherapy, in the form of a combined preparation for simultaneous, separate or sequential administration.

2. The pharmaceutical composition according to claim 1, wherein the further chemotherapeutic or naturally occurring, semi-synthetic or synthetic therapeutic agent 2 is the di-maleic acid salt of the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline.

3. The pharmaceutical combination according to claim 1, wherein the further chemotherapeutic or naturally occurring, semi-synthetic or synthetic therapeutic agent 2 is the di-maleic acid salt of the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, or 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or a tautomer, stereoisomer or a pharmaceutically acceptable salt thereof.

4. The pharmaceutical combination according to claim 1, wherein the further chemotherapeutic or naturally occurring, semi-synthetic or synthetic therapeutic agent 2 is 4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, or a tautomer, stereoisomer or a pharmaceutically acceptable salt thereof.

5. The pharmaceutical combination according to claim 1, wherein the further chemotherapeutic or naturally occurring, semi-synthetic or synthetic therapeutic agent 2 is 3-Z-[1-(4-(N-((4-methyl-piperazin-1-yl)-methylcarbonyl)-N-methyl-amino)-anilino)-1-phenyl-methylene]-6-methoxycarbonyl-2-indolinone, or a pharmaceutically acceptable salt thereof.

6. The pharmaceutical combination according to claim 1, wherein the further chemotherapeutic or naturally occurring, semi-synthetic or synthetic therapeutic agent 2 is the mono-ethanesulfonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone.

7. The pharmaceutical composition according to claim 1, wherein the further chemotherapeutic or naturally occurring, semi-synthetic or synthetic therapeutic agent 2 is selected from the group consisting of irinotecan, topotecan, oxaliplatin, docetaxel, paclitaxel, gemcitabine, pemetrexed, cisplatin, carboplatin, bevacizumab, cetuximab, gefitinib, 5-fluorouracil (5-FU) or erlotinib or a pharmaceutically acceptable salt thereof.

8. The pharmaceutical composition according to claim 1, wherein the compound 1 is:

[structure diagram similar to Formula (I) with table below]

| $R^1$ | $R^2$ | Config. $R^1$ or $R^2$ | $R^3$ | $R^4$ | $L_n$—$R^5_m$ |
|---|---|---|---|---|---|
| H | $X_2$⌒$CH_3$ | R | $X_3$–cyclopentyl | $H_3C$–O–$X_4$ | $X_5$–(N-methylpiperidinyl) | wherein the abbreviations $X_2$, $X_3$, $X_4$ and $X_5$ used in the Table in each case denote a link to a position in the general Formula shown in the Table instead of the corresponding groups $R^1$, $R^2$, $R^3$, $R^4$ and L-$R^5$.

9. The pharmaceutical composition according to claim 1, wherein the compound 1 is:

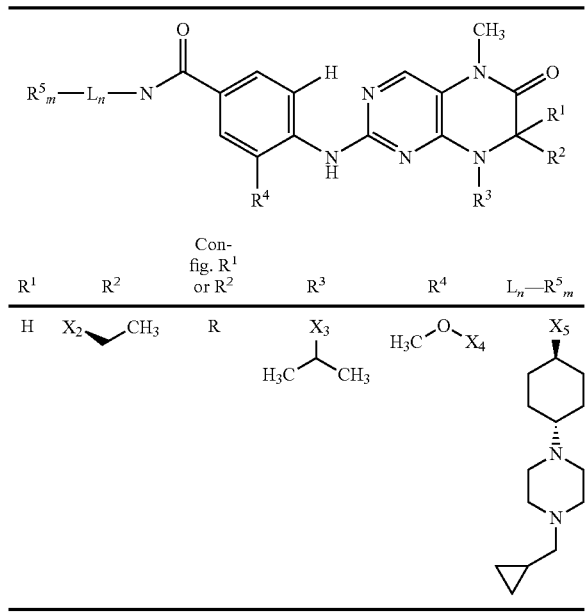

wherein the abbreviations $X_2$, $X_3$, $X_4$ and $X_5$ used in the Table in each case denote a link to a position in the general Formula shown in the Table instead of the corresponding groups $R^1$, $R^2$, $R^3$, $R^4$ and L-$R^5$.

10. The pharmaceutical combination according to claim 1, wherein the further chemotherapeutic or naturally occurring, semi-synthetic or synthetic therapeutic agent 2 is 3-Z-[1-(4-dimethylaminomethylanilino)-1-(4-(2-carboxyethyl)phenyl)methylene]-6-fluoro-2-indolinone, or a pharmaceutically acceptable salt thereof.

11. The pharmaceutical composition according to claim 1, wherein the further chemotherapeutic or naturally occurring, semi-synthetic or synthetic therapeutic agent 2 is 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline or a pharmaceutically acceptable salt thereof.

\* \* \* \* \*